(12) United States Patent
Ho et al.

(10) Patent No.: US 8,460,660 B2
(45) Date of Patent: Jun. 11, 2013

(54) ANTI-MESOTHELIN ANTIBODIES

(75) Inventors: Mitchell Ho, North Potomac, MD (US); Ira Pastan, Potomac, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/259,138

(22) PCT Filed: Mar. 23, 2010

(86) PCT No.: PCT/US2010/028336
§ 371 (c)(1),
(2), (4) Date: Jan. 13, 2012

(87) PCT Pub. No.: WO2010/111282
PCT Pub. Date: Sep. 30, 2010

(65) Prior Publication Data
US 2012/0107933 A1    May 3, 2012

Related U.S. Application Data

(60) Provisional application No. 61/162,778, filed on Mar. 24, 2009.

(51) Int. Cl.
*A61K 39/395* (2006.01)
*C07K 2317/21* (2006.01)
*C07K 2317/56* (2006.01)
*C07K 2317/565* (2006.01)
*C07K 2317/622* (2006.01)
*C07K 2317/732* (2006.01)
*C07K 2317/92* (2006.01)
*C07K 16/00* (2006.01)
*A61K 2039/505* (2006.01)

(52) U.S. Cl.
USPC ... 424/130.1; 435/69.1; 514/19.3; 530/387.3; 530/387.9; 530/388.1; 530/389.1; 536/23.53

(58) Field of Classification Search
None
See application file for complete search history.

(56) References Cited

U.S. PATENT DOCUMENTS
2007/0258982 A1 * 11/2007 Fouser et al. ............ 424/139.1

FOREIGN PATENT DOCUMENTS
| WO | WO 99/28471 A2 | 6/1999 |
| WO | WO03054020 | * 7/2003 |
| WO | WO 2006/124641 A2 | 11/2006 |
| WO | WO 2007/120766 A2 | 10/2007 |
| WO | WO 2009/120769 A1 | 10/2009 |

OTHER PUBLICATIONS

Ho et al, Int J Cancer. May 1, 2011; vol. 128, No. 9, pp. 2020-2030.*
Feng, Y., et al., "A novel human monoclonal antibody that binds with high affinity to mesothelin-expressing cells and kills them by antibody-dependent cell-mediated cytotoxicity," *Mol. Cancer Ther.*, vol. 8(5), pp. 1113-1118 (May 1, 2009).
Hassan, R., et al., "Preclinical evaluation of MORAb-009, a chimeric antibody targeting tumor-associated mesothelin," *Cancer Immunity*, vol. 7, p. 20, 10 pgs. (Dec. 19, 2007).
Hassan, R., et al., "Mesothelin targeted cancer immunotherapy," *European Journal of Cancer*, vol. 44(1), pp. 46-53 (Oct. 22, 2007).
Kaneko, O., et al., "A Binding Domain on Mesothelin for CA125/MUC16," *The Journal of Biological Chemistry*, vol. 284(6), pp. 3739-3749 (Feb. 6, 2009).
Pastan, I., et al., "Immunotoxin therapy of cancer," *Nature Review: Cancer*, vol. 6(7), pp. 559-565 (Jul. 1, 2006).
Presta, L., "Engineering of therapeutic antibodies to minimize immunogenicity and optimize function," *Advanced Drug Delivery Reviews*, vol. 58(5-6), pp. 640-656 (Aug. 7, 2006).
Vaughan, T., et al., "Human Antibodies with Sub-nanomolar Affinities Isolated from a Large Non-immunized Phage Display Library," *Nature Biotechnology*, vol. 14, pp. 309-314 (Mar. 1, 1996).

* cited by examiner

*Primary Examiner* — Bridget E Bunner
*Assistant Examiner* — Fozia Hamud
(74) *Attorney, Agent, or Firm* — Kilpatrick Townsend & Stockton LLP

(57) ABSTRACT

The present invention provides monoclonal anti-mesothelin antibodies and antibody fragments and methods for their use. The antibodies can be completely human.

19 Claims, 13 Drawing Sheets

HN1 VH:

```
                                            CDR1                       CDR2
HN1        QVQLVQSGAEVKRPGASVQVSCRASGYSINTYIMCWVRQAPGAGLEWMGVINPSG-VTSY
AAW67386   QVQLVQSGAEVKKPGASVKVSCKASGYTFTSYYMHWVRQAPGQGLEWMGIINPSGGSTSY
BAC01455   EVQLVESGAEVKKPGASVKVSCKASGYTFTSYYMHWVRQAPGQGLEWMGIINPSGGSTSY
ABM67163   QVQLVQSGAEVKKPGASVKVSCKASGYTFTSYYMHWVRQAPGQGLEWMGIINPSGGSTSY
AAY23310   EVQLVESGAEVKKPGASVKVSCKASGYTFTSYYMHWVRQAPGQGLEWMGIINPSGGSTSY
AAK57785   EVQLVESGAEVKKPGASVKVSCKASGYTFTSYYMHWVRQAPGQGLEWMGIINPSGVSTSY
IGHV1-46   QVQLVQSGAEVKKPGASVKVSCKASGYTFNSYYMHWVRQAPGQGLEWMGIINPSGGSTSY

CDR3
HN1        AQKFQGRVTLTNDTSTNTVYMQLNSLTSADTAVYYCARWALWGDFGM--DWGKGTLVTVSS
AAW67386   AQKFQGRVTMTRDTSTSTVYMELSSLRSEDTAVYYCAREGWFGDFGF--DPWGQGTLVTVSS
BAC01455   AQKFQGRVTMTRDTSTSTVYMELSSLRSEDTAVYYCARERGYGDYAF--DIWGQGTMVTVSS
ABM67163   AQKFQGRVTMTRDTSTSTVYMELSSLRSEDTAVYYCARDKGYGDYIP--DYWGQGTLVTVSS
AAY23310   AQKFQGRVTMTRDTSTSTVYMELSSLRSEDTAVYYCARDSVAGTYLI--DYWGQGTLVTVSS
AAK57785   AQKFQGRVTMTRDTSTSTVYMELSSLRSEDTAVYYCARGRIAVAGTDAFDIWGQGTMVTVCS
IGHV1-46   AQKFQGRVTMTRDTSTSTVYMQLSSLRSEDTAVYYCAR
```

HN1 VL:

```
                                            CDR1           CDR2
HN1        DIQMTQSPSTLSASIGDRVTITCRASEGIYHWLAWYQQKPGKAPKLLIYKASSLASGAPS
2CMR       DIQMTQSPSTLSASIGDRVTITCRASEGIYHWLAWYQQKPGKAPKLLIYKASSLASGAPS
CAO79111   DIQMTQSPSTLSASIGDRVTITCRASEGIYHWLAWYQQKPGKAPKLLIYKASSLASGAPS
CAO79109   DIQMTQSPSTLSASIGDRVTITCRASEGIYHWLAWYQQKPGKAPKLLIYKASSLASGAPS
CAD32240   DIQMTQSPSTLSASIGDRVTITCRASEGIYHWLAWYQQKPGKAPKLLIYKASSLASGAPS
CAA12399   DIQMTQSPSTLSASIGDRVTITCRASEGIYHWLAWYQQKPGKAPKLLIYKASSLASGAPS
IGKV1-5*03 DIQMTQSPSTLSASVGDRVTITCRASQSISSWLAWYQQKPGKAPKLLIYKASSLESGVPS

CDR3
HN1        RFSGSGSGTDFTLTISSLQPDDFATYYCQQYSNYPLTFGGGTKLEIK
2CMR       RFSGSGSGTDFTLTISSLQPDDFATYYCQQYSNYPLTFGGGTKLEIK
CAO79111   RFSGSGSGTDFTLTISSLQPDDFATYYCQQYSNYPLTFGGGTKLEIK
CAO79109   RFSGSGSGTDFTLTISSLQPDDFATYYCQQYSNYPLTFGGGTKLEIK
CAD32240   RFSGSGSGTDFTLTISSLQPDDFATYYCQQYSNYPLTFGGGTKLEIK
CAA12399   RFSGSGSGTDFTLTISSLQPDDFATYYCQQYSNYPLTFGGGTKLEIK
IGKV1-5*03 RFSGSGSGTDFTLTISSLQPDDFATYYCQQYNSYP
```

```
                       CDR1                           CDR2
HN2       EVQLLESGGGLVQPGGSLRPSCAAS GFTF SSYA MSWVRQAPGKGLEWVSA I SGS GGST HY
AAF75632  EVQLLESGGGLVQPGGSLRPSCAAS GFTFSSYA MSWVRQAPGKGLEWVSA ISGSGGST YY
BAC02290  EVQLVESGGGVVQPGGSLRPSCAAS GFTFSSYA MSWVRQAPGKGLEWVSA ISGSGGST YY
BAA36318  EVQLLESGGGLVQPGGSLKLSCAAS GFTFSSYA MSWVRQAPGKGLEWVSA ISGSGGST YY
BAG62929  EVQLLESGGGLVQPGGSLRLSCAAS GFTFSSYA MSWVRQAPGKGLEWVSA ISGSGGST YY
AAA52996  EVQLLESGGGLVQPGGSLRLSCAAS GFTFSSYA MSWVRQAPGKGLEWVSA ISGSGGST YY
                                                CDR3
HN2       ADSVKGRFTISRDNSKNTLYLQMNSLRAEDTAVYYC VRG GALG------ FDN WGRGTMVTVSS
AAF75632  ADSVKGRFTISRDNSKNTLYLQMNSLRAEDTAVYYC AKASSSGYYYVH--FDY WGQGTLVTVSS
BAC02290  ADSVKGRFTISRDNSKNTLYLQMNSLRAEDTAVYYC ARGSDYGDYLYYWYFDL WGRGTLVTVSS
BAA36318  ADSVKGRFTISRDNSKNTLYLQMNSLRAEDTAVYYC AK-GELA-------FDY WGQGTLVTVSS
BAG62929  ADSVKGRFTISRDNSKNTLYLQMNSLRAEDTAVYYC ARDLDGGNECL---FDY WGQGTLVTVSS
AAA52996  ADSVKGRFTISRDNSKNTLYLQMNSLRAEDTAVYYC AKDAGWGSG-----FDY WGQGTLVTVSS
```

HN2 VL:

```
                       CDR1                           CDR2
HN2       VLTQPPSVSEAPRQRVTISCSGS TSNIG SNV NWYQQFPGKPPKVVI Y YDD LVASGVSDR
BAH04805  VLTQPPSVSEAPRQRVTISCSGS SSNIGNNAV NWYQQLPGKAPKLLI Y YDD LPSGVSDR
AAQ56716  VLTQPPSVSEAPRQRVTISCSGS SSNIGNNAV NWYQQLPGKAPKLLI Y YDD LPSGVSDR
CAG27374  VLTQPPSVSEAPRQRVTISCSGS SSNIGNNAV NWYQQLPGKAPKLLI Y YDD LPSGVSDR
AAZ13621  VLTQPPSVSEAPRQRVTISCSGS SSNIGNNAV NWYQQLPGKAPKLLI Y YDD LPSGVSDR
CAD23536  VLTQPPSVSEAPRQRVTISCSGS SSNIGNNAV NWYQQLPGRAPKLLI Y YDD LPSGVSDR
                            CDR3
HN2       FSGSRSGTSASLAISGLQSEDEADYYC SA WDD SL NAWV FGGGTKVTV
BAH04805  FSGSKSGTSASLAISGLQSEDEADYYC AAWDDSLNAVV FGGGTKLTV
AAQ56716  FSGSKSGTSASLAISGLQSEDEADYYC AAWDDSLASYV FGGGTKLTV
CAG27374  FSGSKSGTSASLAISGLQSEDEADYYC AAWDDSLNGYV FGTGTKVTV
AAZ13621  FSGSKSGTSASLAISGLQSEDEADYYC AAWDDSLNGPV FGGGTKLTV
CAD23536  FSGSKSGTSASLAISGLQSEDEADYYC AAWDDSLNGVV FGGGTKLTV
```

VH:
CAGGTCCAGCTGGTGCAGTCTGGGGCTGAGGTGAAGAAGCCTGGGGCCTCAGTGAAGGTCTCCTGCAAGGCTTCTGGATACACCTTCACCAGTTACTATATGCACTGGGTGCGACAGGCCCCTGGACAAGGGCTTGAGTGGATGGGCGTTATCAACCCTAGTGGTGGTGTCACAAGTTACGCACAGAAGTTCCAGGGCAGAGTCACTTTGACCAACAGACACGTCCACAAACACAGTCTACATGGAGCTGAGCAGCCTGACATCTGCCGACACGGCCGTCTACTACTGTGCGAGATGGGCCTTATGGGGGACTTCGGTATGGGCAAGGAACCCTGGTCACCGTCTCGAGT

VL (kappa):
GACATCCAGATGACCCAGTCTCCTTCCACCCTGTCTGCATCTATTGGAGACAGAGTCACCATCACCTGCCGGGCCAGTCAGGGTATTTATCACTGGCTGGCCTGGTATCAGCAGAAACCAGGGAAAGCCCCTAAACTCCTGATCTATAAGGCCTCTAGTTTAGCCAGTGGGCTCCATCAAGTTCAGCGGCAGTGGATCTGGGACAGATTCACTCTCACCATCAGCAGCCTGCAGCCTGATGATTTTGCAACTTATTACTGCCAACATATAAGTAATTATCCGCTCACTTTCGGCGGAGGGACCAAGCTGGAGATCAAA

VH:
GAGGTGCAGCTGTTGGAGTCTGGGGGAGGCTTGGTACAGCCTGGGGGGTCCCTGAGACCCTCCTGTGCAGCCTCTGGATTCACCTTTAGCAGC
TATGCCATGAGCTGGGTCCGCCAGGCTCCAGGGAAGGGGCTGGAGTGGGTCTCAGCTATTAGTGGTAGTGGTAGTACAACACACTACGCAGAC
TCCGTGAAGGGCCGGTTCACCATCTCCAGAGACAATTCCAAGAACACGCTGTATCTGCAAATGAACAGCCTGAGAGCCGAGGACACGGCCGTG
TATTACTGTGTGAGAGGAGGGGCTTTGACAACTGGGGCCCGAGGGACAATGGTCACCGTCTCGAGT

VL (lambda):
GTGCTGACTCAGCCACCCTCGGTGTCTGAAGCCCCCAGGCAGAGGGTTCACCATCACCTGTTCTGGAAGCACCTCCAACATCGGAAGTAATGTT
GTTAACTGGTACCAGCAGTTCCCAGGAAAGCCTCCCAAAGTCGTCATCTATTATGATGATCTGGTGGGCCTCAGGGTCTCTGACCGATTTTCC
GGCTCCAGGTCTGGCACTTCAGCCTCCCTGGCCATCAGTGGGCTCCAGTCTGAAGATGAAGCTGATTATTATTGTCAGCATGGGATGACAGC
CTGAATGCCTGGGTGTTCGGTGGAGGGACCAAGGTCACCGTC

FIG. 4

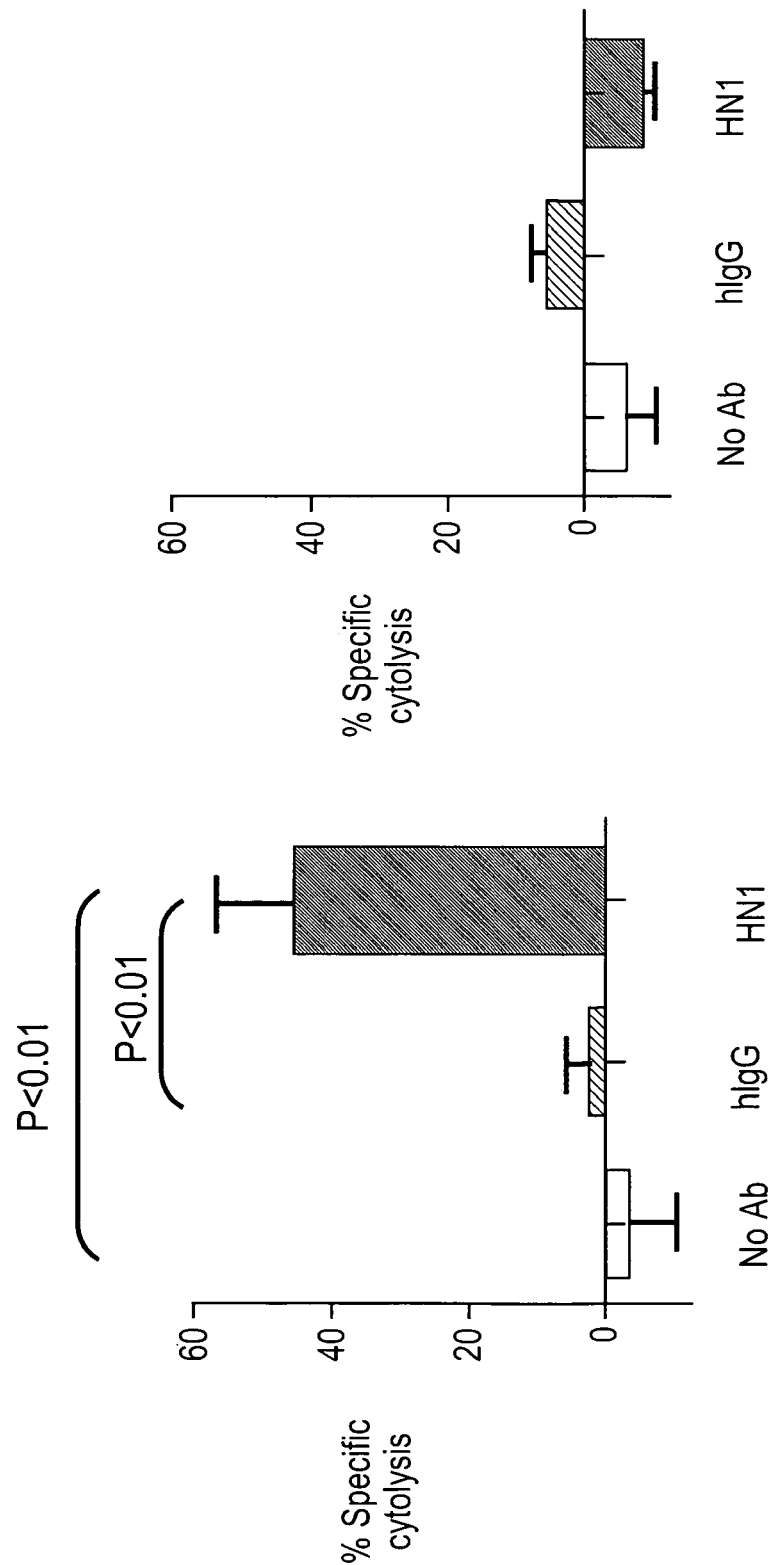

ANTI-MESOTHELIN ANTIBODIES

CROSS-REFERENCE TO RELATED APPLICATIONS

This application is a U.S. National Stage Application of PCT/US2010/028336, filed Mar. 23, 2010, which claims the benefit of U.S. Provisional Application No. 61/162,778, filed on Mar. 24, 2009, the entire disclosures of each of which are hereby incorporated herein by reference for all purposes.

FIELD OF THE INVENTION

The present invention provides human monoclonal antibodies that specifically bind to mesothelin.

BACKGROUND OF THE INVENTION

The development of effective drug regimens against ovarian cancer and mesothelioma has proven extremely difficult. One promising approach that can improve patient outcome is the use of monoclonal antibodies (mAb). Mabuchi, et al., *Curr Opin Obstet Gynecol* (2010) 22(1):3-8.

Mesothelin (MSLN) was first identified in 1992 with the mAb K1 that was generated by the immunization of mice with human ovarian carcinoma (OVCAR-3) cells (Chang, et al., *Int J. Cancer*. (1992) 50:373-81). The mesothelin gene (MSLN) encodes a 71-kilodalton (kDa) precursor protein that is processed to a 40-kDa protein termed mesothelin, which is a glycosyl-phosphatidylinositol-anchored glycoprotein present on the cell surface (Chang, et al, *Proc Natl Acad Sci USA* (1996) 93:136-40). Mesothelin is a differentiation antigen whose expression is limited to mesothelial cells lining the body cavity. It is also overexpressed in a variety of cancers including mesothelioma, ovarian cancer, and pancreatic cancer (Hassan, et al., *Eur J Cancer* (2008) 44:46-53). In addition, mesothelin is expressed on the surface of many lung adenocarcinomas and other types of lung cancer (Ordonez, *Am J Surg Pathol* (2003) 27:1418-28; Ho, et al., *Clin Cancer Res* (2007) 13:1571-5). It has been shown that mesothelin is shed from tumor cells (Hellstrom, et al, *Cancer Epidemiol Biomarkers Prev* (2006) 15:1014-20.; Ho, et al., *Cancer Epidemiol Biomarkers Prev* (2006) 15:1751). Shed serum mesothelin has been approved by the US Food and Drug Administration as a diagnostic biomarker in malignant mesothelioma.

CA125 (also known as MUC16) was first identified in 1981 with OC125, a mAb that had been developed from mice immunized with human ovarian cancer cells (Bast, et al., *J Clin Invest* (1981) 68:1331-7). The first cDNA clones were reported in 2001 (Yin, et al., *J Biol Chem* (2001) 276:27371-5). CA125 is a very large membrane-bound cell surface mucin, with an average molecular weight between 2.5 and 5 million Daltons owing to its extensive glycosylation with both O-linked and N-linked oligosaccharides (O'Brien, et al., *Tumour Biol* (2002) 23:154-69). The peptide backbone of CA125 is composed of an N-terminal region with extensive Ser/Thr/Pro-rich tandem repeats (TR) of 156 amino acids each with both N- and O-glycosylation, a SEA (sea urchin, enterokinase, agrin) domain with high levels of O-glycosylation and a C-terminal region with a short cytoplasmic tail (O'Brien, et al., *Tumour Biol* (2001) 22:348-66). CA125 is used as a biomarker in ovarian cancer due to its high expression in ovarian carcinomas and release into the serum (Bast, et al., *N Engl J Med* (1983) 309:883-7).

A majority (88%) of mesotheliomas are also CA125 positive on the cell membrane (Bateman, et al., *Histopathology* (1997) 30:49-56; Attanoos, et al., *Histopathology* (2002) 40:237-44). The biological functions of CA125 are not fully understood. Recent studies on corneal epithelial cells have showed that CA125 is expressed by the ocular surface epithelia and localized on the tips of the surface microplicae (Blalock, et al., *Invest Ophthalmol Vis Sci* (2007) 48:4509-18). CA125 is a multifunctional molecule linked to the actin cytoskeleton. Rump and colleagues have shown that mesothelin binds to CA125 and that this interaction may mediate cell adhesion (Rump, et al., *J Biol Chem* (2004) 279:9190-8). Since mesothelin is present on peritoneal mesothelium, there may be an important role for the mesothelin-CA125 interaction in the metastic spread of ovarian cancer and mesothelioma in the peritoneal cavity. The mesothelin binding site on CA125 probably lies within the 156 amino acid TR units, indicating multimeric binding of mesothelin to CA125 (Scholler, et al., *Cancer Lett*. (2007) 247:130-6). It has been found that the very abundant N-glycans on CA125, presumably in the TR region, are required for binding to both glycosylated and non-glycosylated mesothelin (Gubbels, et al., *Mol Cancer* (2006) 5:50-65). We have recently identified a region (296-359) of 64 amino acids at the N-terminus of cell surface mesothelin as the minimum fragment for binding activity to CA125 (Kaneko, et al., *J Biol Chem* (2009) 284: 3739-49).

Pastan and colleagues developed an immunotoxin (SS1P) that targets mesothelin expressing tumors. It contains a murine SS1 Fv fused to a 38-kDa fragment of *Pseudomonas* exotoxin A (PE38) (Pastan, et al., *Nat Rev Cancer* (2006) 6:559-65). Two Phase I clinical trials were completed at the National Cancer Institute (National Institutes of Health, Bethesda, Md.) and there was sufficient antitumor activity of SS1P to justify a Phase II trial. A chimeric antibody (MORAb-009) containing the same murine SS1 Fv for mesothelin was also developed and is currently being examined in a Phase II clinical trial for mesothelioma and pancreatic cancer (Hassan, et al., *Cancer Immun* (2007) 19:7:20).

BRIEF SUMMARY OF THE INVENTION

The present invention provides antibodies and antibody fragments that specifically bind to mesothelin. Accordingly, in one aspect, the invention provides an isolated antibody or antibody fragment that binds to mesothelin, the antibody comprising a heavy chain variable domain comprising a CDR1 of SEQ ID NO:9, a CDR2 of SEQ ID NO:10 and a CDR3 of SEQ ID NO:11 and a light chain variable domain comprising a CDR1 of SEQ ID NO:12, a CDR2 of SEQ ID NO:13 and a CDR3 of SEQ ID NO:14 ("an HN1 antibody"), the CDRs defined according to ImMunoGeneTics database (IMGT) (See, Lefranc, *Nucleic Acids Res* (2001) 29:207-9).

In a related aspect, the invention provides an isolated antibody or antibody fragment that binds to mesothelin, the antibody comprising a heavy chain variable domain comprising a CDR1 of SEQ ID NO:39, a CDR2 of SEQ ID NO:40 and a CDR3 of SEQ ID NO:41 and a light chain variable domain comprising a CDR1 of SEQ ID NO:42, a CDR2 of SEQ ID NO:43 and a CDR3 of SEQ ID NO:44 ("an HN1 antibody"), the CDRs defined according to Kabat (See, Kabat, et al., 5$^{th}$ Ed., National Institutes of Health Publication 91-3242, Bethesda, Md., 1991).

With respect to embodiments of the HN1 antibody, in some embodiments, the heavy chain variable domain has at least 90%, 93%, 95%, 97% or 99% sequence identity to SEQ ID NO:2. In some embodiments, the light chain variable domain has at least 90%, 93%, 95%, 97% or 99% sequence identity to SEQ ID NO:4. Generally, amino acid substitutions, additions and deletions are particularly tolerated within framework regions and within residues encoded by "hot-spot" motifs, as described herein and identified in the amino acid and nucleic acid sequences of the HN1 antibodies in FIGS. 1 and 3. In some embodiments, the HN1 antibody VH and VL chains have the amino acid sequence of SEQ ID NOS:2 and 4, respectively. Further residues in the framework and CDRs that tolerate substitution are shown in FIG. 1.

In another aspect, the invention provides an isolated antibody that binds to mesothelin, the antibody or antibody fragment comprising a heavy chain variable domain comprising a CDR1 of SEQ ID NO:15, a CDR2 of SEQ ID NO:16 and a CDR3 of SEQ ID NO:17 and a light chain variable domain comprising a CDR1 of SEQ ID NO:18, a CDR2 of SEQ ID NO:19 and a CDR3 of SEQ ID NO:20 ("an HN2 antibody"), the CDRs defined according to ImMunoGeneTics database (IMGT) (See, Lefranc, *Nucleic Acids Res* (2001) 29:207-9). With respect to embodiments of the HN2 antibody, in some embodiments, the heavy chain variable domain has at least 90%, 93%, 95%, 97% or 99% sequence identity to SEQ ID NO:6. In some embodiments, the light chain variable domain has at least 90%, 93%, 95%, 97% or 99% sequence identity to SEQ ID NO:8. Again, amino acid substitutions, additions and deletions are particularly tolerated within framework regions and within residues encoded by "hot-spot" motifs, as described herein and identified in the amino acid and nucleic acid sequences of the HN2 antibodies in FIGS. 2 and 4. In some embodiments, the HN2 antibody VH and VL chains have the amino acid sequence of SEQ ID NOS:6 and 8, respectively. Further residues in the framework and CDRs that tolerate substitution are shown in FIG. 2.

The antibodies or antibody fragments of the invention specifically bind to a mammalian mesothelin, for example, human mesothelin, mouse mesothelin, rat mesothelin, rabbit mesothelin, hamster mesothelin, mesothelin from a non-human primate (e.g., chimpanzee, macaque, gorilla, etc). The antibodies can be cross-reactive with a mesothelin protein from two or more species, e.g., specifically bind to human and mouse mesothelin. In some embodiments, the antibody specifically binds to human mesothelin without cross-reacting with mesothelin from another mammalian species, e.g., without cross-reacting with mouse mesothelin.

In some embodiments, the antibody is an intact immunoglobulin, for example, an IgG or an IgM. In some embodiments, the antibody is a human isotype IgG1. In some embodiments, the IgG1 constant region has an amino acid sequence of SEQ ID NO:48. In some embodiments, the HN1 heavy chain with IgG1 constant region has an amino acid sequence of SEQ ID NO:50. In some embodiments, the light chain is a κ chain. In some embodiments, the κ chain has an amino acid sequence of SEQ ID NO:52. In some embodiments, the HN1 light chain with κ chain has an amino acid sequence of SEQ ID NO:54.

In some embodiments, the antibody is an antibody fragment, e.g., an scFv, a dsFv, a diabody, a domain antibody, a Fab or a F(ab')2. In some embodiments, the antibody or antibody fragment is humanized or a chimeric antibody. In some embodiments, the antibody or antibody fragment is human. In some embodiments, the scFv has at least 90%, 93%, 95%, 97% or 99% sequence identity to SEQ ID NO:45. In some embodiments, the scFv has an amino acid sequence of SEQ ID NO:45. In some embodiments, the scFv is encoded by a nucleic acid sequence that has at least 90%, 93%, 95%, 97% or 99% sequence identity to SEQ ID NO:46. In some embodiments, the scFv is encoded by a nucleic acid sequence of SEQ ID NO:46.

In some embodiments, the antibodies of the invention bind mesothelin with a binding affinity ($K_D$) of about 100 nM or less, for example in the range of about 1-100 nM, for example, about 100 nM, 75 nM, 50 nM, 25 nM, 10 nM, 5 nM, 3 nM, 2 nM, 1 nM, or less.

In some embodiments, the antibody is linked to an effector agent. For example, the effector moiety or the therapeutic agent, e.g., a cytotoxin, a drug (e.g., an anticancer drug or chemotherapeutic drug as described herein), a radioisotope, or a liposome loaded with a drug or a cytotoxin. In some embodiments, the effector moiety or the therapeutic moiety is a cytotoxin. In some embodiments, the cytotoxin moiety is selected from *Pseudomonas* exotoxin A, diphtheria toxin, cholix toxin, cholera exotoxin, shiga toxin, ricin A, abrin, ribotoxin, ribonuclease, saporin, calicheamycin, botulinum toxins A through F and pokeweed antiviral protein (PAP). In some embodiments, the cytotoxin moiety is a *Pseudomonas* exotoxin A or variant thereof. In some embodiments, the *Pseudomonas* exotoxin A is selected from the group consisting of PE25, PE35, PE38, PE40, Domain III of PE, PE-LR, PE-6X, PE-LR/6X, PE-8X, PE-LR/8X, and variants thereof.

In some embodiments, the heavy chain (VH) and light chain (VL) variable regions of the antibodies of the invention are joined by a peptide linker. In some embodiments, the VH and said VL chains are connected by a disulfide bond between a cysteine residue engineered into each chain.

In some embodiments, the VH and the VL chains of the present antibodies each have complementarity determining regions ("CDRs") 1, 2, and 3, wherein CDRs 1, 2, and 3 of the VH chain and CDRs 1, 2, and 3 of the VL chain have the sequences shown in FIG. 1 or FIG. 2, and contain one or more substituted, added or deleted residues due to a mutation within a "hot-spot" motif in the encoding nucleic acid sequence, the "hot-spot" motifs in the sequences encoding the present antibodies being shown in FIGS. 3 and 4. For example, VH and the VL chains of the present antibodies can each have complementarity determining regions ("CDRs") 1, 2, and 3, wherein CDRs 1, 2, and 3 of the VH chain and CDRs 1, 2, and 3 of the VL chain have the sequences shown in FIG. 1 or FIG. 2, except:

(a) one or more CDRs have a mutation of a residue encoded by a codon with a nucleotide falling within (i) a tetranucleotide motif A/G-G-C/T-A/T or (ii) AGY, where Y can be a C or a T, or (b) one or more CDRs have a mutation of a residue that is not encoded by a codon with a nucleotide falling within (i) a tetranucleotide motif A/G-G-C/T-A/T or (ii) AGY, where Y can be a C or a T, or (c) one or more CDRs have a mutation of a residue that is encoded by a codon with a nucleotide falling within (i) a tetranucleotide motif A/G-G-C/T-A/T or (ii) AGY, where Y can be a C or a T, and one or more CDRs have a mutation of a residue that is not encoded by a codon with a nucleotide falling within (i) a tetranucleotide motif A/G-G-C/T-A/T or (ii) AGY, where Y can be a C or a T.

In a further group of embodiments, the invention provides immunoconjugates, immunotoxins or chimeric molecules comprising (a) an isolated antibody comprising CDRs 1, 2, and 3 of the VH chain and CDRs 1, 2, and 3 of the VL chain having the sequences shown in FIG. 1 or FIG. 2 (i.e., an HN1 or an HN2 antibody), as described herein, and (b) an effector moiety or a therapeutic moiety or a detectable label. In some embodiments, the VH and VL chains have 90%, 93%, 95% 97%, 99% or greater amino acid sequence identity to (i) SEQ ID NOS:2 and 4, respectively, or (ii) to SEQ ID NOS:6 and 8, respectively. In some embodiments, the VH and VL chains have the amino acid sequence of (i) SEQ ID NOS:2 and 4, respectively, or (ii) SEQ ID NOS:6 and 8, respectively. Further embodiments of the antibody moiety are as described herein. Residues in the framework and CDRs that tolerate substitution are shown in FIGS. 1 and 2.

In some embodiments, the effector moiety or the therapeutic moiety is selected from the group consisting of a cytotoxin, a drug (e.g., an antineoplastic drug or chemotherapeutic drug as described herein), a radioisotope, or a liposome loaded with a drug or a cytotoxin. In some embodiments, the effector moiety or the therapeutic moiety is a cytotoxin. In some embodiments, the cytotoxin moiety is selected from *Pseudomonas* exotoxin A, diphtheria toxin, cholix toxin, cholera exotoxin, shiga toxin, ricin A, abrin, ribotoxin, ribonuclease, saporin, calicheamycin, botulinum toxins A through F and pokeweed antiviral protein (PAP). In some embodiments, the cytotoxin moiety is a *Pseudomonas* exotoxin A or variant thereof. In some embodiments, the *Pseudomonas* exotoxin A is selected from the group consisting of PE25, PE35, PE38, PE40, Domain III of PE, PE-LR, PE-6X, PE-LR/6X, PE-8X, PE-LR/8X, and variants thereof.

In a further group of embodiments, the invention provides compositions comprising an antibody of the invention, and a pharmaceutically acceptable carrier. In some embodiments, the antibody is part of an immunoconjugate, immunotoxin or chimeric molecule. In some embodiments, the chimeric molecule includes a therapeutic moiety, the therapeutic moiety is selected from the group consisting of a cytotoxin, a drug (e.g., an anticancer drug or chemotherapeutic drug as described herein), a radioisotope, or a liposome loaded with a drug or a cytotoxin.

The invention further provides isolated nucleic acids encoding the HN1 and HN2 antibodies. With respect to an HN1 antibody or antibody fragment, the nucleic acid encodes a heavy chain variable domain comprising a CDR1 of SEQ ID NO:9, a CDR2 of SEQ ID NO:10 and a CDR3 of SEQ ID NO:11. Alternatively, the nucleic acid encodes a heavy chain variable domain comprising a CDR1 of SEQ ID NO:39, a CDR2 of SEQ ID NO:40 and a CDR3 of SEQ ID NO:41. The same or a second nucleic acid encodes a light chain variable domain comprising a CDR1 of SEQ ID NO:12, a CDR2 of SEQ ID NO:13 and a CDR3 of SEQ ID NO:14. Alternatively, the same or a second nucleic acid encodes a light chain variable domain comprising a CDR1 of SEQ ID NO:42, a CDR2 of SEQ ID NO:43 and a CDR3 of SEQ ID NO:44. With respect to embodiments of the nucleic acids encoding an HN1 antibody or antibody fragment, in some embodiments, the nucleic acid encodes a heavy chain variable domain sharing at least 90%, 93%, 95%, 97% or 99% sequence identity to SEQ ID NO:2. In some embodiments, the nucleic acid encodes a light chain variable domain sharing at least 90%, 93%, 95%, 97% or 99% sequence identity to SEQ ID NO:4. In some embodiments, the nucleic acid encoding an HN1 heavy chain variable domain has at least 90%, 93%, 95%, 97% or 99% sequence identity with SEQ ID NO:1. In some embodiments, the nucleic acid encoding an HN1 light chain variable domain has at least 90%, 93%, 95%, 97% or 99% sequence identity with SEQ ID NO:3. In some embodiments, the isolated nucleic acids encode VH and VL chains having the amino acid sequence of SEQ ID NOS:2 and 4, respectively. Generally, nucleic acid substitutions, additions and deletions are particularly tolerated within framework regions and within residues encoded by "hot-spot" motifs, as described herein and identified in the nucleic acid sequences of the HN1 antibodies in FIG. 3. In some embodiments, the isolated nucleic acids encoding the VH and VL chains have the nucleotide sequence of SEQ ID NOS:1 and 3, respectively.

With respect to an HN2 antibody or antibody fragment, the nucleic acid encodes a heavy chain variable domain comprising a CDR1 of SEQ ID NO:15, a CDR2 of SEQ ID NO:16 and a CDR3 of SEQ ID NO:17. The same or a second nucleic acid encodes a light chain variable domain comprising a CDR1 of SEQ ID NO:18, a CDR2 of SEQ ID NO:19 and a CDR3 of SEQ ID NO:20. With respect to embodiments of the nucleic acids encoding an HN2 antibody or antibody fragment, in some embodiments, the nucleic acid encodes a heavy chain variable domain sharing at least 90%, 93%, 95%, 97% or 99% sequence identity to SEQ ID NO:6. In some embodiments, the nucleic acid encodes a light chain variable domain sharing at least 90%, 93%, 95%, 97% or 99% sequence identity to SEQ ID NO:8. In some embodiments, the nucleic acid encoding an HN2 heavy chain variable domain has at least 90%, 93%, 95%, 97% or 99% sequence identity with SEQ ID NO:5. In some embodiments, the nucleic acid encoding an HN2 light chain variable domain has at least 90%, 93%, 95%, 97% or 99% sequence identity with SEQ ID NO:7. In some embodiments, the isolated nucleic acids encode VH and VL chains having the amino acid sequence of SEQ ID NOS:6 and 8, respectively. Again, nucleic acid substitutions, additions and deletions are particularly tolerated within framework regions and within residues encoded by "hot-spot" motifs, as described herein and identified in the nucleic acid sequences of the HN2 antibodies in FIG. 4. In some embodiments, the isolated nucleic acids encoding the VH and VL chains have the nucleotide sequence of SEQ ID NOS:5 and 7, respectively. Further embodiments of the nucleic acids encoding the antibodies are as described herein.

In some embodiments, the polynucleotide encoding the IgG1 constant region has an amino acid sequence of SEQ ID NO:39. In some embodiments, the polynucleotide encoding the HN1 heavy chain with IgG1 constant region has an amino acid sequence of SEQ ID NO:41. In some embodiments, the polynucleotide encoding the κ chain has an amino acid sequence of SEQ ID NO:43. In some embodiments, the polynucleotide encoding the HN1 light chain with κ chain has an amino acid sequence of SEQ ID NO:45.

In some embodiments, the invention provides any of the nucleic acids encoding the present antibodies, as described herein, operably linked to a promoter. The invention further provides expression cassettes comprising the isolated nucleic acids of the present invention. The invention further provides host cells comprising the isolated nucleic acids of the present invention.

The invention further provides methods of inhibiting CA125/mesothelin-dependent cell attachment or CA125-mesothelin binding comprising contacting a cell expressing mesothelin with the HN1 or HN2 antibodies or antibody fragments of the invention. The methods can be performed in vitro or in vivo.

The invention also provides methods of inhibiting a cancer mediated by CA125/mesothelin-dependent cell attachment or CA125/mesothelin binding comprising contacting a cell expressing mesothelin with the HN1 and HN2 antibodies or antibody fragments of the invention. In some embodiments, the cancer mediated by CA125/mesothelin-dependent cell attachment or CA125/mesothelin binding is selected from the group consisting of ovarian cancer, mesothelioma, non-small cell lung cancer, lung adenocarcinoma and pancreatic cancer.

The embodiments of the antibodies and antibody fragments used in the methods are as described herein. In some embodiments, the antibody can be in the form of an IgG molecule or a part of an immunoconjugate, immunotoxin or chimeric molecule, as described herein. The cell can be in vivo, in vitro or ex vivo. The cell can be a cancer cell that overexpresses mesothelin, e.g., in comparison to a non-cancer or normal cell. The cell can be a cancer cell whose growth, adhesion or migration is mediated by mesothelin-CA125 interactions. The growth of the cell is inhibited, e.g., by antibody-dependent cell-mediated cytotoxicity by using the antibody as an IgG, or by the actions of the effector or therapeutic moiety of an immunoconjugate or immunotoxin comprising the antibody. The embodiments of the antibodies are as described herein.

In a related group of embodiments, the invention provides methods for detecting the presence of a cell expressing mesothelin in a biological sample. The methods comprise contacting cells of said biological sample with an antibody of the invention. In some embodiments, the antibody is labeled, e.g., with a fluorescent, enzymatic or radioactive moiety. In some embodiments, the antibody has a constant region, e.g., IgG, IgM, IgA, that is conveniently detected with a labeled secondary antibody. The embodiments of the antibodies are as described herein.

In another group of embodiments, the invention provides kits, e.g., for detecting the presence of a mesothelin-expressing cell in a biological sample. The kits comprise one or more antibodies of the invention. The kits can also comprise a container and instructions for use of the one or more antibodies. In some embodiments, the antibodies are labeled or are in the form of an immunoconjugate or immunotoxin. The embodiments of the antibodies are as described herein. In some embodiments, the kits further comprise a secondary antibody and/or a detectable label.

DEFINITIONS

Units, prefixes, and symbols are denoted in their Systéme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

The term "mesothelin" refers to a protein and fragments thereof present on the surface of some human cells and bound by, for example, the K1 antibody. Nucleic acid and amino acid sequences of mesothelin are set forth in, for example, PCT published application WO 97/25,068 and U.S. Pat. Nos. 6,083,502 and 6,153,430. See also, Chang, K. & Pastan, I., *Int. J. Cancer* 57:90 (1994); Chang, K. & Pastan, I., *Proc. Nat'l Acad. Sci. USA* 93:136 (1996); Brinkmann U., et al., *Int. J. Cancer* 71:638 (1997); Chowdhury, P. S., et al., *Mol. Immunol.* 34:9 (1997), and U.S. Pat. No. 6,809,184. Mesothelin is expressed as a precursor protein of approximately 69 kDa, that then is processed to release a 30 kDa protein, while leaving attached to the cell surface the 40 kDa glycosylphosphatidylinositol linked cell surface glycoprotein described in the Background. The 40 kDa glycoprotein is the one referred to by the term "mesothelin" herein. The nucleic acid and amino acid sequences of mesothelin have been recorded from several species, e.g., human (NM_005823.4→NP_005814.2; and NM_013404.3→NP_037536.2), mouse (NM_018857.1→NP_061345.1), rat (NM_031658.1→NP_113846.1), bovine (NM_001100374.1→NP_001093844).

"Antibodies" exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to VH—CH by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, W. E. Paul, ed., Fundamental Immunology, Raven Press, N.Y. (1993), for a more detailed description of these and other antibody fragments). While various antibody fragments are defined in terms of the digestion of an intact antibody, one of skill will appreciate that such Fab' fragments may be synthesized de novo either chemically or by utilizing recombinant DNA methodology.

For convenience of reference, as used herein, the term "antibody" includes whole (sometimes referred to herein as "intact") antibodies, antibody fragments that retain antigen recognition and binding capability, whether produced by the modification of whole antibodies or synthesized de novo using recombinant DNA methodologies, monoclonal antibodies, polyclonal antibodies, and antibody mimics, unless otherwise required by context. The antibody may be an IgM, IgG (e.g. $IgG_1$, $IgG_2$, $IgG_3$ or $IgG_4$), IgD, IgA or IgE). In some embodiments, the antibody is an isotype human IgG1, for example, an isotype human IgGγ1.

The term "antibody fragments" means molecules that comprise a portion of an intact antibody, generally the antigen binding or variable region of the intact antibody. Examples of antibody fragments include Fab, Fab', F(ab')2, and Fv fragments; helix-stabilized antibodies (see, e.g., Arndt et al., J Mol Biol 312:221-228 (2001); diabodies (see below); single-chain antibody molecules ("scFvs," see, e.g., U.S. Pat. No. 5,888,773); disulfide stabilized antibodies ("dsFvs", see, e.g., U.S. Pat. Nos. 5,747,654 and 6,558,672), and domain antibodies ("dAbs," see, e.g., Holt et al., Trends Biotech 21(11): 484-490 (2003), Ghahroudi et al., FEBS Lett. 414:521-526 (1997), Lauwereys et al., EMBO J. 17:3512-3520 (1998), Reiter et al., J. Mol. Biol. 290:685-698 (1999), Davies and Riechmann, Biotechnology, 13:475-479 (2001)).

As used herein, the term "anti-mesothelin" in reference to an antibody, includes reference to an antibody which is generated against mesothelin. The mesothelin generally is a mammalian mesothelin. In some embodiments, the mesothelin is a primate mesothelin, for example, human mesothelin. In one embodiment, the antibody is generated against human mesothelin synthesized by a non-primate mammal after introduction into the animal of cDNA which encodes human mesothelin. The antibodies can be cross-reactive with mesothelin proteins from different mammalian species, e.g., human, mouse, non-human primate.

The term "diabodies" refers to small antibody fragments with two antigen-binding sites, which fragments comprise a variable heavy domain ("$V_H$" or "VH") connected to a variable light domain ("$V_L$" or "VL") in the same polypeptide chain ($V_H$-$V_L$). By using a linker that is too short to allow pairing between the two domains on the same chain, the domains are forced to pair with the complementary domains of another chain and create two antigen-binding sites. Diabodies and their production are described more fully in, for example, EP 404,097; WO 93/11161; and Holliger et al., Proc. Natl. Acad. Sci. USA, 90: 6444-6448 (1993).

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs".

The extent of the framework region and CDRs have been defined. (see, Kabat, E., et al., SEQUENCES OF PROTEINS OF IMMUNOLOGICAL INTEREST, U.S. Department of Health and Human Services, (1987), which is hereby incorporated by reference). The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

References to "VH" or a "$V_H$" refer to the variable region of an immunoglobulin heavy chain, including an Fv, scFv, dAb, dsFv or Fab. References to "VL" or a "$V_L$" refer to the variable region of an immunoglobulin light chain, including of an Fv, scFv, dsFv, dAb, or Fab.

The term "Fv" refers to the variable domains of the heavy chain and of the light chain of an antibody. The phrase "single chain Fv" or "scFv" refers to an antibody in which the variable domains of the heavy chain and of the light chain of a traditional two chain antibody have been joined to form one chain. Optionally, a linker (usually a peptide) is inserted between the two chains to allow for proper folding and creation of an active binding site. If a linker is present, it is excluded for purposes of comparing the percentage of sequence identity between a given VH or VL chain and a VH or VL chain of the HN1 or the HN2 antibodies.

An antibody immunologically reactive with a particular antigen can be generated by recombinant methods such as selection of libraries of recombinant antibodies in phage or similar vectors, see, e.g., Huse, et al., Science 246:1275-1281 (1989); Ward, et al., Nature 341:544-546 (1989); and Vaughan, et al., Nature Biotech. 14:309-314 (1996), or by immunizing an animal with the antigen or with DNA encoding the antigen.

The extent of the framework region and CDRs have been defined. The sequences of the framework regions of different light or heavy chains are relatively conserved within a species. The framework region of an antibody, that is the combined framework regions of the constituent light and heavy chains, serves to position and align the CDRs in three dimensional space.

The antibodies of the present invention can be encoded by nucleic acid sequences that correspond to a human germline sequence. The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other evaluated variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementary determining regions only, framework and complementary determining regions, a variable segment, or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 92%, 94%, 96%, 98%, 99% sequence identity with the reference variable region nucleic acid or amino acid sequence. Corresponding human germline sequences can be determined, for example, through the publicly available international ImMunoGeneTics database (IMGT) (on the worldwide web at imgt.cines.fr/) and V-base (on the worldwide web at vbase.mrc-cpe.cam.ac.uk).

The term "linker peptide" includes reference to a peptide within an antibody binding fragment (e.g., Fv fragment) which serves to indirectly bond the variable domain of the heavy chain to the variable domain of the light chain.

The term "parental antibody" means any antibody of interest which is to be mutated or varied to obtain antibodies or fragments thereof which bind to the same epitope as the parental antibody, but with higher affinity.

The term "hotspot" means a portion of a nucleotide sequence of a CDR or of a framework region of a variable domain which is a site of particularly high natural variation. Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequences motifs which are especially well characterized are the tetranucleotide sequence RGYW and the serine sequence AGY, where R is A or G, Y is C or T, and W is A or T.

A "targeting moiety" is the portion of an immunoconjugate intended to target the immunoconjugate to a cell of interest. Typically, the targeting moiety is an antibody, a scFv, a dsFv, an Fab, or an F(ab')$_2$.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as anti-neoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The terms "chimeric molecule" and "immunoconjugate" refer to linkage of an antibody to an effector moiety. The linkage is usually a covalent bond between the effector moiety and the antibody. The linkage can be by chemical conjugation, or by expressing the antibody and the effector moiety from a nucleic acid encoding both the antibody and the effector moiety. For example, a nucleic acid encoding an HN1 or HN2 antibody of the invention fused to a *Pseudomonas* exotoxin can be recombinantly expressed in *E. coli* and then isolated.

The terms "effective amount" or "amount effective to" or "therapeutically effective amount" includes reference to a dosage of a therapeutic agent sufficient to produce a desired result, such as inhibiting cell protein synthesis or tumor growth by at least 50%, or killing the cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "connected to," in relation to an antibody and a therapeutic moiety or detectable label, means that the antibody is fused to (e.g., by recombinant expression) or conjugated to (e.g., chemically attached to) the therapeutic moiety or detectable label, directly or through a linker.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide").

The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

| Amino Acid Nomenclature | | |
|---|---|---|
| Name | 3-letter | 1-letter |
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |

TABLE A-continued

| Amino Acid Nomenclature | | |
|---|---|---|
| Name | 3-letter | 1-letter |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

| |
|---|
| 1) Alanine (A), Serine (S), Threonine (T); |
| 2) Aspartic acid (D), Glutamic acid (E); |
| 3) Asparagine (N), Glutamine (Q); |
| 4) Arginine (R), Lysine (K); |
| 5) Isoleucine (I), Leucine (L), Methionine (M), Valine (V); and |
| 6) Phenylalanine (F), Tyrosine (Y), Tryptophan (W). |

See also, Creighton, *Proteins: Structures and Molecular Properties*, W.H. Freeman and Company, New York (2nd Ed., 1992).

The terms "substantially similar" in the context of a peptide indicates that a peptide comprises a sequence with at least 90%, for example at least 95%, sequence identity to the reference sequence (e.g., SEQ ID NOS:2 and 4 or SEQ ID NOS:6 and 8) over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA* 82:2306-2309 (1985), or the ciliate Macronucleus, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, for example at least 80%, or at least 90-95% nucleotide or amino acid residue identity, when compared and aligned for maximum correspondence, as measured using one of the following sequence comparison algorithms or by visual inspection. The substantial identity can exist over a region of the sequences that is at least about 50 residues in length, for example, over a region of at least about 100 residues, or over at least about 150 residues. In one embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (on the internet by entering "www." followed by "ncbi.nlm.nih.gov/"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (e.g., SEQ ID NOS:1 and 3 or SEQ ID NOS:5 and 7) if the smallest sum probability in a comparison of the test nucleic acid to the reference nucleic acid is less than about 0.1, for example less than about 0.01, or less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, non-human primates, rats, mice, hamsters, guinea pigs, chimpanzees, or macaques. The cells may be cultured in vivo or in vitro.

The term "selectively reactive" or "specifically binds" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, for example greater than 5-fold, or greater than 10-fold and can result in greater than 100-fold increase in amount of bound antibody (per unit time) to a cell or tissue bearing mesothelin as compared to a cell or tissue lacking mesothelin. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods of the present invention are generally "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

A cancer "mediated by CA125/mesothelin binding" or requiring "CA125/mesothelin mediated cell adhesion" refers to cancers whose growth, spread or progression can be partially or wholly inhibited or reduced by interfering with or blocking the binding interaction of CA125 to mesothelin. Such cancers may have tumor cells that overexpress or express high levels of mesothelin and/or CA125, e.g., in comparison to normal cells of the same tissue type or in comparison to cancer cells of distinct tissue types. Exemplary cancers whose growth, spread and/or progression are at least partially mediated by CA125/mesothelin binding include ovarian cancer, mesothelioma, non-small cell lung cancer, lung adenocarcinoma and pancreatic cancer.

The terms "inhibiting," "reducing," "decreasing" with respect to tumor or cancer growth or progression refers to inhibiting the growth, spread, metastasis of a tumor or cancer in a subject by a measurable amount using any method known in the art. The growth, progression or spread of a tumor or cancer is inhibited, reduced or decreased if the tumor burden is at least about 10%, 20%, 30%, 50%, 80%, or 100% reduced in comparison to the tumor burden prior to administration of an anti-mesothelin antibody or antibody fragment. In some embodiments, the growth, progression or spread of a tumor or cancer is inhibited, reduced or decreased by at least about 1-fold, 2-fold, 3-fold, 4-fold, or more in comparison to the tumor burden prior to administration of an anti-mesothelin antibody or antibody fragment.

The term "co-administered" refers to two active pharmacological agents in the blood or body tissues of a host at the same time. Co-administered agents can be concurrently administered, or sequentially administered.

Compositions or methods "comprising" one or more recited elements may include other elements not specifically recited. For example, a composition that comprises the VH and VL CDR sequences of the invention encompasses both the CDRs and the variable regions, antibodies and antibody fragments comprising the CDRs.

Compositions or methods "consisting essentially of" one or more recited elements include the elements specifically recited and may further include pharmacologically inactive components (e.g., excipients, vehicles), but do not include unrecited pharmacologically active agents.

BRIEF DESCRIPTION OF THE DRAWINGS

FIG. 1 provides sequence analyses of the heavy (VH) (SEQ ID NO:2) and light (VL) (SEQ ID NO:4) amino acid sequences of antibody HN1. The amino acid sequences were aligned with 5 closest homologs found in public databases (VH=SEQ ID NOS:21-25; VL=SEQ ID NO:4, all identical sequences). In particular, the Fv sequence homologs in public databases were found using NCBFs Blastp program (found on the worldwide web at blast.ncbi.nlm.nih.gov/Blast.cgi). The 5 known Fv sequences with top scores were selected to align with the VH and VL of HN1. The CDR regions are defined according to Kabat, et al., "Sequences of proteins of immunological interest," 5th Ed., National Institutes of Health Publication 91-3242, Bethesda, Md., 1991 (italics) and Lefranc, "IMGT, the international immunogene tics database," Nucleic Acids Res (2001) 29:207-9 (light shading). The CDR regions (light shading) were identified using IMGT's V-Quest program for human Ig sequences (found on the worldwide web at imgt.orgZIMGT_vquestZvquest?livret=0&Option=humanIg). Amino acids encoded by the somatic hypermutation hotspot nucleotide sequences (A/G)G(C/T)(A/T) (i.e., "RGYW") or AG(C/T) (i.e., "AGY") within CDRs that can be used for in vivo or in vitro affinity maturation are underlined. The germline sequences (IGHV1-46 (SEQ ID NO:56) for VH and IGKV1-5*03 (SEQ ID NO: 57) for VL) were also aligned with HN1 except VH's CDR3. The somatic mutations (residues different from germline residues) in HN1 are shown in dark shading.

FIG. 2 provides sequence analyses of the heavy (VH) (SEQ ID NO:6) and light (VL) (SEQ ID NO:8) amino acid sequences of antibody HN2. The amino acid sequences were aligned with 5 closest homologs found in public databases (VH=SEQ ID NOS:26-30; VL=SEQ ID NOS:31-35). As with the analysis for the HN1 amino acid sequences, the Fv sequence homologs in public databases were found using NCBI's Blastp program. The 5 known Fv sequences with top scores were selected to align with the VH and VL of HN2. The CDR regions (shaded) were identified using IMGT's V-Quest program for human Ig sequences Amino acids encoded by the somatic hypermutation hotspot nucleotide sequences (A/G)G(C/T)(A/T) (i.e., "RGYW") or AG(C/T) (i.e., "AGY") within CDRs that can be used for in vivo or in vitro affinity maturation are underlined.

FIG. 3 provides sequence analyses of the heavy (VH) (SEQ ID NO:1) and light (VL) (SEQ ID NO:3) nucleic acid sequences of antibody HN1. CDR regions (shaded) were identified using IMGT's V-Quest program for human Ig sequences. The somatic hypermutation hotspot nucleotide sequences (A/G)G(C/T)(A/T) ("RGYW") or AG(C/T) ("AGY") within CDRs that can be used for in vivo or in vitro affinity maturation are underlined.

FIG. 4 provides sequence analyses of the heavy (VH) (SEQ ID NO:5) and light (VL) (SEQ ID NO:7) nucleic acid sequences of antibody HN2. CDR regions (shaded) were identified using IMGT's V-Quest program for human Ig sequences. The somatic hypermutation hotspot nucleotide sequences (A/G)G(C/T)(A/T) ("RGYW") or AG(C/T) ("AGY") within CDRs that can be used for in vivo or in vitro affinity maturation are underlined.

FIGS. 12A-12B illustrates that HN1 induces ADCC on mesothelin-expressing cancer cells. A. A431/H9 cells were used as target cells (T) and reacted with 10 μg/ml of HN1 or control human IgG (hIgG) in the presence of human PBMC as effecter cells (E) (E:T=100:1). Significant ADCC activity (*) was only noted with HN1 treatment compared with both the no antibody group (No Ab) or the isotype control treatment group (hIgG) (p<0.01). B. The assay was performed following the same protocol as shown in A, except that A431 cells that express no mesothelin were used as target cells.

DETAILED DESCRIPTION

1. Introduction

Figure 5A:
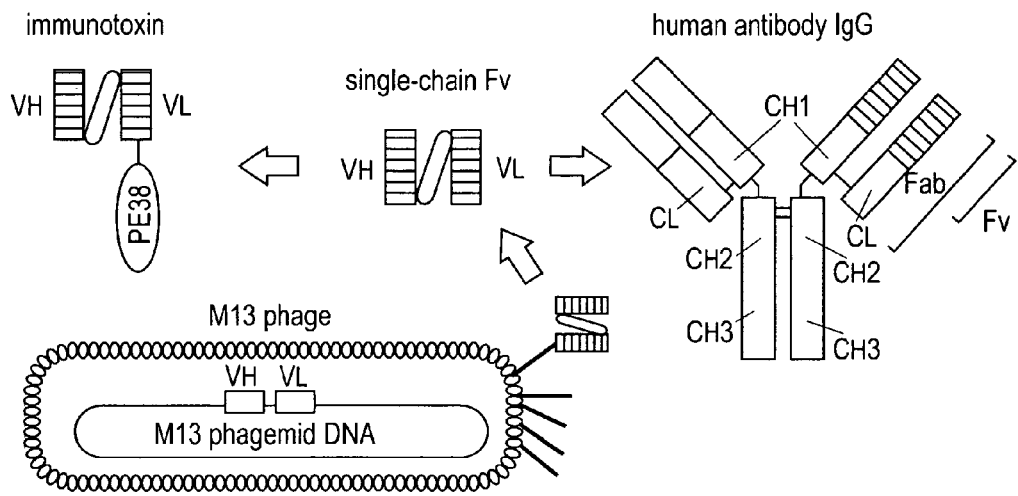
FIG. 5A illustrates a schematic of immunotoxin and human IgG. To make an anti-mesothelin immuntoxin, the HN1 scFv is fused to a truncated PE38. A fully human IgG was generated by fusing VH into the constant region of heavy chain γ 1 and VL into the constant region of human κ chain. The final human IgG molecule for HN1 is IgGγ1κ.

Mesothelin is a 40 kDa glycosylphosphatidylinositol linked cell surface glycoprotein present on normal mesothelial cells that is highly expressed in mesothelioma, ovarian cancer, pancreatic cancer, and some other malignancies (Chang, K. et al., *Am J Surg Pathol* 16:259-68 (1992); Chang, K. et al., *Int J Cancer* 50:373-81 (1992); Argani, P. et al., *Clin Cancer Res* 7:3862-8 (2001); Chang, K. et al., *Proc Natl Acad Sci USA* 93:136-40 (1996)). The normal biological function of mesothelin is unknown and mesothelin deficient mice have no phenotype (Bera, T. K. et al., *Mol Cell Biol* 20:2902-6 (2000)). Moreover, a recent reports indicate that mesothelin binds to CA125/MUC16, indicating that mesothelin plays a role in the metastatic spread of ovarian cancer (Rump, A. et al., *J Biol Chem* 279:9190-8 (2004) and Kaneko, et al., *J. Biol. Chem.* 284 (6), 3739-3749 (2009)). Because of its high expression in cancers and limited expression on normal tissues, mesothelin is a promising target for cancer immunotherapy.

The present invention demonstrates the successful isolation from a phase display of human scFv which recognize tumor-associated mesothelin. The antibodies described herein strongly and specifically to a conformation-sensitive epitope of mesothelin on cancer cells. The anti-mesothelin human antibodies can functionally block the interaction of mesothelin and CA125. Fully human anti-mesothelin IgG exhibits strong ADCC on cancer cells. When used as a targeting moiety on an immunotoxin, the anti-mesothelin human antibodies also induce strong apoptosis in cancer cells. The fully human anti-mesothelin antibodies described herein find use as therapeutic for the treatment of mesothelioma, ovarian cancer and other mesothelin-expressing malignant human tumors.

Mesothelin was found to elicit a humoral immune response in humans (Ho, et al., *Clin Cancer Res* (2005) 11:3814-20). The presence of circulating antibodies correlated with mesothelin overexpression on primary mesothelioma and ovarian cancer with advanced-stage disease. To isolate human anti-mesothelin antibodies, a large "naïve" human scFv phage display library derived from the PBL of healthy non-immunized donors was used. In theory, a large naïve library can be used to isolate any antibodies against any antigens including those previously found to be relatively toxic and nonimmunogenic. In the present study, we discovered a human mAb with evidence for somatic hypermutation and low nanomolar affinity for mesothelin that is comparable to the affinities of mAb derived from the secondary immune response. The affinity of the present anti-mesothelin antibodies is comparable to the mouse mAb specific for mesothelin (Chang, et al., *Int J. Cancer.* (1992) 50:373-81; Chowdhury, et al., *Proc Natl Acad Sci USA* (1998) 95:669-74; Scholler, et al., *Proc Natl Acad Sci USA* (1999) 96:11531-6; Onda, et al., *Clin Cancer Res* 2005; 11:5840-6). This result supports our previous observation that a baseline level of autoantibodies to mesothelin may exist in normal healthy donors (Ho, et al., *Clin Cancer Res* (2005) 11:3814-20).

The preparation of mAb against mesothelin has been achieved by different approaches. The first mAb to mesothelin (K1) was generated by immunization of mice with periodate-treated human ovarian carcinoma (OVCAR-3) cells (Chang, et al., *Int J. Cancer.* (1992) 50:373-81). Mouse spleen lymphocytes were selected prior to fusion using a panning purification method on living OVCAR-3 cells. The K1 clone was identified as an IgM isotype, but was subsequently isotype-switched to IgG1. The second approach used DNA immunization (Chowdhury, et al., *Proc Natl Acad Sci USA* (1998) 95:669-74). Mice were immunized with a eukaryotic expression vector coding for mesothelin. When high serum antibody titers were obtained, a phage display library was made from the splenic mRNA of these mice. An scFv-displaying phage (called SS) was selected that bound specifically to recombinant mesothelin and mesothelin-positive cells. The SS Fv was further improved by in vitro affinity maturation and developed as the SS1P immunotoxin and the MORAb-009 chimeric mAb currently in clinical trials for the treatment of mesothelioma, lung adenocarcinoma and pancreatic cancer (Chowdhury, et al., *Nat Biotechnol* (1999) 17:568-72). The third approach was to immunize mice with cancer cells from malignant ascites of a patient with ovarian carcinoma (Scholler, et al., *Proc Natl Acad Sci USA* (1999) 96:11531-6). A mouse hybridoma that makes a mAb, OV569 specific for mesothelin was found. OV569 is currently utilized as a diagnostic reagent to detect serum mesothelin in patients.

A fourth approach was to immunize mesothelin-deficient mice with plasmid cDNA encoding human mesothelin, and boosted with rFc-mesothelin fusion protein prior to cell fusion (Onda, et al., *Clin Cancer Res* (2005) 11:5840-6). Two high affinity murine mAbs, MN and MB, were obtained. They are used as reagents in immunohistochemistry and FACS. Whereas Fvs from murine sources have good affinity, show excellent results in animal models, and can be used to make chimeric mAbs for clinical trials, the problem with humans developing anti-murine antibodies and other pharmacodynamic effects must be resolved. Immunotherapy for mesothelin-expressing cancers can not be fully exploited until human mAb with high affinity against mesothelin on cancer cells are developed.

Due to their low immunogenicity in human patients, fully human mAb are the most desirable antibody format for clinical application (Huls, et al., *Nat Biotechnol* (1999) 17:276-81). An ideal anti-mesothelin therapeutic agent involves finding a fully human mAb that binds to mesothelin or CA125 and inhibits their interaction. The present invention provides single-chain variable fragment (scFv) antibody fragments (exemplified by HN1 and HN2) that are specific for tumor-associated mesothelin. Anti-mesothelin human antibodies can be isolated from a human scFv phage display library and converted into intact, fully human IgG1 mAb. The antibodies described herein bind specifically to cell surface-associated mesothelin on human mesothelioma and ovarian cancer cells with high affinity and kills cancer cells with very strong antibody-dependent cell-mediated cytotoxicity (ADCC). Immuntoxins that utilize the present antibodies as a targeting moiety kill mesothelin-expressing cancer cells with high cytotoxic activity. In addition, the antibodies described herein functionally block the mesothelin-CA125 interaction on cancer cells. The antibodies provided herein find use for mesothelin-expressing cancer treatment and diagnosis.

In the context of treatment, the antibodies of the invention can be used alone, to mediate ADCC, or as a targeting moiety in an immunotoxin. Immunotoxins are chimeric proteins composed of an antibody or antibody fragment moiety and an effector or therapeutic moiety, e.g., a cytotoxin. For example, an immunotoxin can comprise Fv portion of an antibody fused to a 38 kDa fragment of *Pseudomonas* exotoxin A (this truncated form is referred to as "PE38"). SS1(dsFv)-PE38 (also known as "SS1P") is an immunotoxin composed of (i) an antibody fragment reacting with mesothelin and (ii) PE38, for the treatment of mesothelin expressing cancers. SS1P has been shown to specifically kill mesothelin expressing cell lines and to cause regressions of mesothelin expressing tumors in mice (Hassan, R. et al., *Clin Cancer Res* 8:3520-6 (2002); Onda, M. et al., *Cancer Res* 61:5070-7 (2001)). Based on these studies and appropriate safety data, 2 phase I trials with SS1P are being conducted at the National Cancer Institute in patients with mesothelin expressing cancers (Chowdhury, P. S. et al., *Proc Natl Acad Sci USA* 95:669-74 (1998); Hassan, R. et al., *Proc Am Soc Clin Oncol* 21:29a (2002)). In addition, other therapies targeting mesothelin are in preclinical development (Thomas, A. M. et al., *J Exp Med* 200:297-306 (2004)).

The antibodies described herein have the advantage of being created from human germline sequences. The present antibodies can therefore be wholly human and elicit reduced or no immunogenic response when administered to a human. The present antibodies find use to target effector molecules, including drugs (e.g., antineoplastic or chemotherapeutic drugs, as described herein), liposomes loaded with a drug, radionuclides or cytotoxins to cells which express mesothelin on their exterior surface. The present antibodies also find use as reagents for diagnosis, prognosis and detection, for example, in immunohistochemistry and immunoassays. The antibodies provided herein have very high affinity for mesothelin. For example, HN1 has a dissociation constant (Kd) for human mesothelin of about 7.5 nM (in the range of about 1-100 nM, depending on the form of the antibody), while HN2 has a Kd of about 1.5 nM for both human and mouse mesothelin proteins. These binding affinities are comparable to that of the anti-mesothelin antibody SS1, which has the highest affinity to mesothelin that was previously reported, and which is being used as the targeting portion of an immunotoxin currently in clinical trials for treatment of mesothelin-positive tumors.

Further, the antibodies can be prepared and used as fragments, such as Fabs, that retain antigen recognition that can be used as the targeting portion of immunoconjugates. Alternatively, the Fv regions of the antibodies can be recombinantly produced in frame with a toxin moiety to produce the chimeric molecules known as immunotoxins. Typically, immunotoxins for treatment of solid tumors use single chain Fv regions ("scFvs") or disulfide stabilized Fv regions ("dsFvs") since the Fv regions are significantly smaller than whole immunoglobulins, which permits the immunotoxin to better penetrate into the tumor.

The antibodies described herein can be modified without changing their ability to be used for the purposes described above. As an initial matter, it is noted that the antibodies originated from a human single chain Fv (scFV) library by phage display and mammalian cell display panning against recombinant mesothelin-rabbit IgG Fc fusion protein. The antibodies thus have framework regions (regions outside the complementarity determining regions, or "CDRs") and CDRs which are wholly human. Accordingly, the anti-mesothelin antibodies provided herein are preferred for in vivo use, since they have a lower risk of inducing side effects and typically can remain in the circulation longer. Moreover, the framework regions can be altered using methods known in the art, e.g., to another human framework sequence or a framework sequence from another mammalian species, as desired. Since the CDRs of the variable regions determine antibody specificity, the CDRs of the anti-mesothelin antibodies described herein can be grafted or engineered into an antibody of choice to confer specificity for mesothelin upon that antibody.

2. Anti-Mesothelin Antibodies

In some embodiments, the invention provides anti-mesothelin antibodies which have CDRs 1, 2, and 3 of the $V_H$ chain (i.e., SEQ ID NOS:9, 10 and 11, respectively) and CDRs 1, 2, and 3 of the $V_L$ chain (i.e., SEQ ID NOS:12, 13 and 14, respectively) of the HN1 antibody as those CDRs are shown in FIG. 1, the CDRs defined according to ImMunoGeneTics database (IMGT) (See, Lefranc, *Nucleic Acids Res* (2001) 29:207-9). In some embodiments, the invention provides anti-mesothelin antibodies which have CDRs 1, 2, and 3 of the $V_H$ chain (i.e., SEQ ID NOS:15, 16, 17, respectively) and CDRs 1, 2 and 3 of the $V_L$ chain (i.e., SEQ ID NOS:18, 19 and 20, respectively) of the HN2 antibody as those CDRs are shown in FIG. 2, the CDRs defined according to ImMunoGeneTics database (IMGT). In some forms, the VH and VL chains will be linked by a peptide linker, to form a scFv, or may have one or more cysteine residues engineered into the framework region to permit formation of a disulfide bond linking the two chains together. In some embodiments, the scFv has at least 90%, 93%, 95%, 97% or 99% sequence identity to SEQ ID NO:45. In some embodiments, the scFv has an amino acid sequence of SEQ ID NO:45. In some embodiments, the scFv is encoded by a nucleic acid sequence that has at least 90%, 93%, 95%, 97% or 99% sequence identity to SEQ ID NO:46. In some embodiments, the scFv is encoded by a nucleic acid sequence of SEQ ID NO:46.

In other embodiments, the CDRs are defined according to the method of Kabat. In some embodiments, the invention provides an isolated antibody or antibody fragment that binds to mesothelin, the antibody comprising a heavy chain variable domain comprising a CDR1 of SEQ ID NO:39, a CDR2 of SEQ ID NO:40 and a CDR3 of SEQ ID NO:41 and a light chain variable domain comprising a CDR1 of SEQ ID NO:42, a CDR2 of SEQ ID NO:43 and a CDR3 of SEQ ID NO:44 ("an HN1 antibody"), the CDRs defined according to Kabat (See, Kabat, et al., 5$^{th}$ Ed., National Institutes of Health Publication 91-3242, Bethesda, Md., 1991).

Because of the multiplicity of forms in which the variable regions of the HN1 and the HN2 antibodies can be expressed, and to the variants of the antibodies which can be made, for convenience of reference, the discussion herein will sometimes refer to "HN1 antibodies" or "HN2 antibodies". HN1 antibodies or antibody fragments comprise CDRs 1, 2, and 3 of the $V_H$ chain (i.e., SEQ ID NOS:9, 10 and 11, respectively) and CDRs 1, 2, and 3 of the $V_L$ chain (i.e., SEQ ID NOS:12, 13 and 14, respectively) as shown in FIG. 1, the CDRs defined according to IMGT. Alternatively, HN1 antibodies or antibody fragments comprise CDRs 1, 2, and 3 of the $V_H$ chain (i.e., SEQ ID NOS:39, 40, 41, respectively) and CDRs 1, 2, and 3 of the $V_L$ chain (i.e., SEQ ID NOS:42, 43, 44, respectively) as shown in FIG. 1, the CDRs defined according to Kabat. HN2 antibodies or antibody fragments comprise CDRs 1, 2, and 3 of the $V_H$ chain (i.e., SEQ ID NOS:15, 16, 17, respectively) and CDRs 1, 2 and 3 of the $V_L$ chain (i.e., SEQ ID NOS:18, 19 and 20, respectively) as shown in FIG. 2, the CDRs defined according to IMGT.

It is contemplated that the HN1 and HN2 antibodies can be modified in various ways without losing antigen recognition capability. Thus, the invention provides antibodies which specifically bind mesothelin and which have $V_H$ chains with at least 90%, 93%, 95%, 97% or 99% amino acid sequence identity to the sequence of the $V_H$ chain of the HN1 antibody (SEQ ID NO:2) and/or $V_L$ chains with at least 90%, 93%, 95%, 97% or 99% amino acid sequence identity to the sequence of the $V_L$ chain of the HN1 antibody (SEQ ID NO:4). The invention further provides antibodies which specifically bind mesothelin and which have $V_H$ chains with at least 90%, 93%, 95%, 97% or 99% amino acid sequence identity to the sequence of the $V_H$ chain of the HN2 antibody (SEQ ID NO:6) and/or $V_L$ chains with at least 90%, 93%, 95%, 97% or 99% amino acid sequence identity to the sequence of the $V_L$ chain of the HN2 antibody (SEQ ID NO:8).

In some embodiments, the invention provides antibodies which specifically bind mesothelin and which have $V_H$ chains with at least 95% sequence identity to the sequence of the $V_H$ chain of the HN1 antibody (SEQ ID NO:2) and/or $V_L$ chains with at least 95% sequence identity to the sequence of the $V_L$ chain of the HN1 antibody (SEQ ID NO:4). In some embodiments, the invention provides antibodies which specifically bind mesothelin and which have $V_H$ chains with 100% sequence identity to the sequence of the $V_H$ chain of the HN1 antibody (SEQ ID NO:2) and/or $V_L$ chains with 100% sequence identity to the sequence of the $V_L$ chain of the HN1 antibody (SEQ ID NO:4).

In some embodiments, the invention provides antibodies which specifically bind mesothelin and which have $V_H$ chains with at least 95% sequence identity to the sequence of the $V_H$ chain of the HN2 antibody (SEQ ID NO:6) and/or $V_L$ chains with at least 95% sequence identity to the sequence of the $V_L$ chain of the HN2 antibody (SEQ ID NO:8). In some embodiments, the invention provides antibodies which specifically bind mesothelin and which have $V_H$ chains with 100% sequence identity to the sequence of the $V_H$ chain of the HN1 antibody (SEQ ID NO:6) and/or $V_L$ chains with 100% sequence identity to the sequence of the $V_L$ chain of the HN1 antibody (SEQ ID NO:8).

Preferably, the antibodies have a binding constant ($K_D$) that is about 100 nM or less, for example in the range of about 1-100 nM, for example, about 100 nM, 75 nM, 50 nM, 25 nM, 10 nM, 5 nM, 3 nM, 2 nM, 1 nM, or less. Affinity can be measured using any method known in the art. Applicable assays are described herein, e.g., BIAcore analysis. Another applicable assay is provided in U.S. Patent Publication 2009/0047211. Whether or not a modified antibody retains this utility can be readily determined by, for example, conducting one of these tests with the modified antibody and comparing the results to the results of a like test conducted using the HN1 or the HN2 antibody.

The CDRs of the HN1 and HN2 antibodies can also be modified to improve their affinity. Work from the laboratory of the present inventors has established that the affinity of antibodies can be improved by mutating residues encoded by codons in mutational "hotspots," which are nucleotide sequences where mutations are frequently concentrated during the in vivo affinity maturation process. Mutation of residues encoded by a codon with nucleotides within one of two consensus sequences is particularly useful. The two consensus sequences are (1) a tetranucleotide A/G-G-C/T-A/T (Pu-G-Py-A/T), and the serine codons AGY, where Y can be a C or a T (see, Wagner et al., *Nature,* 376:732 (1995); and Goyenechea and Milstein, *Proc. Natl. Acad. Sci. USA* 93:13979-13984 (1996)). The technique for mutating hotspots and selecting antibodies with increased affinity compared to the starting antibody (sometimes called the "parental" antibody) is explained in detail in, for example, PCT/US00/14829, International Publication No. WO 00/73346. Thus, it is contemplated that the affinity of the HN1 or the HN2 antibody, or both, can be improved by mutating residues in their CDRs, which residues are encoded by codons in one of the two consensus hotspot motifs set forth above. For convenience of reference, such residues can be referred to as "hot spot residues".

It is also noted that making a conservative substitution of a CDR residue encoded by a codon whose nucleotides are not within a hot spot motif can often be made without markedly changing the affinity of the resulting antibody (for convenience, such a residue can be referred to as a "non-hot spot residue"). Persons of skill will therefore recognize that antibodies having a CDR with, for example, a single non-hot spot residue mutation compared to the CDRs set forth herein for the HN1 or the HN2 antibody, which have affinities close to those reported for the HN1 or the HN2 antibody, and which have similar efficacy in immunotherapy, immunological assays and immunohistochemical techniques, can be used in the methods of the invention. For purposes of determining whether an antibody has an affinity close to that reported for the HN1 or the HN2 antibody, an antibody having CDRs which have the sequences of those set forth in FIG. 1 or FIG. 2 but in which one or more CDRs have a single non-hot spot residue mutation can be considered to have an affinity close to that reported for the HN1 or the HN2 antibody if its affinity is within 1 nM of that reported herein for the corresponding antibody (e.g., to that of the HN1 antibody if the CDRs are those of the HN1 antibody except for the mutation of the non-hot spot residue and, optionally, of a hot spot residue). For purposes of determining whether an antibody has similar efficacy in immunotherapy, immunological assays and immunohistochemical techniques to that reported herein for the HN1 or the HN2 antibody, an antibody having CDRs which have the sequences of those set forth in FIG. 1 or FIG. 2 but in which one or more CDRs have a single non-hot spot residue mutation can be considered to have an affinity close to that reported for the HN1 or the HN2 antibody if its affinity is within 1 nM of that reported for the corresponding antibody.

Accordingly, in some embodiments, the antibodies have (a) CDRs which have the sequences set forth in FIG. 1 for antibody HN1 or FIG. 2 for antibody HN2, except for one or more mutations of residues encoded by a codon with nucleotides within a consensus sequence selected from A/G-G-C/T-A/T (Pu-G-Py-A/T), and AGY, where Y can be a C or a T, and (b) the same or greater affinity for mesothelin than the starting HN1 or HN2 antibody. In some embodiments, the antibodies have (a) CDRs which have the sequences set forth in FIG. 1 for antibody HN1 or FIG. 2 for antibody HN2, except that one or more of the CDRs have one mutation of residues encoded by a codon with nucleotides that do not fall within a consensus sequence, (b) an affinity for mesothelin that is similar to that of the HN1 or HN2 antibody and (c) similar efficacy when used for immunotherapy, immunoassays or immunohistochemical techniques. In some embodiments, the antibodies have (a) CDRs which have the sequences set forth in FIG. 1 for antibody HN1 or FIG. 2 for antibody HN2 except for one or more mutations of residues encoded by a codon with nucleotides within a consensus sequence selected from A/G-G-C/T-A/T (Pu-G-Py-A/T), and AGY, where Y can be a C or a T, (b) one mutation of a residue encoded by a codon with nucleotides that do not fall within a consensus sequence, (c) an affinity for mesothelin that is similar to that of the HN1 or HN2 antibody and, (d) similar efficacy to that of the HN1 or HN2 antibody when used for immunotherapy, immunoassays or immunohistochemical techniques.

It is expected that some of the antibodies made by mutating residues in hot spots in the CDRs of the HN1 or the HN2 antibodies will have affinities higher than that of the starting antibody. It is not expected that the affinity of these yet-higher affinity antibodies will reach zero, which would reflect a covalent bond between the antibody and the antigen. The affinities of the HN1 antibody and of the HN2 antibody are quite good: the affinity of the HN1 antibody for human mesothelin is about 7.5 nM (in the range of about 1-100 nM, depending on the form of the antibody) while the affinity of the HN2 antibody for human and mouse mesothelin is about 1.5 nM. It is therefore expected that forms of these antibodies in which hot spot residues are mutated can be expected to have affinities stated in tenths of a nM. For purposes of being able to state a lower limit on the affinity on the mutated antibodies, the limit may be stated as 0.05 nM.

The sequences of $V_H$ and $V_L$ chains comprising CDRs 1, 2, and 3 of the $V_H$ and CDRs 1, 2, and 3 of the $V_L$ chain of the HN1 antibody, or which have CDRs 1, 2, and 3 of the $V_H$ and CDRs 1, 2, and 3 of the $V_L$ chain of the HN2 antibody, can also be used as the Fv regions of intact immunoglobulins. Persons of skill are aware that the Fc region of antibodies of different classes, or isotypes (IgG, IgA, IgM, etc.), is relatively invariant, and that the specificity of, for example, an IgG molecule, can be altered by engineering into the IgG a selected Fv region. Accordingly, by grafting onto the Fc region an Fv region or Fv regions of the invention (such as those comprising CDRs 1, 2, and 3 of the $V_H$ and CDRs 1, 2, and 3 of the $V_L$ chain of the HN1 antibody or which have CDRs 1, 2, and 3 of the $V_H$ and CDRs 1, 2, and 3 of the $V_L$ chain of the HN2 antibody), specificity and affinity for mesothelin can be conferred to the immunoglobulin molecule.

The $V_L$ and $V_H$ chains of each antibody can be modified by engineering cysteines into the sequence to facilitate formation of disulfide bonds between the chains of the respective antibodies. A light chain and heavy chain of the variable region of an antibody joined by a disulfide bond between cysteines engineered into the framework region is known as a disulfide-stabilized Fv, or "dsFv." Formation of dsFvs is taught in, for example, Pastan, U.S. Pat. No. 6,558,672, which sets forth a series of positions at which cysteines can be engineered into the framework region to facilitate formation of disulfide bonding between the chains, as well as in FitzGerald et al., International Publication Number WO 98/41641. Materials and methods for constructing dsFvs are set forth in, for example, Kreitman et al., Clin. Cancer Res 6:1476-1487 (2000) and Kreitman et al., Intl J Cancer 81:148-155 (1999). These methods can be used for generation of dsFvs of the HN1 and HN2 antibodies. Typically, the two chains are expressed from separate plasmids in inclusion bodies in a prokaryotic host cell, such as E. coli, and allowed to bond before the protein is purified from the inclusion bodies.

The antibodies of the present invention can also be used to form "chimeric antibodies" comprising the variable domains of the antibodies. The term "chimeric antibody" is used in the art to refer to an engineered antibody construct comprising variable domains of one species (such as mouse, rat, goat, sheep, cow, llama or camel variable domains), which may be humanized or not, and constant domains of another species (such as non-human primate or human constant domains) (for review see Hurle and Gross, Curr. Opin. Biotech. 5:428-433 (1994)). It should be clear that any method known in the art to develop chimeric antibodies or antibody constructs can be used. The present invention also concerns a diabody comprising a variable domain (including one which has been humanized) of an antibody of the invention. The term "diabody" relates to two non-covalently-linked scFv's, which then form a so-called diabody, as described in detail by Holliger et al. Proc. Natl. Acad. Sci. USA 90:6444 (1993) and reviewed by Poljak Structure 2:1121-1123 (1994). It should be clear that any method to generate diabodies, as for example described by these references and by Zhu et al. Biotechnology 14:192-196 (1996), can be used.

In general, even if intact immunoglobulins are made using Fvs of the invention, use of fragments of the intact immunoglobulins that retain antigen recognition, such as an Fab, an Fab', a scFv, a dsFv, or a diabody, is preferred. Many of the recombinant immunotoxins produced from constructs of scFv are one-third the size of IgG-toxin chemical conjugates and are homogeneous in composition. Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin (IT) interacts with non-target tissues and tissues that express very low levels of antigen.

These advantages, however, are offset to some degree by the loss of antigen binding affinity that occurs when IgGs, for example, are converted to scFvs (Reiter et al., Nature Biotechnol. 14:239-1245 (1996)). Increasing affinity has been shown to improve selective tumor delivery of scFvs (Adams et al., Cancer Res. 58:485-490 (1998)), and is likely to increase their usefulness in tumor imaging and treatment. The affinity of the antibodies of the invention, however, is so high that immunoconjugates based on these antibodies are effective in delivering effector molecules to their intended targets. The high affinity of the antibodies of the invention is therefore important and provides an alternative to the use of the SS1 antibody and other high affinity anti-mesothelin antibodies for delivering agents to cells expressing mesothelin, providing the practitioner with more flexibility in the choice of targeting moieties in fashioning immunoconjugates.

Accordingly, in some embodiments, the anti-mesothelin antibody is a recombinant antibody such as a scFv or a disulfide stabilized Fv antibody. Fv antibodies are typically about 25 kDa and contain a complete antigen-binding site with 3 CDRs per heavy and light chain. If the $V_H$ and the $V_L$ chain are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker.

In one embodiment, the antibody is a single chain Fv (scFv). The $V_H$ and the $V_L$ regions of a scFv antibody comprise a single chain which is folded to create an antigen binding site similar to that found in two chain antibodies. Once folded, noncovalent interactions stabilize the single chain antibody. In one embodiment, the scFv is recombinantly produced. The CDRs of the $V_H$ and $V_L$ regions are as depicted for antibody HN1 in FIG. 1 and for antibody HN2 in FIG. 2. Further embodiments of the antibodies are as described herein. One of skill will realize that conservative variants of the antibodies of the instant invention can be made. Such conservative variants employed in scFv fragments will retain critical amino acid residues necessary for correct folding and stabilizing between the $V_H$ and the $V_L$ regions.

In some embodiments of the present invention, the scFv antibody is directly linked to an effector molecule ("EM") through the light chain. However, scFv antibodies can be linked to the EM via its amino or carboxyl terminus.

While the $V_H$ and $V_L$ regions of some antibody embodiments can be directly joined together, one of skill will appreciate that the regions may be separated by a peptide linker consisting of one or more amino acids. Peptide linkers and their use are well-known in the art. See, e.g., Huston, et al., *Proc. Nat'l Acad. Sci. USA* 8:5879 (1988); Bird, et al., *Science* 242:4236 (1988); Glockshuber, et al., *Biochemistry* 29:1362 (1990); U.S. Pat. No. 4,946,778, U.S. Pat. No. 5,132, 405 and Stemmer, et al., *Biotechniques* 14:256-265 (1993), all incorporated herein by reference. Generally the peptide linker will have no specific biological activity other than to join the regions or to preserve some minimum distance or other spatial relationship between them. However, the constituent amino acids of the peptide linker may be selected to influence some property of the molecule such as the folding, net charge, or hydrophobicity. Single chain Fv (scFv) antibodies optionally include a peptide linker of no more than 50 amino acids, generally no more than 40 amino acids, usually no more than 30 amino acids, for example, no more than 20 amino acids in length. In some embodiments, the peptide linker is a concatamer of the sequence Gly-Gly-Gly-Ser (SEQ ID NO:36), for example, about 2, 3, 4, 5, or 6 such sequences. However, it is to be appreciated that some amino acid substitutions within the linker can be made. For example, a valine can be substituted for a glycine.

Methods of making scFv antibodies have been described. See, e.g., Ward, et al. *Nature* 341:544-546 (1989). In brief, mRNA from B-cells is isolated and cDNA is prepared. The cDNA is amplified by well known techniques, such as PCR, with primers specific for the variable regions of heavy and light chains of immunoglobulins. The PCR products are purified by, for example, agarose gel electrophoresis, and the nucleic acid sequences are joined. If a linker peptide is desired, nucleic acid sequences that encode the peptide are inserted between the heavy and light chain nucleic acid sequences. The sequences can be joined by techniques known in the art, such as blunt end ligation, insertion of restriction sites at the ends of the PCR products or by splicing by overlap extension (Chowdhury, et al., *Mol. Immunol.* 34:9 (1997)). After amplification, the nucleic acid which encodes the scFv is inserted into a vector, again by techniques well known in the art. Preferably, the vector is capable of replicating in prokaryotes and of being expressed in both eukaryotes and prokaryotes.

In one embodiment, scFvs are chosen through a phage display library. The procedure described above for synthesizing scFv is followed. After amplification by PCR, the scFv nucleic acid sequences are fused in frame with gene III (gIII) which encodes the minor surface protein gIIIp of the filamentous phage (Marks, et al., *J. Biol. Chem.* 267:16007-16010 (1992); Marks, et al., *Behring Inst. Mitt.* 91:6-12 (1992); and Brinkmann, et al., *J. Immunol. Methods* 182:41-50 (1995)). The phage express the resulting fusion protein on their surface. Since the proteins on the surface of the phage are functional, phage bearing mesothelin-binding antibodies can be separated from non-binding or lower affinity phage by panning or antigen affinity chromatography (McCafferty, et al., *Nature* 348:552-554 (1990)).

scFv that specifically bind to mesothelin are typically found by panning. Panning is done by coating a solid surface with mesothelin and incubating the phage on the surface for a suitable time under suitable conditions. The unbound phage are washed off the solid surface and the bound phage are eluted. Finding the antibody with the highest affinity is dictated by the efficiency of the selection process and depends on the number of clones that can be screened and the stringency with which it is done. Typically, higher stringency corresponds to more selective panning. If the conditions are too stringent, however, the phage will not bind. After one round of panning, the phage that bind to mesothelin coated plates are expanded in *E. coli* and subjected to another round of panning. In this way, an enrichment of 2000-fold occurs in 3 rounds of panning. Thus, even when enrichment in each round is low, multiple rounds of panning will lead to the isolation of rare phage and the genetic material contained within which encodes the sequence of the highest affinity antibody. The physical link between genotype and phenotype provided by phage display makes it possible to test every member of a cDNA library for binding to antigen, even with large libraries of clones.

The antibodies of this invention bind to mesothelin with an affinity at least that of HN1 or of HN2. Binding affinity for a target antigen is typically measured or determined by standard antibody-antigen assays, such as competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is <1 µM, preferably <100 nM or <10 nM, and most preferably <0.1 nM. Antibody molecules will typically have a $K_D$ in the lower ranges. $K_D$=[Ab-Ag]/[Ab] [Ag] where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible non-covalent associations such as electrostatic attraction, Van der Waals forces and hydrogen bonds. This method of defining binding specificity applies to single heavy and/or light chains, CDRs, fusion proteins or fragments of heavy and/or light chains, that are specific for mesothelin if they bind mesothelin alone or in combination.

The antibodies can be detected and/or quantified using any of a number of well recognized immunological binding assays (see, e.g., U.S. Pat. Nos. 4,366,241; 4,376,110; 4,517, 288; and 4,837,168). For a review of the general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (e.g., mesothelin) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the anti-mesothelin antibody. Alternatively, the labeling agent may be a third moiety, such as another antibody, that specifically binds to the antibody/mesothelin protein complex.

In one aspect, a competitive assay is contemplated wherein the labeling agent is a second anti-mesothelin antibody bearing a label. The two antibodies then compete for binding to the immobilized mesothelin. Alternatively, in a non-competitive format, the mesothelin antibody lacks a label, but a second antibody specific to antibodies of the species from which the anti-mesothelin antibody is derived, e.g., murine, and which binds the anti-mesothelin antibody, is labeled.

Other proteins capable of specifically binding immunoglobulin constant regions, such as Protein A or Protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401-1406 (1973); and Akerstrom, et al., *J. Immunol.* 135:2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting anti-mesothelin antibodies in a sample containing the antibodies generally comprises the steps of contacting the sample with an antibody which specifically reacts, under immunologically reactive conditions, to the mesothelin/antibody complex.

In some embodiments, the antibodies or antibody fragments of the invention are fully human, i.e., are encoded by nucleic acids that correspond to a human germline sequence. Techniques for producing human monoclonal antibodies are known in the art, and described, e.g., in Lonberg, *Handb Exp Pharmacol* (2008) 181:69-97; Lonberg, *Curr Opin Immunol* (2008) 20(4):450-9; Lanzavecchia, et al., *Curr Opin Biotech* (2007) 18(6):523-8; and Weiner, *J Immunother* (2006) 29(1): 1-9. Anti-mesothelin monoclonal human antibodies can be isolated by screening phage displays from libraries of variable region heavy and light chains encoded by nucleic acid sequences that correspond to human germline sequences for heavy and light chain combinations that bind to mesothelin, as described herein.

3. Production of Immunoconjugates

The anti-mesothelin antibodies of the invention can be linked to effector molecules (EM) through the EM carboxyl terminus, the EM amino terminus, through an interior amino acid residue of the EM such as cysteine, or any combination thereof. Similarly, the EM can be linked directly to heavy, light, Fc (constant region) or framework regions of the antibody. Linkage can occur through the antibody's amino or carboxyl termini, or through an interior amino acid residue. Further, multiple EM molecules (e.g., any one of from 2-10) can be linked to the anti-mesothelin antibody and/or multiple antibodies (e.g., any one of from 2-5) can be linked to an EM. The antibodies used in a multivalent immunoconjugate composition of the present invention can be directed to the same or different mesothelin epitopes.

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various anticancer drugs known in the art, including vinblastine, daunomycin and the like, cytotoxins such as native or modified *Pseudomonas* exotoxin or Diphtheria toxin, encapsulating agents, (e.g., liposomes) which themselves contain pharmacological compositions such as doxorubicin or other drugs, radioactive agents such as $^{125}I$, $^{32}P$, $^{14}C$, $^3H$ and $^{35}S$ and other labels, target moieties and ligands.

Exemplary cytotoxins include *Pseudomonas* exotoxins, Diphtheria toxins, ricin, and abrin. *Pseudomonas* exotoxin and Diphtheria toxin are most preferred. Suitable *Pseudomonas* exotoxin variants for use in delivery to tumor cells are well known in the art and described, for example, in U.S. Pat. Nos. 4,545,985; 5,458,878; 5,602,095; 5,705,163; 5,980,895; 6,074,644; 6,423,513; 6,426,075 and 6,518,061. In some embodiments, the effector moiety is *Pseudomonas* exotoxin, PE38.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458, 066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (3RD ED.), Vols. 1-3, Cold Spring Harbor Laboratory (2001)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987-2009). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native EM or anti-mesothelin antibodies can be modified to form the EM, antibodies, or immunoconjugates of the present invention. Modification by site-directed mutagenesis is well known in the art. Nucleic acids encoding EM or anti-mesothelin antibodies can be amplified by in vitro methods Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, immunoconjugates are prepared by inserting the cDNA which encodes an anti-mesothelin scFv antibody into a vector which comprises the cDNA encoding the EM. The insertion is made so that the scFv and the EM are read in frame, that is in one continuous polypeptide which contains a functional Fv region and a functional EM region. In one embodiment, cDNA encoding a diphtheria toxin fragment is ligated to a scFv so that the toxin is located at the carboxyl terminus of the scFv. In a most preferred embodiment, cDNA encoding PE is ligated to a scFv so that the toxin is located at the amino terminus of the scFv.

Once the nucleic acids encoding an EM, anti-mesothelin antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including E. coli, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For E. coli this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for E. coli and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-mesothelin antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the immunoconjugates, EM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. J. Am. Chem. Soc. 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithio-erythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

4. Therapeutic Moieties and Detectable Labels

In some embodiments, the antibodies of the invention can be coupled to therapeutic moieties or to detectable labels. When the therapeutic moiety is a cytotoxin, the resulting chimeric molecule is referred to as an immunotoxin. Exemplary toxins include *Pseudomonas* exotoxin A, ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060,165).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin ("PE"). The term "*Pseudomonas* exotoxin" as used herein refers to a PE that has been modified from the native sequence to reduce or to eliminate non-specific binding. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:37) and REDL (SEQ ID NO:38). See Siegall, et al., *J. Biol. Chem.* 264:14256-14261 (1989). In a preferred embodiment, the cytotoxic fragment of PE retains at least 50%, preferably 75%, more preferably at least 90%, and most preferably 95% of the cytotoxicity of native PE when delivered to a cell bearing mesothelin. In a most preferred embodiment, the cytotoxic fragment is more toxic than native PE.

Native *Pseudomonas* exotoxin A ("PE") is an extremely active monomeric protein (molecular weight 66 kD), secreted by *Pseudomonas aeruginosa*, which inhibits protein synthesis in eukaryotic cells. The native 613 amino acid sequence of PE is provided in U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., (1989), supra.

The term "PE" as used herein includes cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments and variants of PE have been investigated for years as agents for clinical use; several of these fragments and variants are described below. For convenience, residues of PE which are deleted or mutated are typically referred to in the art by their position in the 613 amino acid sequence of native PE. As noted, the 613-amino acid sequence of native PE is well known in the art.

In preferred embodiments, the PE has been modified to reduce or eliminate non-specific cell binding. Frequently, this is achieved by deleting domain Ia. as taught in U.S. Pat. No. 4,892,827, although it can also be achieved by, for example, mutating certain residues of domain Ia. U.S. Pat. No. 5,512, 658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as "PE4E".

One derivative of PE in which Domain Ia is deleted has a molecular weight of 40 kDa and is correspondingly known as PE40. See, Pai, et al., *Proc. Nat'l Acad. Sci. USA* 88:3358-62 (1991); and Kondo, et al., *J. Biol. Chem.* 263:9470-9475 (1988). PE35 is a 35 kD carboxyl-terminal fragment of PE in which amino acid residues 1-279 have deleted and the molecule commences with a methionine residue at position 280, followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 is a truncated PE pro-protein composed of PE amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)). In some embodiments, the lysine residues at positions 590 and 606 of PE in PE38 are mutated to glutamines, while the lysine at position 613 is mutated to arginine, to create a form known as "PE38QQR." See, e.g., Debinski and Pastan, Bioconj. Chem., 5: 40-46 (1994). This form of PE was originally developed in the course of increasing the homogeneity of immunotoxins formed by chemically coupling the PE molecules to the targeting antibodies.

Further, several means are known for increasing the cytotoxicity of PE by altering residues in domain III from the native sequence. Studies have determined that certain amino acid sequences and repeats of these sequences could be used in place of the native sequence of residues 609-613 of PE to increase the cytotoxicity of the resulting PE compared to PE made with the native sequence (the native sequence of residues 609-613 and specific mutations that increase cytotoxicity are discussed in more detail below in the section entitled "*Pseudomonas* exotoxin A". More recently, it has been determined that a substitution of glycine, alanine, valine or other residues for the arginine present at position 490 of the native PE sequence would increase cytotoxicity, with substitution of the arginine by alanine being particularly advantageous. See, e.g., U.S. Published Patent Application 2007/0189962; Bang et al., *Clin Cancer Res*, 11:1545-1550 (2005). While PEs of the invention using the native domain III sequence are expected to be useful by themselves, if desired the cytotoxicity of the PE can be augmented by using one or more of these substitutions or mutations. Any particular substitution or mutation can be tested to determine whether it retains adequate cytotoxicity for in vitro use and whether it has sufficiently low non-specific toxicity for in vivo use using assays known in the art, including those described in WO 2009/032954.

In some embodiments, the PE toxin is modified to remove epitopes recognized by T cells and/or B cells. The presence of epitopes or subepitopes have been mapped in domain III. Binding of antibodies which recognize those epitopes can be reduced or eliminated by substitutions of the residues normally present at certain positions. It has been demonstrated that the binding of these antibodies can be reduced by substituting an alanine, glycine, serine or glutamine for one or more amino acid residues selected from the group consisting of D403, R412, R427, E431, R432, R458, D461, R467, R505, R513, E522, R538, E548, R551, R576, K590, and L597 in a PE (the positions are made with reference to native PE; see, e.g., WO 2007/016150, U.S. Published Patent Application 2009/0142341 and WO 2009/032954). In some embodiments, the PE toxin is PE-6X, wherein alanine, glycine or serine residues are substituted in place of amino acid residues R432, R467, R490, R513, E548 and K590, the residue positions corresponding to native PE. In some embodiments, the PE toxin is PE-8X, wherein alanine, glycine or serine residues are substituted in place of amino acid residues D406, R432, R467, R490, R513, E548, K590 and Q592, the residue positions corresponding to native PE. In PE-6× and PE-8X, all of domain I and part or all of domain II may also be removed, for example, as described above for PE35, PE38 and PE40.

Since the presence of these residues prior to their substitution maintains an epitope or subepitope in domain III, for ease of reference, the residues at these positions can be referred to as "maintaining" the immunogenicity of their respective epitopes or subepitopes, while substituting them with alanine or the like reduces the immunogenicity of PE domain III resulting from the native epitope or subepitope. While PEs of the invention using the native domain III sequence are expected to be useful by themselves, therefore, if desired substitutions of one of more of the residues identified above can be made to reduce further the immunogenicity of the PEs of the invention. Any particular substitution or mutation can be tested to determine whether it retains adequate cytotoxicity for in vitro or in vivo use using assays known in the art, including those set forth WO 2009/032954 and in PCT/US2009/046292.

In some embodiments, the PE toxin is modified to remove amino acid segment(s) that are targets of lysosomal proteases, i.e., are lysosomal resistant ("LR"). Exemplary lysosomal resistant variants of PE are described, e.g., in Weldon, et al., *Blood* (2009) 113:3792-3800 and in WO 2009/032954. For example, in some PE-LR cytotoxins, residues 1-273 and 285-394 are removed, the positions corresponding to native PE. In some embodiments, a cytotoxic, lysosomal resistant PE fragment selected from PE25LR, PE35LR, PE38LR or PE40LR is used. In some embodiments, the PE toxin is PE-LR/6X, wherein residues 1-273 and 285-394 are removed and alanine, glycine or serine residues are substituted in place of amino acid residues R432, R467, R490, R513, E548 and K590, the residue positions corresponding to native PE. In some embodiments, the PE toxin is PE-LR/8X, wherein residues 1-273 and 285-394 are removed and alanine, glycine or serine residues are substituted in place of amino acid residues D406, R432, R467, R490, R513, E548, K590 and Q592, the residue positions corresponding to native PE.

As noted above, some or all of domain Ib may be deleted, and the remaining portions joined by a linker or directly by a peptide bond. Some of the amino portion of domain II may be deleted. And, the C-terminal end may contain the native sequence of residues 609-613 (REDLK; SEQ ID NO:55), or may contain a variation found to maintain the ability of the construct to translocate into the cytosol, such as REDL (SEQ ID NO:38) or KDEL (SEQ ID NO:37), and repeats of these sequences. See, e.g., U.S. Pat. Nos. 5,854,044; 5,821,238; and 5,602,095 and WO 99/51643. While in preferred embodiments, the PE is PE4E, PE40, PE38, or PE38QQR, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

In some preferred embodiments, the toxicity of the PE is increased by mutating the arginine (R) at position 490 of the native sequence of PE. The R is mutated to an amino acid having an aliphatic side chain that does not comprise a hydroxyl. Thus, the R can be mutated to glycine (G), alanine (A), valine (V), leucine (L), or isoleucine (I). In preferred embodiments, the substituent is G, A, or I. Alanine is the most preferred. Surprisingly, the mutation of the arginine at position 490 to alanine doubles the toxicity of the PE molecule. The discovery of this method of increasing the toxicity of PE is disclosed in co-owned international application PCT/US2004/039617, which is incorporated herein by reference.

A. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity of PE

*Pseudomonas* exotoxins employed in the invention can be assayed for the desired level of cytotoxicity by assays well known to those of skill in the art. Exemplary toxicity assays are described in, e.g., WO 00/73346, Example 2. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative C. Other Therapeutic Moieties Antibodies of the present invention can also be used to target any number of different diagnostic or therapeutic compounds to cells expressing mesothelin on their surface. Thus, an antibody of the present invention, such as an anti-mesothelin scFv, may be attached directly or via a linker to a drug that is to be delivered directly to cells bearing mesothelin.

Exemplary drugs include drugs commonly used for the chemotherapy of neoplastic diseases (i.e., interchangeably called "anticancer drugs," "antineoplastic drugs," or "chemotherapeutic drugs."). Exemplary chemotherapeutic drugs useful in the treatment of neoplastic diseases include alkylating agents (e.g., nitrogen mustards, ethylenimines and methylmelamines, alkyl sulfonates, nitrosoureas and triazenes), antimetabolites (e.g., folic acid analogs, pyrimidine analogs and purine analogs), and natural anticancer agents (e.g., vinca alkaloids, taxanes, epipodophyllotoxins, captothecins and antibiotics). Exemplary nitrogen mustards include mechlorethamine, cyclophosphamide, ifosfamide, melphalan and chlorambucil. Exemplary antimetabolites include methotrexate, 5-fluorouracil, floxuridine, cytarabine, gemcitabine, 6-mercaptopurine, 6-thioguanine, pentostatin, cladribine and fludarabine. Vinca alkaloids include vinblastine and vincristine. Taxanes include paclitaxel and docetaxel. Epipodophyllotoxins include etoposide and teniposide. Camptothecins include topothecan and irinotecan. Antibiotics include dactinomycin, daunorubicin, doxorubicin, bleomycin, and mitomycin. Additional antineoplastic drugs find use and are known in the art, and described, for example, in Chapter 51 of Brunton, et al., Goodman And Gilman's The Pharmacological Basis of Therapeutics, Eleventh Edition, 2006, McGraw-Hill and in Physicians' Desk Reference, 63$^{rd}$ Edition, 2009, Thomson Reuters.

Therapeutic agents further include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-mesothelin antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., *Pharm. Ther.* 28:341-365 (1985).

D. Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

E. Conjugation to the Antibody

In a non-recombinant embodiment of the invention, effector molecules, e.g., therapeutic, diagnostic, or detection moieties, are linked to the anti-mesothelin antibodies of the present invention using any number of means known to those of skill in the art. Both covalent and noncovalent attachment means may be used with anti-mesothelin antibodies of the present invention.

The procedure for attaching an effector molecule to an antibody will vary according to the chemical structure of the EM. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules, such as those available from Pierce Chemical Company (Rockford Ill.).

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

5. Pharmaceutical Compositions and Administration

The antibody and/or immunoconjugate compositions of this invention are particularly useful for parenteral administration, for example intravenous, intraperitoneal, intrapleural, inhalational, intratumoral administration or administration into a body cavity or lumen of an organ. For example, ovarian malignancies may be treated by intravenous or intratumoral administration or by localized delivery (e.g., intraperitoneal) to the tissue surrounding the tumor. To treat mesotheliomas, pharmaceutical compositions of this invention comprising anti-mesothelin antibodies or antibody fragments can be administered directly into the pleural or peritoneal cavities.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

The anti-mesothelin antibodies can be administered in dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once daily, once weekly once a month or once every 3 to 6 months, as needed. Initial therapy regimes can involve more frequent administrations that are reduced upon observing a positive response to treatment in the patient. In some methods, two or more monoclonal antibodies with different binding specificities are administered simultaneously, in which case the dosage of each antibody administered falls within the ranges indicated. For example, the HN1 epitope overlaps the SS1-binding domain in mesothelin, while HN2 binding does not overlap the SS1-binding domain in mesothelin. Accordingly, pharmaceutical compositions can be prepared suitable for co-administration of HN2 antibodies or antibody fragments with either HN1 and/or SS1 anti-mesothelin antibodies or antibody fragments. In some embodiments, all three of HN1, HN2 and SS1 antibodies or antibody fragments can be co-administered. Antibody is usually administered on multiple occasions.

Intervals between single dosages can be daily, weekly, monthly or yearly. Intervals can also be irregular as indicated by measuring blood levels of antibody to mesothelin in the patient.

In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, e.g., applications during a remission, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

A typical pharmaceutical immunotoxin composition of the present invention for intravenous administration would be about 0.1 to 10 mg per patient per day. Dosages from 0.1 up to about 100 mg per patient per day may be used, particularly if the drug is administered to a secluded site and not into the circulatory or lymph system, such as into a body cavity or into a lumen of an organ. Actual methods for preparing administrable compositions will be known or apparent to those skilled in the art and are described in more detail in such publications as REMINGTON: THE SCIENCE AND PRACTICE OF PHARMACY, 21ST ED., University of the Sciences in Philadelphia (USIP), Lippincott, Williams and Wilkins (2005). As noted in the Background, clinical trials of the anti-mesothelin immunotoxin SS1P are underway, and dosage information from those trials can also be used to guide administration of immunotoxins using antibodies of the present invention. See, Hassan, et al., *Clin Cancer Res.* 2007 Sep. 1; 13(17):5144-9.

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Generally, lower doses are administered initially and incrementally increased until reaching a dose that is efficacious without causing undesirable side effects. Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has been shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is the treatment of malignant cells expressing or overexpressing mesothelin or in the treatment of cancers that are mediated by CA125-mesothelin dependent cell attachment. Exemplary malignant cells include ovarian cancer, mesothelioma, non-small cell lung cancer, lung adenocarcinoma, stomach, squamous cell cancers and pancreatic cancer.

6. Methods of Blocking Mesothelin-CA125-Mediated Cell Attachment

The present antibodies find use in the treatment and prevention of cancers mediated by mesothelin-CA125 binding and/or cancers with tumor cells that express or overexpress mesothelin. Exemplary cancers include ovarian cancer, mesothelioma, non-small cell lung cancer, lung adenocarcinoma and pancreatic cancer.

With respect to therapeutic uses, the anti-mesothelin antibodies and antibody fragments can be administered to an individual with a demonstrated tumor burden or a diagnosis from a qualified clinician of having a cancer mediated by mesothelin-CA125 binding and/or a cancer with tumor cells that overexpress mesothelin (i.e., in comparison to a normal cell of the same tissue type). A therapeutically effective amount of the anti-mesothelin antibodies or antibody fragments described herein is administered to, e.g., reduce tumor burden, inhibit tumor growth or progression, and inhibit or prevent metastasis or migration by a measurable amount according to any method known in the art, e.g., by at least about 10%, 20%, 30%, 50%, 80% or 100%. Efficacy can be measured by comparing treated to untreated individuals or by comparing the same individual before and after treatment. Preferably, the measurable amount is therapeutically relevant or statistically significant. The antibodies can be administered, e.g., as IgG to induce ADCC, or as chimeric molecules or immunoconjugates, delivering a therapeutic moiety that reduces or inhibits cancer cell growth. The antibodies also find use in reducing, inhibiting or blocking binding of mesothelin to CA125.

With respect to prophylactic or preventative uses, the anti-mesothelin antibodies or antibody fragments can be administered to an individual, e.g., with a predisposed risk (e.g, environmental or genetic) to developing a cancer mediated by mesothelin-CA125 binding or mesothelin overexpression, with a surgically reduced tumor burden and/or in a remission from a cancer mediated by mesothelin-CA125 binding and/or a cancer with tumor cells that overexpress mesothelin. An effective amount of the anti-mesothelin antibodies or antibody fragments is administered to, e.g., inhibit tumor growth, recurrence or progression, and inhibit or prevent metastasis or migration of tumor cells by a measurable amount according to any method known in the art, e.g., by at least about 10%, 20%, 30%, 50%, 80% or 100%. Efficacy can be measured by comparing treated to untreated individuals or by comparing the same individual before and after treatment. Preferably, the measurable amount is therapeutically relevant or statistically significant.

Administration of the anti-mesothelin antibodies or antibody fragments can be performed concurrently with currently practiced therapies and preventative strategies for cancers mediated by mesothelin-CA125 binding and/or cancers with tumor cells that overexpress mesothelin. For example, the anti-mesothelin antibody or antibody fragments can be administered while the patient is undergoing chemotherapy or radiation therapy, or in coordination with surgical therapies.

The anti-mesothelin antibodies and antibody fragments described herein find use in disrupting the binding interaction of CA125 to mesothelin, in vitro and in vivo. For carrying out methods of directly blocking the binding of CA125 to mesothelin with the antibodies or antibody fragments of the invention, an amount of the anti-mesothelin antibody or antibody fragment sufficient to inhibit CA125/mesothelin binding, e.g., by at least about 25%, 50%, 75% or 100%, is administered. The ability of the antibodies or antibody fragments to reduce or inhibit binding between mesothelin and CA125 can be measured using any method in the art, for example, standard competition assays, where the ability of an antibody of the invention to compete with CA125 binding to mesothelin is demonstrated, e.g., by labeling either of the antibody or the CA125. The ability of the antibodies or antibody fragments to reduce or inhibit cell migration and/or attachment mediated by CA125 and mesothelin interactions can be measured using any method in the art, for example, standard cell attachment and migration assays. For example, the migration and/or attachment ability of cells expressing mesothelin and/or CA125 is measured in the presence and absence of an antibody of the invention.

The anti-mesothelin antibodies or antibody fragments delivered to the site of CA125/mesothelin binding or a cell surface mesothelin protein can be used to deliver an effector molecule, e.g., a drug, a radionuclide, a cytotoxin, a cytokine, a chemokine, as described herein.

The route of delivery for disrupting CA125-mesothelin interaction or for delivery of an effector molecule in vivo will depend on the type and location of the cancer. As discussed above, several parenteral routes of delivery are appropriate, including intravenously, intraperitoneally, intrapleurally, inhalationally, intrathecally, and intratumorally. Preferred routes for this embodiment deliver the antibody or antibody fragments directly to the site of the tumor. Dosing and disease monitoring can be as described herein.

The antibodies of the invention can be tested for prophylactic and therapeutic efficacy in animals suffering from or predisposed to (e.g., in remission from) a cancer mediated by mesothelin/CA125 interaction. Such animals models are known in the art and include without limitation, human tumor xenograft or metastatic tumor models using human ovarian cancer cells (e.g., OVCAR3 cells (Flessner, et al., *Clin Cancer Res*. (2005) 11(8):3117-25; Belotti, et al., *Cancer Res*. (2003) 63(17):5224-9; Manetta, et al., *Gynecol Oncol*. (1989) 32(3):368-70) or human malignant mesothelioma tumors (Inamoto, et al., *Clin Cancer Res*. (2007) 13(14):4191-200; Schulten, et al., *Cancer Genet Cytogenet*. (2007) 176(1):35-47; Spugnini, et al., *Clin Cancer Res*. (2006) 12(20 Pt 1):6133-43).

ELISA results have shown that the HN1 epitope overlaps the SS1-binding domain in mesothelin, while HN2 binding does not overlap the SS1-binding domain in mesothelin. Accordingly, the HN2 finds use in therapeutic applications to be co-administered with either HN1 and/or SS1 anti-mesothelin antibodies or antibody fragments. In some embodiments, all three of HN1, HN2 and SS1 antibodies or antibody fragments are co-administered.

7. Methods of Disease Monitoring

The invention provides methods of detecting inhibition of mesothelin-CA125 binding in a patient suffering from or susceptible to a cancer mediated by mesothelin-CA125 cell adhesion. The methods are particularly useful for monitoring a course of treatment being administered to a patient using the anti-mesothelin antibodies described herein. The methods can be used to monitor both therapeutic treatment on symptomatic patients and prophylactic treatment on asymptomatic patients. Results from the clinical trials of the anti-mesothelin immunotoxin SS1P can be used to guide for determining the clinical efficacy of immunotoxins using antibodies of the present invention. See, Hassan, et al., Clin Cancer Res. 2007 Sep. 1; 13(17):5144-9.

The monitoring methods entail determining a baseline value of tumor burden in a patient before administering a dosage of an anti-mesothelin antibody or antibody fragment, and comparing this with a value for the tumor burden after treatment, respectively.

With respect to therapies using the anti-mesothelin antibodies or antibody fragments to directly block mesothelin-CA125 interaction or deliver an effector moiety to a cell surface mesothelin protein, a significant decrease (i.e., greater than the typical margin of experimental error in repeat measurements of the same sample, expressed as one standard deviation from the mean of such measurements) in value of the tumor burden signals a positive treatment outcome (i.e., that administration of the anti-mesothelin antibody or antibody fragments has blocked progression of tumor growth and/or metastasis).

In other methods, a control value (i.e., a mean and standard deviation) of tumor burden is determined for a control population or a normal population (e.g., burden=zero). Typically, the individuals in the control population have not received prior treatment. Measured values of the tumor burden in a patient after administering a therapeutic agent are then compared with the control value. A significant decrease in tumor burden relative to the control value (e.g., greater than one standard deviation from the mean) signals a positive treatment outcome. A lack of significant decrease or an increase signals a negative treatment outcome.

In other methods, a control value of tumor burden (e.g., a mean and standard deviation) is determined from a control population of individuals who have undergone treatment with an anti-mesothelin antibody or antibody fragment. Measured values of tumor burden in a patient are compared with the control value. If the measured level in a patient is not significantly different (e.g., more than one standard deviation) from the control value, treatment can be discontinued. If the tumor burden level in a patient is significantly above the control value, continued administration of agent is warranted.

In other methods, a patient who is not presently receiving treatment but has undergone a previous course of treatment is monitored for tumor burden to determine whether a resumption of treatment is required. The measured value of tumor burden in the patient can be compared with a value of tumor burden previously achieved in the patient after a previous course of treatment. A significant increase in tumor burden relative to the previous measurement (i.e., greater than a typical margin of error in repeat measurements of the same sample) is an indication that treatment can be resumed. Alternatively, the value measured in a patient can be compared with a control value (mean plus standard deviation) determined in a population of patients after undergoing a course of treatment. Alternatively, the measured value in a patient can be compared with a control value in populations of prophylactically treated patients who remain free of symptoms of disease, or populations of therapeutically treated patients who show amelioration of disease characteristics. In all of these cases, a increase in tumor burden relative to the control level (i.e., more than a standard deviation) is an indicator that treatment should be resumed in a patient.

The tissue sample for analysis is typically blood, plasma, serum, mucous, tissue biopsy, tumor, ascites or cerebrospinal fluid from the patient. The sample can analyzed for indication of neoplasia or an immune response to mesothelin, particularly the CA125 binding region of mesothelin. The immune response can be determined from the presence of antibodies that specifically bind to mesothelin. Antibodies can be detected in a binding assay to a ligand that specifically binds to the antibodies. Typically the ligand is immobilized. Binding can be detected using a labeled anti-idiotypic antibody. Neoplasia or tumor burden can be detected using any method known in the art, e.g., visual observation of a biopsy by a qualified pathologist, or other visualization techniques, e.g., radiography, ultrasound, magnetic resonance imaging (MRI).

8. Kits and In Vitro Uses

In another embodiment, this invention provides for kits for the detection of mesothelin or an immunoreactive fragment thereof, (i.e., collectively, a "mesothelin protein") in a biological sample. A "biological sample" as used herein is a sample of biological tissue or fluid that contains mesothelin. Such samples include, but are not limited to, tissue from biopsy, sputum, amniotic fluid, blood, and blood cells (e.g., white cells). Biological samples also include sections of tissues, such as frozen sections taken for histological purposes. A biological sample is typically obtained from a multicellular eukaryote, preferably a mammal such as rat, mouse, cow, dog, guinea pig, or rabbit, more preferably from a primate, such as a macaque, chimpanzee, and most preferably from a human.

Kits will typically comprise an anti-mesothelin antibody or antibody fragment of the present invention, the embodiments being as described herein. In some embodiments, the anti-mesothelin antibody or antibody fragment will be an anti-mesothelin Fv fragment, such as a scFv fragment.

In addition the kits will typically include instructional materials disclosing means of use of an antibody of the present invention (e.g. for detection of mesothelial cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting mesothelin in a biological sample generally comprises the steps of contacting the biological sample with an antibody which specifically reacts, under immunologically reactive conditions, to mesothelin. The antibody is allowed to bind to mesothelin under immunologically reactive conditions, and the presence of the bound antibody is detected directly or indirectly. The anti-mesothelin antibody may be used, for example, as the capture antibody of an ELISA, or as a second antibody to bind to mesothelin captured by the capture antibody. In some embodiments, the kits comprise an antibody or antibody fragment pre-bound to a solid support, e.g., a microchip, a microtiter plate or a bead. As is known in the art, the presence of the second antibody is typically then detected.

The antibodies provided herein are useful as diagnostic agents and in in vitro assays to detect the presence of mesothelin in biological samples. For example, the antibodies HN1 and HN2 and variants of these antibodies as described herein can be used as the targeting moieties of immunoconjugates in immunohistochemical assays to determine whether a sample contains cells expressing mesothelin. If the sample is one taken from a tissue of a patient which should not normally express mesothelin, detection of mesothelin would indicate either that the patient has a cancer characterized by the presence of mesothelin-expressing cells, or that a treatment for such a cancer has not yet been successful at eradicating the cancer.

In another set of uses for the invention, immunotoxins targeted by antibodies of the invention can be used to purge targeted cells from a population of cells in a culture. Thus, for example, cells cultured from a patient having a cancer expressing mesothelin can be purged of cancer cells by contacting the culture with immunotoxins which use an HN1 antibody or an HN2 antibody (such as scFvs) as a targeting moiety.

Although the present invention has been described in some detail by way of illustration and example for purposes of clarity of understanding, it will be obvious that certain changes and modifications may be practiced within the scope of the appended claims.

EXAMPLES

The following examples are offered to illustrate, but not to limit the claimed invention.

Example 1

Materials and Methods

Cell Culture

OVCAR-3 (ovarian) cells were grown in RPMI 1640 (Dulbecco) supplemented with 20% fetal bovine serum (FBS), 1% penicillin/streptomycin, 1% L-glutamine, and 0.2% human insulin. NCI-H226 (mesothelioma), YOU (mesothelioma), L55 (mesothelioma), EKVX (lung adenocarcinoma), OVCAR-8 (ovarian cancer), Panc3.014 (pancreatic cancer) and A431 (epidermal carcinoma) cell lines were grown in RPMI 1640 (Dulbecco) supplemented with 10% FBS, 1% penicillin/streptomycin, and 1% L-glutamine. HEK 293T cells were grown in 100-mm tissue culture dishes (BD Biosciences, San Jose, Calif.) with Dulbecco's modified Eagle's medium and supplemented with 10% FBS, 1% penicillin/ streptomycin, and 1% L-glutamine. A431/H9 is a transfected A431 cell line stably expressing human mesothelin (Ho, et al., *Clin Cancer Res* (2005) 11:3814-20). G418 (700 μg/ml) was added to all of the cultures of the A431/H9 cell line.

Selection of Anti-Mesothelin Human scFv

The scFv HN1 was selected from a previously reported phage display library of human scFv (Vaughan, et al., *Nat Biotechnol* (1996) 14:309-14). The phage library was subjected to three rounds of panning on Nunc immunotubes (Maxisorp, Thermo Fisher Scientific, Rochester, N.Y.) following an established protocol (Ho, et al., *Methods Mol Biol* (2009) 525:293-308). The rabbit IgG Fc-human mesothelin (rFc-mesothelin) fusion protein was prepared as described (Kaneko, et al., *J Biol Chem* (2009) 284:3739-49). Immunotubes (Maxisorb, Nunc/Thermo Fisher Scientific, Rochester, N.Y.) were coated with rFc-mesothelin overnight at 4° C. using 1 ml of 5 μg/ml protein in phosphate buffered saline (PBS) (10 mM phosphate/150 mM NaCl, pH 7.4) for the first round, 1 μg/ml for the second and the third rounds of panning. The immunotubes were blocked with Blotto (4% skimmed milk in PBS) for 1 h at room temperature and then about $10^{12}$-$10^{13}$ cfu scFv-phage were added into the immunotube in 2% skimmed milk/2% bovine serum albumin (BSA) in PBS. After 2 h of incubation with rocking at room temperature, the unbound and nonspecifically bound scFv-phage were removed using 10 washes with PBS/0.1% Tween-20 and 10 washes with PBS. The specifically bound scFv-phage was eluted with 1 ml elution buffer (100 mM HCl, adjusted to pH 2.2 with solid glycine and containing 0.1% BSA) for 10 min at room temperature. The eluate was neutralized with 60 µl of 2 M Tris base and was used to infect freshly prepared *E. coli* TG1 cells. The scFv-phage were then amplified and rescued for the next round of panning. Ninety-six randomly picked clones at the end of each round of panning were analyzed for mesothelin binding by phage ELISA.

Construction and Production of a Fully Human Anti-Mesothelin mAb

The VH region encoding scFv HN1 was PCR amplified using the forward primer VH-HN1-F (gaggaggaa GAGCTCACTCC CAGGTCCAGCTGGTGCAGTCTGG (SEQ ID NO:58), bold uppercase corresponds to upstream VH sequence, with the internal SacI restriction enzyme site underlined) and the reverse primer VH-HN1-R (gaggaggaa GGGCCCTTGGTGGAGGC ACTCGAGACGGTGAC-CAGGGTTC (SEQ ID NO:59), bold uppercase corresponds to downstream VH sequence, with the internal ApaI restriction enzyme site underlined). The PCR product was digested with SacI and ApaI before being inserted into the expression vector PIGG (Rader, et al., *FASEB J* (2002) 16:2000-2) pre-digested with the same enzymes. The VL region was PCR amplified using the forward primer VL-HN1-F (gaggaggaa AAGCTTGTTGCTCTGGATCTCTGGTGCCTACGGG GACATCCAGATGACCCAGTCTCC (SEQ ID NO:60), bold uppercase corresponds to upstream VL sequence, with the internal HindIII restriction enzyme site underlined) and the reverse primer VL-HN1-R (gaggaggag CGTACGTTTGATCTCCAGCTTGGTCC (SEQ ID NO:61), bold uppercase corresponds to downstream VL sequence, with the internal BsiWI restriction enzyme site underlined). The VL PCR product was also cloned into the expression vector that already harbors the VH gene. The final resulting construct (named pMH119) was then expressed in HEK-293F cells (Invitrogen, Carlsbad, Calif.). Using 293fectin, 30 µg of pMH119 plasmid was transiently transfected into $3 \times 10^7$ HEK-293F cells and kept in 30 mL of FreeStyle serum-free medium (Invitrogen) in a 125-mL spinner flask on a stirring platform at 75 rpm (CELLSPIN system; Integra, Chur, Switzerland) in a humidified atmosphere containing 8% $CO_2$ at 37° C. After three days, the medium was collected after centrifugation, replaced for an additional 3-4 days, and collected again. Pooled supernatants were then processed and antibody was purified using a 1-mL recombinant Protein A Hi-Trap column (GE Healthcare, Piscataway, N.J.) as described (Kaneko, et al., *J Biol Chem* (2009) 284:3739-49). The quality and quantity of purified IgG1 was determined by SDS-PAGE and A280 absorbance on a Nanodrop (Thermo Scientific/Nanodrop, Wilmington, Del.).

Construction and Expression of Immunotoxin scFv from selected phagemids were PCR-amplified using appropriate primers that introduced NdeI and HindIII restriction sites. The products of the reaction were purified, digested with NdeI and HindIII, and cloned into a T7 expression vector (pRB98) in which the scFv was fused to a truncated version of PE38. The expression and purification of recombinant immunotoxins was performed as described previously (Ho, et al., *J Biol Chem* (2005) 280:607-17).

Flow Cytometry

To determine binding of HN1 to mesothelin on the cell surface, cancer cells were grown until confluent, detached by trypsin, and then incubated with 5 µg/ml of the HN1 IgG in fluorescence-activated cell sorting (FACS) buffer (5% BSA, 0.01% NaN3) for 1 h on ice. Bound antibodies were detected by incubating with a 1:200 dilution of goat anti-human IgG-PE (Invitrogen/BIOSOURCE, Carlsbad, Calif.) secondary antibody in FACS buffer for 0.5 h on ice. Cells were analyzed using FACSCalibur (BD Biosciences).

In inhibition assays, cells were incubated with FLAG-tagged mesothelin (1 µg/mL) and an excess amount (10-fold) of the HN1 IgG (10 µg/mL) for 1 h on ice. Bound FLAG-tagged mesothelin proteins were detected by incubating with a 1:100 dilution of an anti-FLAG tag Alexa 488 conjugate (Invitrogen).

Sandwich ELISA

Nunc MaxiSorp 96-well flat-bottomed plates were incubated overnight with 5 µg/ml goat anti-rabbit IgG (Jackson ImmunoResearch Laboratories, West Grove, Pa.) in PBS, followed by an overnight block with 5% BSA, 0.01% NaN3 in PBS. Purified rFc mesothelin fragments (Kaneko, et al., *J Biol Chem* (2009) 284:3739-49) were diluted to 1 µg/ml in ELISA buffer (0.01% Tween 20, 10% Pierce SuperBlock) and incubated on a plate for 1 h at room temperature. Plates were then incubated with biotinylated (ChromaLink Biotin labeling kit, SoluLink, San Diego, Calif.) HN1 IgG or SS1P for 1 h at room temperature. To detect bound HN1 a 1:5000 dilution of streptavidin horseradish peroxidase conjugate (Invitrogen/BIOSOURCE) was added for 1 h at room temperature. The plates were washed four times with ELISA buffer between each coating. Visualization was achieved with 3,3', 5,5'-tetramethylbenzidine detection reagent (KPL, Gaithersburg, Md.) and absorbance was read at 450 nm with a SpectraMax Plus plate reader (Molecular Devices, Sunnyvale, Calif.).

Biosensor Analysis

Binding experiments were performed on a BIACORE T100 instrument (GE Healthcare, Piscataway N.J.). Protein A/G was immobilized onto carboxymethyl 5' dextran surface (CM5 sensor chip, GE Healthcare) by amine coupling providing about 2500 RU surfaces or in some experiments HN1 mAb was amine coupled directly to the CM5 chip (about 350 RU). Hepes buffer (pH-7.4) is used as the running buffer. The rFc-mesothelin (20 µg/mL) was captured on the CM5 sensor chip using a manual injection targeting about 500 RU density. HN1 and HN2 were serially diluted in running buffer to the concentrations (15-250 nM) for kinetic titration (Karlsson, et al., *Anal Biochem* (2006) 349:136-47) and injected at 25° C. at a flow rate of 10 µl/min for 2 min and a 5-min dissociation after the last sample injection. Dilutions of rFc-mesothelin (15-250 nM) were serially injected over the amine coupled HN1 mAb. In order to subtract any background noise from each data set, all samples were also run over a 2500 RU surface of protein A/G (or activated and blocked surface in the case of HN1 mAb surface) to provide a reference surface. Data were fit to a simple 1:1 interaction model, a heterogeneous ligand model or a two state binding model using the global data analysis software provided by GE Healthcare (Biaevaluation 4.1).

Cytotoxicity Assays

Cytotoxicity on cell lines was measured by cell death assays. Cells were plated in 96-well plates at a concentration of $5 \times 10^4$ cells/100 µl/well. Immunotoxins were serially diluted in PBS, 0.2% human serum albumin, and 20 µl was added to each well. Plates were incubated for 72 h at 37° C. Cell death was assessed by WST-8 conversion using the Cell Counting Kit-8 (Dojindo Molecular Technologies, Gaithersburg, Md.); 10 µl of WST-8 (5 mM WST-8, 0.2 mM 1-methoxy-5-methylphenazinium methylsulfate, and 150 mM NaCl) was added to each well, and the incubation was carried out for 4 h at 37° C. The absorbance was measured at 450 nm with a reference wavelength of 650 nm. Cytotoxicity was expressed as 50% inhibition of cell viability, which is halfway between the level of viability in the absence of toxin and that in the presence of 10 µg/ml of cycloheximide. All experiments were performed in triplicate on two or three separate occasions. Statistical analyses were performed with Prism (version 3.02) for Windows (GraphPad software, San Diego, Calif.). Within each cell line, raw data was analyzed by application of one factor (treatment) repeated measures analysis of variance with Dunnett's and Student-Newman-Keuls post-tests. p values less than 0.01 were considered statistically significant.

ADCC

Target and control cells were detached from culture dishes with trypsin and transferred to round-bottom 96-well plates ($1 \times 10^4$ cells per well). For ADCC assays, target or control cells were preincubated with the antibody (10 µg/mL in DMEM medium containing 10% FBS) for 1 h on ice, then mixed with equal volume of peripheral blood lymphocytes (PBL, $1 \times 10^6$ cells per well) and incubated at 37° C. for 22 h. The assays were performed in 5 repeats in a final volume of 200 µl. Controls included target cells incubated in the absence of effector cells, or in the presence of either serum or antibody alone. Tumor cells lysis was determined by measuring the release of lactate dehydrogenase (LDH) using an LDH detection kit (Roche, Mannheim, Germany). ADCC was calculated as the percentage of cytolysis measured in the presence of antibody and PBL, using the maximal LDH release determined by lysis of target cells with 1% Triton X-100 as 100%. Statistical analysis was performed with Prism (version 5) for Windows (GraphPad Software). ADCC raw data were analyzed by analysis of variance with Dunnett's and Newman-Keuls multiple comparison post tests. p values <0.01 were considered statistically significant.

Example 2

Isolation of Human scFv Specific for Mesothelin

A previously reported human scFv phage display library was used to select for binders to mesothelin. Functional antibody Fv fragments from 43 healthy human donors were used to construct a repertoire of $1.4 \times 10^{10}$ scFv fragments displayed on the surface of phage (Vaughan, et al., *Nat Biotechnol* (1996) 14:309-14). The RNA used for the library was prepared from the B-cells of PBL (15 donors), tonsils B-cells (4 donors) and bone marrow (24 donors). The phage library was selected against 10 µg/mL of rFc-mesothelin coated on immunotubes for the first round and then on 1 µg/mL of rFc-mesothelin in the second and third rounds of panning. After the first round of phage panning on the mesothelin protein, about 3000 individual clones were obtained. Five percent of these were mesothelin binders as detected by phage ELISA.

At the end of the third round of selection, more than 90% of clones were mesothelin binders. HN1 and HN2 scFv sequences were highly enriched in the phage clones tested. See, FIGS. 1-4.

The human Fvs (HN1 and HN2) were identified and shown to react with two different epitopes on mesothelin. ELISA results showed that the HN1 epitope overlaps the SS1-binding domain in mesothelin, while HN2 does not overlap the SS1-binding domain in mesothelin. HN1 and HN2 both bound specifically to cell surface-associated mesothelin on mesothelioma and ovarian cancer cells. HN1 and HN2 lysed mesothelin-expressing cancer cells by immunotoxin-mediated cytotoxic activity. HN1 was more active than HN2 on killing cancer cells. HN2 reacted with both human and mouse mesothelin proteins. The results are summarized in Tables 1-3, below, and in FIGS. 8-11.

TABLE 1

Mesothelin Protein Binding (ELISA)

| scFv | Species | Isotype | Human mesothelin-Fc | Mouse mesothelin-Fc |
|---|---|---|---|---|
| HN1 | Human | IgG gamma 1 kappa | +++ | − |
| HN2 | Human | IgG gamma1 lamda | +++ | +++ |

TABLE 2

Mesothelin-Expressing Cell Binding (FACS)

| Cell | Cancer Type | CA125 expression | HN1-PE38 | HN2-PE38 | SS1-PE38 (SS1P) | HA22 |
|---|---|---|---|---|---|---|
| H9 | Recombinant | negative | +++ | ++/+ | +++ | None |
| OVCAR8 | Ovarian | negative | +++ | + | +++ | None |
| OVCAR3 | Ovarian | positive | + | +/− | ++ | None |
| H226 | Mesothelioma | negative | +++ | +/− | +++ | None |
| YOU | Mesothelioma | positive | + | +/− | ++ | None |

TABLE 3

Cytotoxic Assays (WST)

| Cell | Cancer Type | CA125 expression | HN1-PE38 (ng/ml) | HN2-PE38 (ng/ml) | SS1P (ng/ml) | HA22 (ng/ml) |
|---|---|---|---|---|---|---|
| H9 | Recombinant | negative | 0.6-1.2 | 50-60 | 0.4-0.5 | >1000 |
| OVCAR8 | Ovarian | negative | | | | |
| OVCAR3 | Ovarian | positive | | | | |
| H226 | Mesothelioma | negative | 13 | 80 | | >1000 |
| YOU | Mesothelioma | positive | | | | |

Sequence analysis shows that the light chain variable fragment (VL) of HN1 is derived from human κ chain. Interestingly, while it is different from its germline sequence (IGKV1-5*03) and contains several somatic mutations in complementarity determining regions (CDR), the VL sequence of HN1 is the same as those with diverse specificities: 2MR (anti-HIV gp41), CAO79111 and CAO19109 (anti-tetanus toxin), CAD 32240 and CAA12399 (anti β-galactosidase), and AAC98735 (anti-HER3). It may indicate that the key residues for mesothelin binding are mostly located in the heavy chain variable fragment (VH). Surprisingly, among the 18 somatic mutations (not including heavy chain CDR3), 11 somatic mutations are found in conserved heavy chain framework regions, outside conventional CDR. It may indicate that the residues involved in mesothelin binding are not limited to conventional CDR. Phage ELISA shows that the HN1 phage binds to recombinant mesothelin protein produced in *E. coli* (data not shown) as well as rFc-mesothelin, indicating the binding of HN1 to mesothelin is independent of its glycosylation.

Example 3

Engineering of Anti-Mesothelin Immunotoxin and Human IgG

Figure 5B:
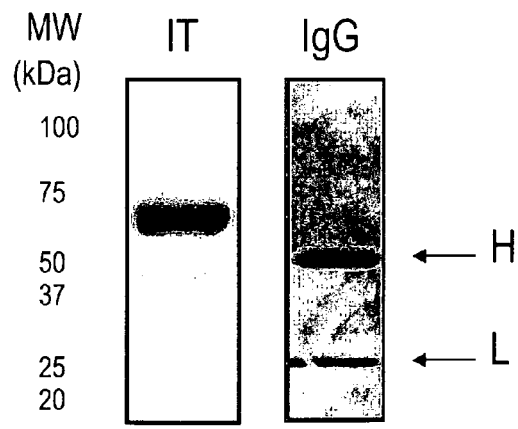
FIG. 5B illustrates an SDS-PAGE analysis. HN1 immunotoxin (IT, 4 μg) and the HN1 whole antibody (IgG, 4 μg) were loaded on the gel. Under reducing conditions, the heavy (H, ~50-kDa) and light chain (L, ~25-kDa) of the HN1 IgG were separated. The purity of the immunotoxin and IgG proteins was greater than 95%.

To investigate its potential as an antibody therapeutic for cancer therapy, the HN1 scFv was converted into two clinically-relevant molecules: an immunotoxin and a fully human IgG (FIG. 5A). To make an anti-mesothelin immuntoxin, the HN1 scFv was fused to a truncated PE38. To engineer a fully human antibody with possible ADCC or CDC, a fully human IgG was generated by fusing the VH into the constant region of heavy chain γ 1 and the VL into the constant region of human κ chain. The final HN1 human IgG molecule is IgGγ1κ. The purity of the immuntoxin and human IgG proteins was above 95% and the correct molecular weights were confirmed by SDS-PAGE (FIG. 5B).

Example 4

Epitope Mapping

Figure 6A:
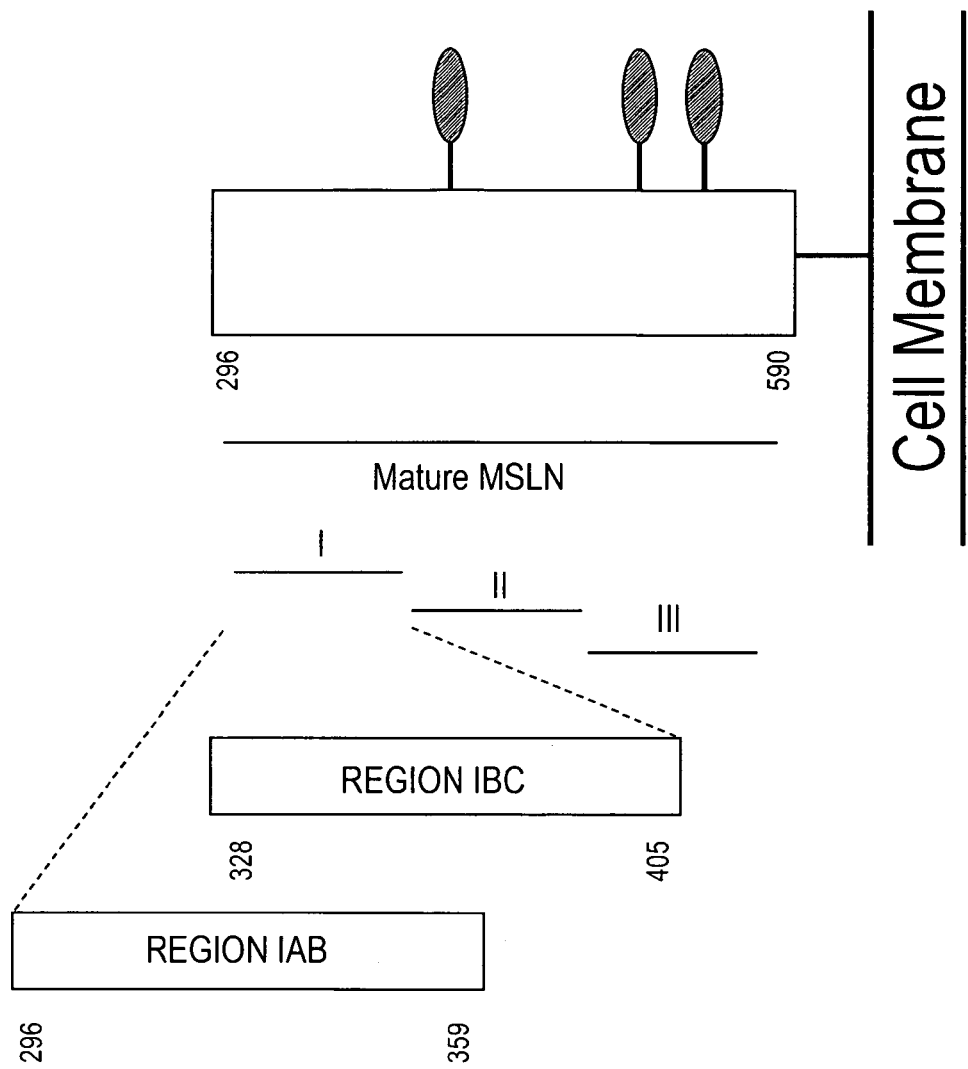
FIG. 6A illustrates membrane-bound mature mesothelin (MSLN) and truncated mutants (Regions I, II, III, IAB, IBC) generated as rabbit Fc fusion proteins were used to identify the epitopes of HN1 and SS1P. Region I: 296-390; Region II: 391-486; Region III: 487-581; Region IAB: 296-359; IBC: 328-405.
Figure 6B:
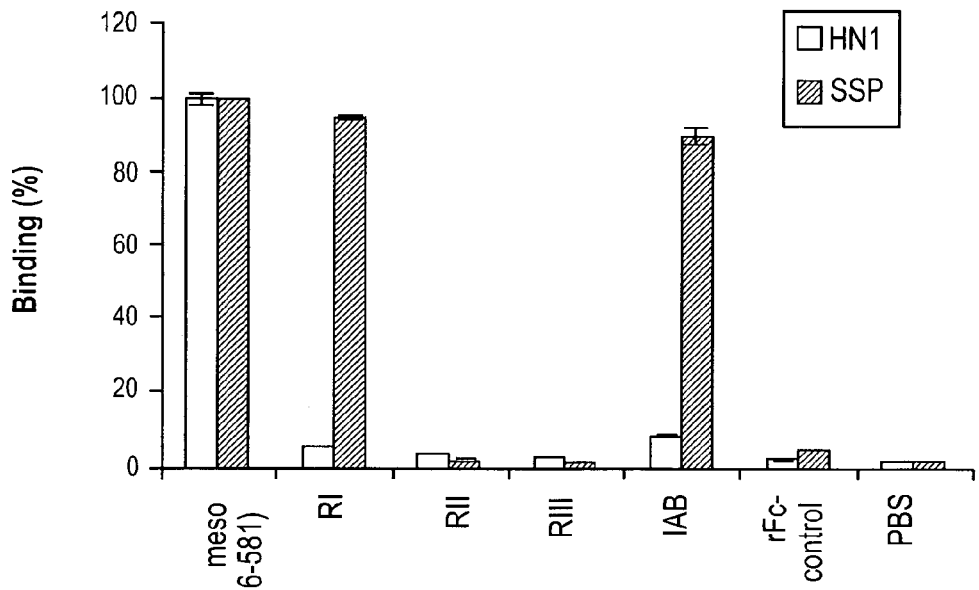
FIG. 6B illustrates binding of HN1 on mesothelin fragments. Biotinylated HN1 or SS1P were tested on the plates capturing mesothelin or its fragments. SS1P binds Region I (296-390), IAB (296-359) and full-length extracellular domain of mesothelin (296-581). HN1 binds only full-length cell surface mesothelin (296-581), not any mesothelin fragments.
Figure 6C:
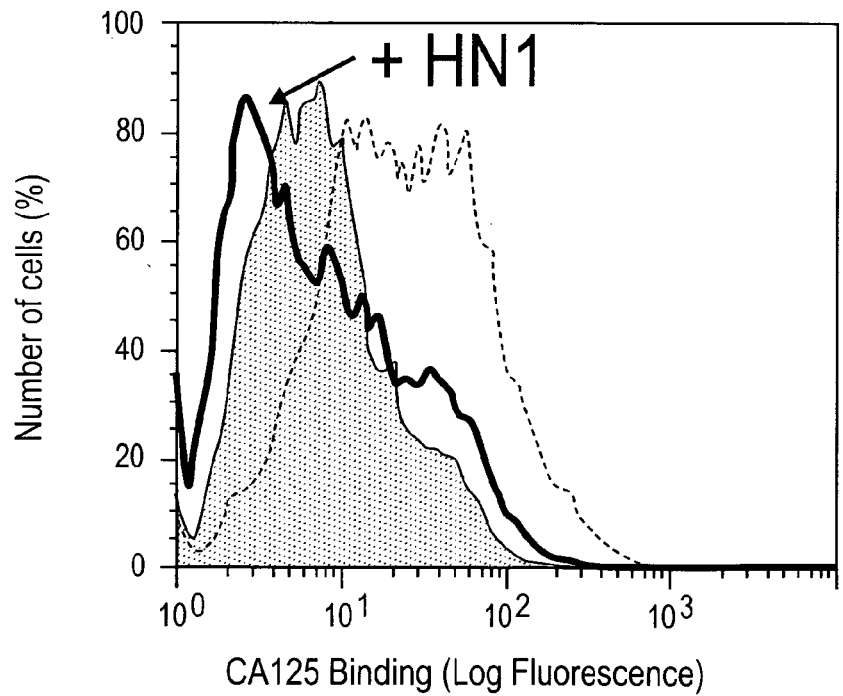
FIG. 6C illustrates inhibition of the mesothelin-CA125 interaction by HN1. OVCAR-3 cells were incubated with HN1 and FLAG-tagged mesothelin as described (see Materials and Methods). The binding of FLAG-mesothelin to CA125 was detected by an anti-FLAG mAb (dotted line). The HN1 IgG (solid line) completely blocks the binding of FLAG-tagged MSLN to CA125 on OVCAR-3 cells. Light gray shaded plot, secondary antibody only.
Figure 8A:
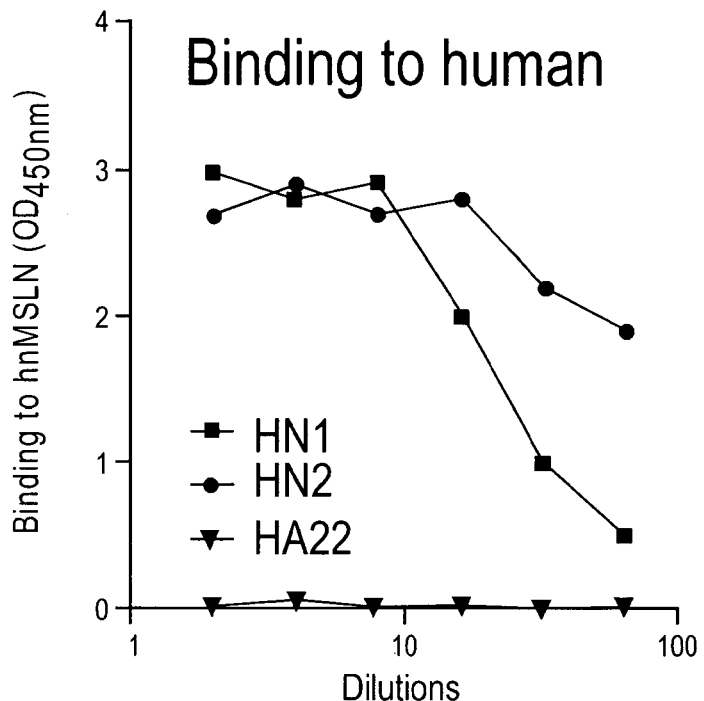
FIGS. 8A-8B. Monoclonal phage scFvs were tested for their binding to immunobilized human mesothelin-Fc fusion (A) or mouse mesothelin-Fc fusion (B) protein by ELISA. A. HN1 and HN2 bound human mesothelin-Fc proteins. B. HN2 bound mouse mesothelin-Fc protein. HN1 and HA22 did not bind mouse mesothelin-Fc protein. HA22, an anti-CD22 scFv, was used as a non-specific control.
Figure 8B:
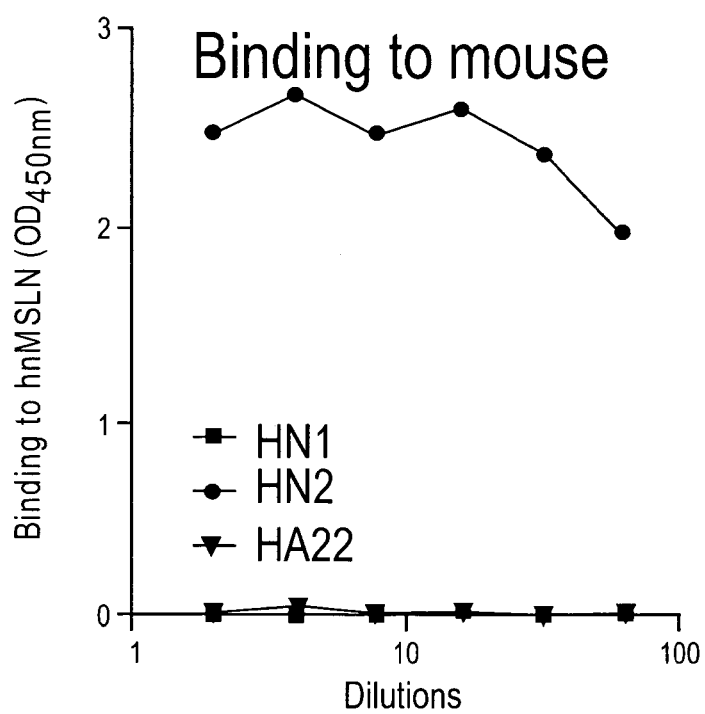

To determine whether HN1 recognizes the same epitope as SS1, an Fv that has been used to make an immunotoxin (SS1P) and a chimeric mouse/human IgG (MORAb-009) currently examined in clinical trials, ELISA was performed using the HN1 human IgG or SS1P on the mesothelin fragments. By displaying the SS1 Fv on human HEK-293 cells that the SS1 Fv bound the Region I (296-390) and IAB (296-359) fragments of mesothelin (Kaneko, et al., *J Biol Chem* (2009) 284:3739-49). Region IAB, the first 64 amino acids at the N-terminus of cell surface mesothelin, contains the SS1 binding site. The present study confirms by ELISA on mesothelin and its fragments that SS1 binds to Regions I and IAB (FIG. 6A). Unlike SS1, HN1 bound only full-length mesothelin but none of the mesothelin fragments, indicating HN1 may bind a discontinuous conformation-sensitive epitope in mesothelin. Our previous study showed that SS1 bound to IAB, the CA125-binding site on mesothelin, and inhibited the mesothelin-CA125 interaction (Kaneko, et al., supra). To determine whether HN1 can block the mesothelin-CA125 interaction, FACS analysis was performed on CA125-expressing ovarian cancer cells (OVCAR-3). Interestingly, as shown in FIG. 6B, the HN1 IgG can completely block the interaction of mesothelin and CA125 interaction on cancer cells. In addition, ELISA experiments have determined that HN1 binds only human mesothelin but not mouse mesothelin (FIG. 8).

Example 5

Binding Affinity

Figure 7A:
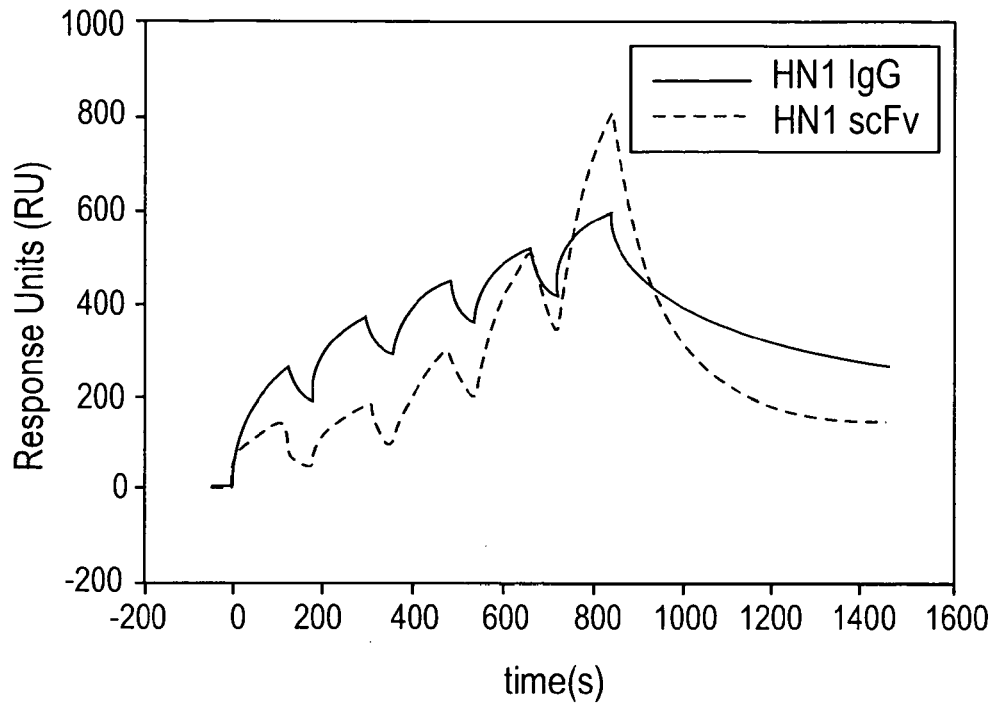
FIGS. 7A-7B illustrates BIAcore analysis of scFv HN1. Binding experiments were performed on a Biacore T100 instrument (see Materials and methods). A. Kinetic titration analysis comparing scFv HN1 to rFc-mesothelin (dashed line) and rFc-mesothelin to HN1 IgG (solid line). B. Data were fit to a simple 1:1 interaction model, heterogeneous ligand model or a two state binding model using the global data analysis provided by GE Healthcare (Biaevaluation 4.1). The binding of scFv HN1 to mesothelin fits two-state binding model.
Figure 7B:
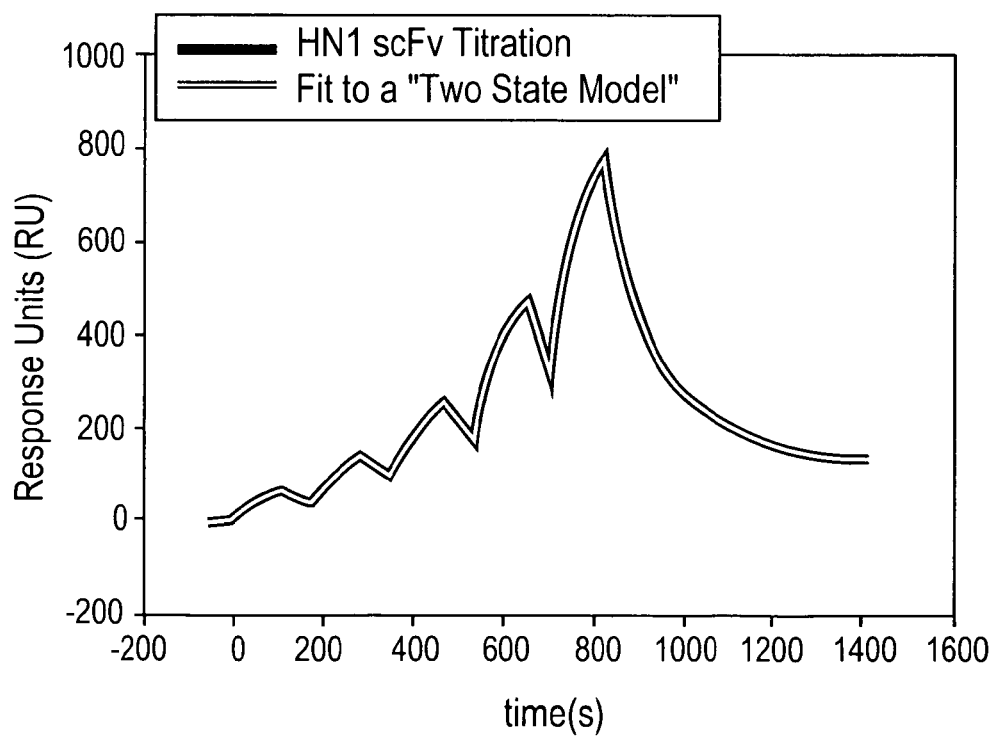

The kinetic association and dissociation rates of HN1 were determined by surface plasmon resonance using a Biacore instrument. Biacore analysis was performed using 1) the monomeric HN1 scFv in the format of an immunotoxin; and 2) the fully human HN1 IgG mAb. Surprisingly, the affinity of the HN1 IgG (KD=3 nM) was over 30-fold better than the scFv molecule (KD=100 nM) (FIG. 7A), primarily attributed to the slower dissociation rate from the HN1 IgG. Further kinetic analysis showed that the binding of scFv HN1 to mesothelin perfectly fits a two-state model, consistent with (but not proving) an induced conformational change in the interaction of HN1 and mesothelin. The Biacore results support a conformation-sensitive structure in human mesothelin to which HN1 binds, as noted above.

Example 6

Binding Properties on Cancer Cells

Figure 9:
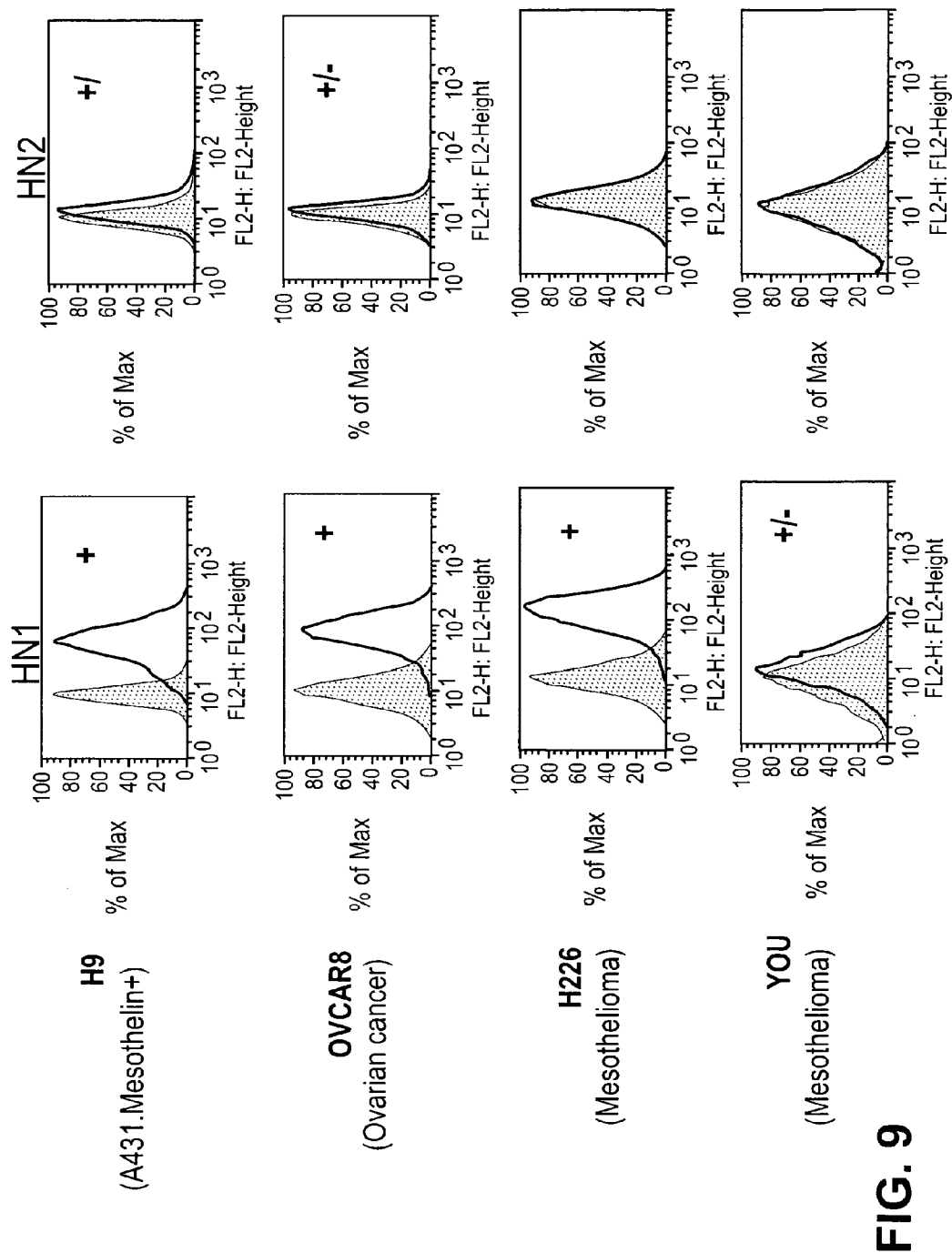
FIG. 9. FACS analysis of human scFvs on mesothelin-expressing cancer cells. The scFv HN1 immunotoxin bound H9, OVCAR8, H226 and YOU cells. HN1 bound H9, OVCAR8 and H226 cells more tightly than YOU cells. HN2 bound H9 and OVCAR8 cells less tightly than HN1. H9: the transfected A431 cell line stably expressing mesothlein; OVCAR8: a human ovarian cancer cell line; H226 and YOU human mesothelioma cell lines.
Figure 10:
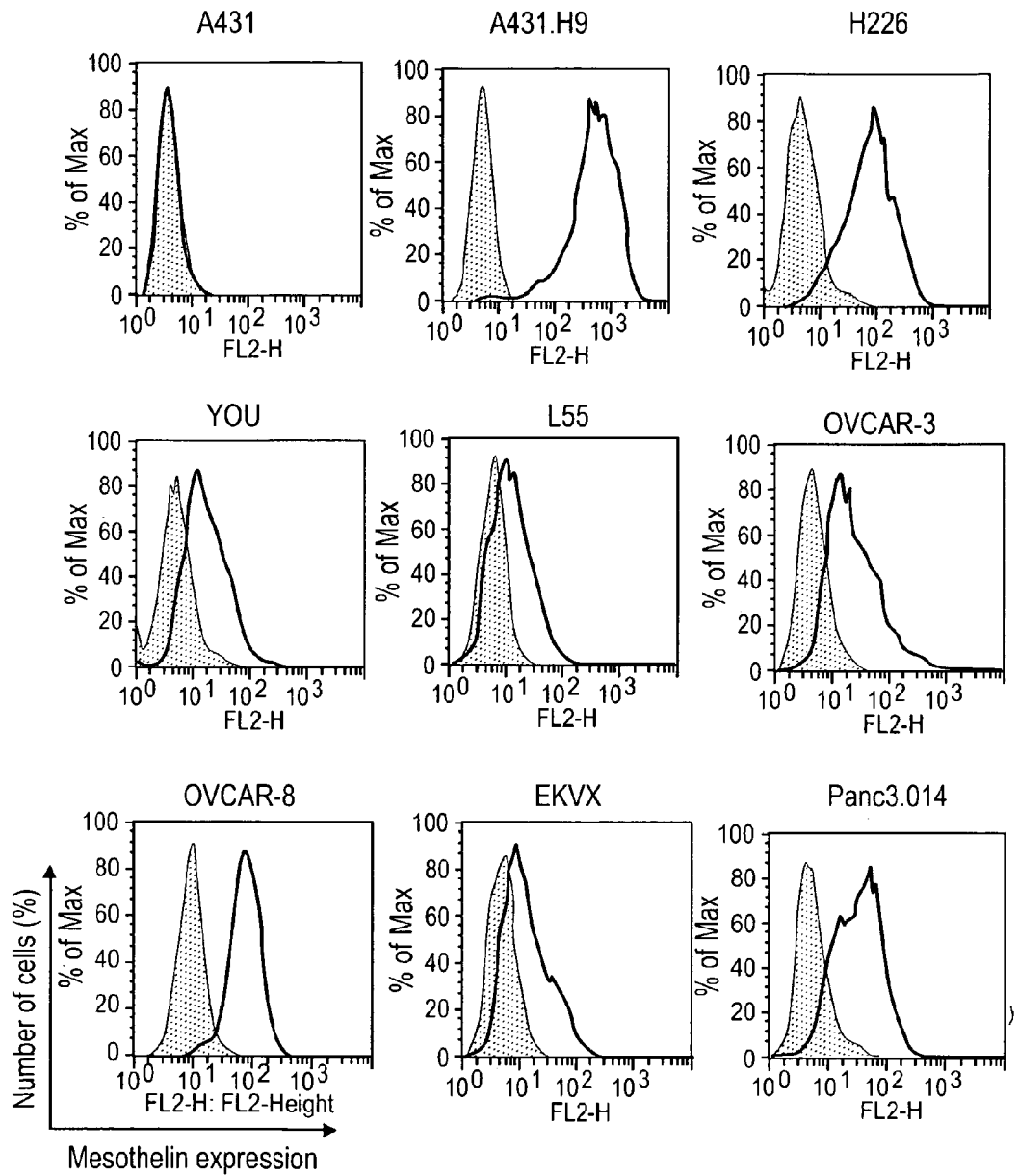
FIG. 10 illustrates FACS analysis of HN1 on mesothelin-expressing cancer cells. The HN1 IgG bound to A431/H9 cells, not A431 cells. HN1 IgG also bound to OVCAR-8, NCI-H226 and YOU cells. A431/H9: the transfected A431 cell line stably expressing mesothelin (Ho, et al., Clin Cancer Res (2005) 11:3814-20); OVCAR-3 and OVCAR-8: human ovarian cancer cell lines; NCI-H226 and YOU: human mesothelioma cell lines; L55 and EKVX: human lung adenocarcinoma cell lines; Panc3.014: a human pancreatic cancer cell line.

To determine whether or not HN1 binds native mesothelin molecules on human tumor cells, flow cytometric analysis was performed on a panel of mesothelin-expressing cancer cells using both HN1-derived immuntoxins and IgG molecules (FIGS. 9 and 10). As a control experiment, HN1 binding to A431/H9 but not A431 is shown, indicating the binding of HN1 on cell surface-associated mesothelin is highly specific. A431/H9 is an A431 cell line stably overexpressing human mesothelin (Ho, et al., *Clin Cancer Res* (2005) 11:3814-20). The binding of HN1 on human tumor cells was then studied. The assays showed that HN1 strongly bound mesothelioma (NCI-H226, YOU and L55), ovarian cancer (OVCAR-3 and OVCAR-8), lung adenocarcinoma cells (EKVX) and pancreatic (Panc3.014) cell lines. The binding signals are related to the mesothelin expression levels on these cell lines. The number of the mesothelin sites per cell was measured by flow cytometry (Ho, et al., *Clin Cancer Res* (2007) 13:1571-5). A431/H9 cells have $1.5 \times 10^6$ recombinant mesothelin sites per cell. NCI-H226, a cell line originally established from a pleural mesothelioma patient, has the highest ($>1 \times 10^5$) number of the native mesothelin sites per cell among all the seven human cancer cell lines tested. Most other cancer cell lines have less than 50,000 sites per cell. The HN1 antibody was able to bind to cancer cells (e.g., OVCAR-3) with as little as 12,000 sites per cell.

Example 7

Functional Characteristics of Anti-Mesothelin Immunotoxin and Human IgG

Figure 11:
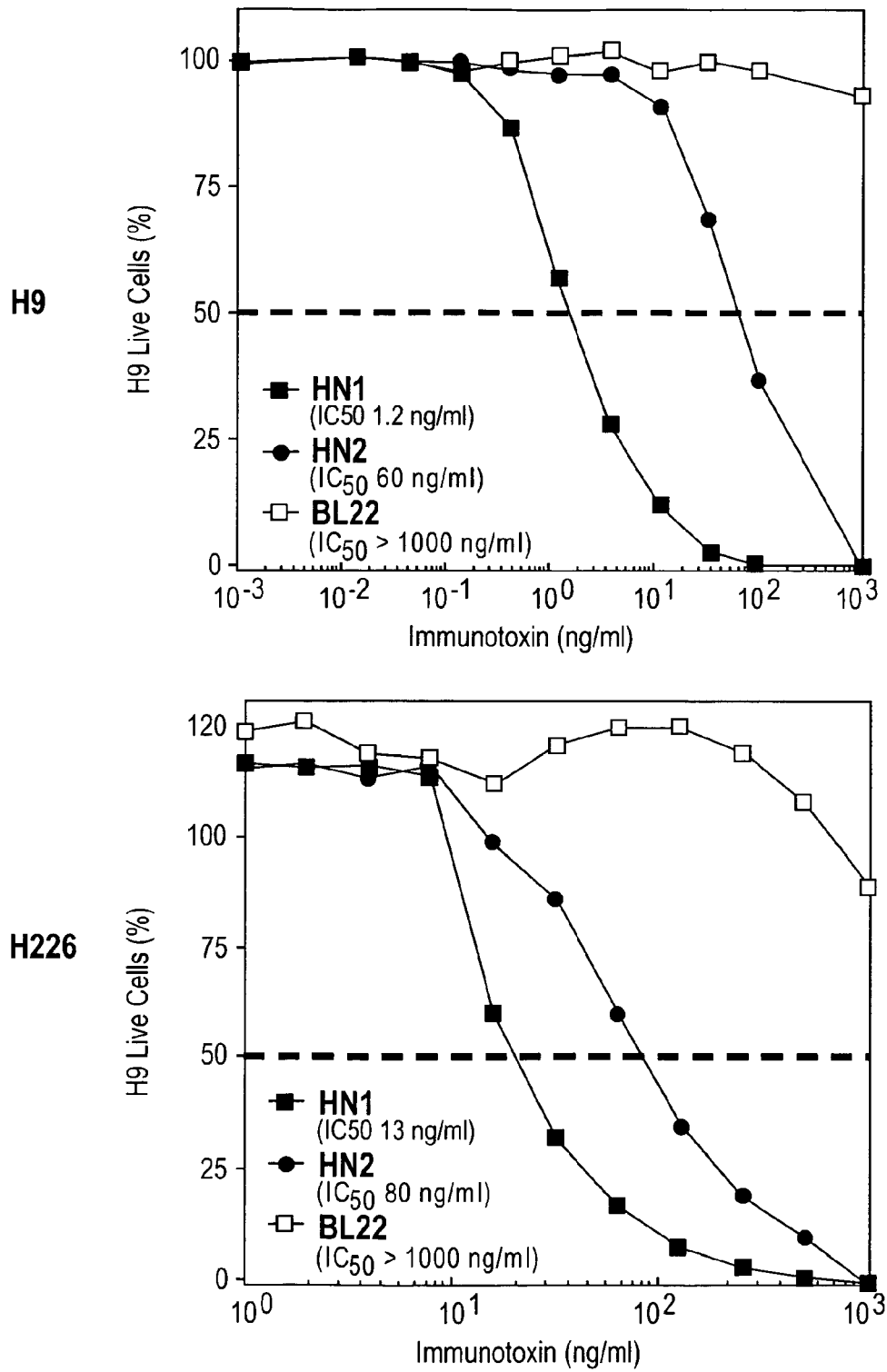
FIG. 11 illustrates inhibition of cell viability on H9 and H226 cells by the HN1 and HN2 immunotoxins. Cancer cells (10,000 per well) incubated with various concentrations of the anti-mesothelin immunotoxins containing scFv HN1, HN2 or BL22 for 72 h. Cell viability was determined by a WST assay. WST assay refers to cell viability/proliferation assay using the Cell Counting Kit-8 (CCK-8) produced by Dojindo (Rockville, Md.). WST-8 is 2-(2-methoxy-4-nitrophenyl)-3-(4-nitrophenyl)-5-(2,4-disulfophenyl)-2H-tetrazolium, monosodium salt. The dashed line indicates 50% inhibition of cell viability, which is halfway between the level of viability in the absence of toxin and that in the presence of 10 μg/mL of cycloheximide. BL22: scFv specific for CD22 used as a non-specific control. The HN1 and HN2 scFv immuntoxins had specific cytotoxic activity on H9 ($IC_{50}$=1.2 ng/ml for HN1 and $IC_{50}$=60 ng/ml for HN2) and H226 (IC50=13 ng/ml for HN1 and $IC_{50}$=80 ng/ml for HN2) cells. The HN1 immunotoxin was more potent than HN2 on both cell lines. H9: the transfected A431 cell line stably expressing mesothelin; H226: a human mesothelioma cell line.

To assess the cell killing of mesothelin-expressing cancer cells by the HN1 scFv immunotoxin, the decreased cell viability on A431/H9 and NCI-H226 cells was examined (FIG. 11). The HN1 scFv immunotoxins had high and specific cytotoxic activity on A431/H9 (IC50=1.2 ng/ml) and NCI-H226 (IC50=13 ng/ml) cells. The cytotoxic activity was similar to SS1P on cancer cells. BL22, the control immunotoxin currently in clinical trials for hairy cell leukemia and other CD22-expressing leukemias, was not cytotoxic to A431/H9 or NCI-H226 cells.

To evaluate the ADCC activity of the HN1 fully human IgG, the ADCC assays were performed on A431/H9 cells. As shown in FIG. 12, using the peripheral blood mononuclear cells (PBMC) from healthy donors, the HN1 IgG exhibited significantly high and specific activity by killing more than 40% of cancer cells while a control IgG did not. PBMC from five healthy donors were tested and their ADCC values were consistent. FIG. 12 shows representative results.

The present study demonstrates the successful isolation of human antibodies against mesothelin. However, representation of this antigen with regard to conformation, accessible binding determinants, and aggregation states that may exist at the tumor surface was not considered and would be difficult to address. Although a direct selection from our phage library by panning with cancer cells (such as OVCAR-3 or NCI-H226) that display native mesothelin molecules might be feasible, it is likely that the subtractive biopanning on mesothelin-positive and mesothelin-negative cells needed to avoid non-specific binding and the concomitant washes (>10 times) could lead to cell lysis during phage panning on cancer cells. Therefore, immobilized Fc-mesothelin was used as a panning reagent. Indeed, the fact that antibody HN1 demonstrated excellent binding and specific killing to various human cancer cells suggested that mesothelin in the form of Fc conjugate is a reasonable mimic of the cell-bound native mesothelin structure.

HN1 does not bind to the linear sequence of the CA125 binding site in the N-terminus of mesothelin, but it potently blocks the interaction of mesothelin and CA125. The results from the ELISA and Biacore binding kinetics experiments strongly suggest that HN1 recognizes a specific conformation-sensitive epitope structure. The interaction of HN1 and mesothelin may involve a conformation change. Sequence analysis shows several somatic mutations in the conserved framework regions of the HN1 VH.

The present data demonstrats that a high-affinity human mAb against tumor-associated mesothelin can be selected from a phage library constructed from the PBL of healthy non-immunized humans. The approach did not depend on immunization or vaccinated procedures or the necessity to construct a phage antibody library derived from cancer patients. Because HN1 is entirely of human origin and has high affinity, it is expected to be much less immunogenic than murine mAb and to be efficient in targeting mesothelin-expressing tumors. Consequently, it is a valuable therapeutic reagent for the treatment of cancer.

Feng et al. have reported an anti-mesothelin Fv (called m912) isolated from a human Fab library (Feng, et al., *Mol Cancer Ther* (2009) 8:1113-8). The binding of m912 IgG on human cancer cells (OVCAR-3) requires high concentrations of the mAb (625-3125 nM or 90-450 µg/mL) and m912 could only induce about 20% (compared to 40% of HN1) specific lysis of cancer cells through ADCC. These observations indicate that HN1 has a better binding affinity and cytotoxic activity than m912 for human mesothelin-expressing tumor cells.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications and accession number entries cited herein are hereby incorporated by reference in their entirety for all purposes.

What is claimed is:

1. An isolated antibody or antibody fragment that binds to mesothelin, the antibody comprising a heavy chain variable domain comprising a CDR1 comprising the amino acid sequence of SEQ ID NO:9, a CDR2 comprising the amino acid sequence of SEQ ID NO:10 and a CDR3 comprising the amino acid sequence of SEQ ID NO:11 and a light chain variable domain comprising a CDR1 comprising the amino acid sequence of SEQ ID NO:12, a CDR2 comprising the amino acid sequence of SEQ ID NO:13 and a CDR3 comprising the amino acid sequence of SEQ ID NO:14.

2. The isolated antibody or antibody fragment of claim 1, wherein the heavy chain variable domain has at least 90% sequence identity to the amino acid sequence of SEQ ID NO:2.

3. The isolated antibody or antibody fragment of claim 1, wherein the light chain variable domain has at least 90% sequence identity to the amino acid sequence of SEQ ID NO:4.

4. The isolated antibody or antibody fragment of claim 1, wherein the heavy chain variable domain has at least 90% sequence identity to the amino acid sequence of SEQ ID NO:2 and the light chain variable domain has at least 90% sequence identity to the amino acid sequence of SEQ ID NO:4.

5. The isolated antibody or antibody fragment of claim 1, wherein the mesothelin is human mesothelin.

6. The isolated antibody or antibody fragment of claim 1, wherein the antibody is a single-chain Fv (scFV).

7. The isolated antibody or antibody fragment of claim 1, wherein the antibody is an IgG.

8. The isolated antibody or antibody fragment of claim 1, wherein the antibody is a human antibody.

9. The isolated antibody or antibody fragment of claim 1, wherein the antibody is linked to an effector agent.

10. The isolated antibody or antibody fragment of claim 9, wherein the effector agent is a cytotoxin.

11. The isolated antibody or antibody fragment of claim 10, wherein the cytotoxin is a Pseudomonas exotoxin A or variant thereof.

12. An isolated nucleic acid encoding a heavy chain variable domain of an anti-mesothelin antibody, the heavy chain variable domain comprising a CDR1 comprising the amino acid sequence of SEQ ID NO:9, a CDR2 comprising the amino acid sequence of SEQ ID NO: 10, and a CDR3 comprising the amino acid sequence of SEQ ID NO:11.

13. The nucleic acid of claim 12, wherein the nucleic acid has at least 90% sequence identity with the polynucleotide sequence of SEQ ID NO:1.

14. An isolated nucleic acid encoding a light chain variable domain of an anti-mesothelin antibody, the light chain variable domain comprising a CDR1 comprising the amino acid sequence of SEQ ID NO:12, a CDR2 comprising the amino acid sequence of SEQ ID NO:13, and a CDR3 comprising the amino acid sequence of SEQ ID NO:14, and a CDR3 comprising the amino acid sequence of SEQ ID NO:14, wherein the nucleic acid comprises the polynucleotide sequence of SEQ ID NO:3.

15. A method of inhibiting CA125/mesothelin-dependent cell attachment comprising contacting a cell expressing mesothelin with an antibody of claim 1.

16. The method of claim 15, wherein the inhibiting step is performed in vivo.

17. A method of inhibiting a cancer mediated by CA125/mesothelin-dependent cell attachment comprising contacting a cell expressing mesothelin with an antibody or antibody fragment of claim 1.

18. The method of claim 17, wherein the cancer is selected from the group consisting of ovarian cancer, mesothelioma, non-small cell lung cancer, lung adenocarcinoma and pancreatic cancer.

19. The method of claim 17, wherein the antibody or antibody fragment is linked to an effector agent.

* * * * *

SEQUENCE LISTING

<160> NUMBER OF SEQ ID NOS: 61

<210> SEQ ID NO 1
<211> LENGTH: 357
<212> TYPE: DNA
<213> ORGANISM: Artificial Sequence
<220> FEATURE:
<223> OTHER INFORMATION: synthetic anti-mesothelin monoclonal antibody
      HN1 variable region heavy chain (VH)

<400> SEQUENCE: 1
caggtccagc tggtgcagtc tggggctgag gtgaagaggc ctggggcctc agtgcaggta      60
tcctgcagag catctggcta tagtatcaat acttactata tgcagtgggt gcggcaggcc     120
cctggagcag gccttgagtg gatgggcgtt atcaacccca gtggtgtcac aagttacgca     180
cagaagttcc agggcagagt cactttgacc aacgacacgt ccacaaacac agtctacatg     240
cagttgaaca gtctgacatc tgccgacacg gccgtctact actgtgcgag atgggcctta     300
tggggggact tcggtatgga cgtctgggc aagggaaccc tggtcaccgt ctcgagt        357

<210> SEQ ID NO 2
<211> LENGTH: 119
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH)

<400> SEQUENCE: 2

Gln Val Gln Leu Val Gln Ser Gly Ala Glu Val Lys Arg Pro Gly Ala
1               5                   10                  15

Ser Val Gln Val Ser Cys Arg Ala Ser Gly Tyr Ser Ile Asn Thr Tyr
            20                  25                  30

Tyr Met Gln Trp Val Arg Gln Ala Pro Gly Ala Gly Leu Glu Trp Met
        35                  40                  45

Gly Val Ile Asn Pro Ser Gly Val Thr Ser Tyr Ala Gln Lys Phe Gln
    50                  55                  60

```
Gly Arg Val Thr Leu Thr Asn Asp Thr Ser Thr Asn Thr Val Tyr Met
 65                  70                  75                  80

Gln Leu Asn Ser Leu Thr Ser Ala Asp Thr Ala Val Tyr Tyr Cys Ala
                 85                  90                  95

Arg Trp Ala Leu Trp Gly Asp Phe Gly Met Asp Val Trp Gly Lys Gly
            100                 105                 110

Thr Leu Val Thr Val Ser Ser
        115

<210> SEQ ID NO 3
<211> LENGTH: 321
<212> TYPE: DNA
<213> ORGANISM: Artificial Sequence
<220> FEATURE:
<223> OTHER INFORMATION: synthetic anti-mesothelin monoclonal antibody
      HN1 variable region kappa light chain (VL)

<400> SEQUENCE: 3
gacatccaga tgacccagtc tccttccacc ctgtctgcat ctattggaga cagagtcacc     60
atcacctgcc gggccagtga gggtatttat cactggttgg cctggtatca gcagaagcca    120
gggaaagccc ctaaactcct gatctataag gcctctagtt tagccagtgg ggctccatca    180
aggttcagcg gcagtggatc tgggacagat ttcactctca ccatcagcag cctgcagcct    240
gatgattttg caacttatta ctgccaacaa tatagtaatt atccgctcac tttcggcgga    300
gggaccaagc tggagatcaa a                                              321

<210> SEQ ID NO 4
<211> LENGTH: 107
<212> TYPE: PRT
<213> ORGANISM: Artificial Sequence
<220> FEATURE:
<223> OTHER INFORMATION: synthetic anti-mesothelin monoclonal antibody
      HN1 variable region kappa light chain (VL)

<400> SEQUENCE: 4

Asp Ile Gln Met Thr Gln Ser Pro Ser Thr Leu Ser Ala Ser Ile Gly
 1               5                  10                  15

Asp Arg Val Thr Ile Thr Cys Arg Ala Ser Glu Gly Ile Tyr His Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Ala Ser Gly Ala Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Tyr Ser Asn Tyr Pro Leu
                 85                  90                  95

Thr Phe Gly Gly Gly Thr Lys Leu Glu Ile Lys
            100                 105

<210> SEQ ID NO 5
<211> LENGTH: 351
<212> TYPE: DNA
<213> ORGANISM: Artificial Sequence
<220> FEATURE:
<223> OTHER INFORMATION: synthetic anti-mesothelin monoclonal antibody
      HN2 variable region heavy chain (VH)

<400> SEQUENCE: 5
gaggtgcagc tgttggagtc tgggggaggc ttggtacagc ctggggggtc cctgagaccc     60
```

```
tcctgtgcag cctctggatt cacctttagc agctatgcca tgagctgggt ccgccaggct      120
ccagggaagg ggctggagtg ggtctcagct attagtggta gtggtggtag cacacactac      180
gcagactccg tgaagggccg gttcaccatc tccagagaca attccaagaa cacgctgtat      240
ctgcaaatga acagcctgag agccgaggac acggccgtgt attactgtgt gagaggaggg      300
gctttgggct tgacaactg ggccgaggg acaatggtca ccgtctcgag t                 351
```

```
<210> SEQ ID NO 6
<211> LENGTH: 117
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH)

<400> SEQUENCE: 6

Glu Val Gln Leu Leu Glu Ser Gly Gly Gly Leu Val Gln Pro Gly Gly
 1               5                  10                  15

Ser Leu Arg Pro Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Gly Gly Ala Leu Gly Phe Asp Asn Trp Gly Arg Gly Thr Met
            100                 105                 110

Val Thr Val Ser Ser
        115
```

```
<210> SEQ ID NO 7
<211> LENGTH: 321
<212> TYPE: DNA
<213> ORGANISM: Artificial Sequence
<220> FEATURE:
<223> OTHER INFORMATION: synthetic anti-mesothelin monoclonal antibody
      HN2 variable region lambda light chain (VL)

<400> SEQUENCE: 7
gtgctgactc agccaccctc ggtgtctgaa gcccccaggc agagggtcac catttcctgt      60
tctggaagca cctccaacat cggaagtaat gttgttaact ggtaccagca gttcccagga      120
aagcctccca agtcgtcat ctattatgat gatctggtgg cctcaggggt ctctgaccga      180
ttttccggct ccaggtctgg cacttcagcc tccctggcca tcagtgggct ccagtctgaa      240
gatgaagctg attattattg ttcagcatgg gatgacagcc tgaatgcctg ggtgttcggt      300
ggagggacca aggtcaccgt c                                                 321
```

```
<210> SEQ ID NO 8
<211> LENGTH: 107
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL)

<400> SEQUENCE: 8
```

```
Val Leu Thr Gln Pro Pro Ser Val Ser Glu Ala Pro Arg Gln Arg Val
1               5                   10                  15

Thr Ile Ser Cys Ser Gly Ser Thr Ser Asn Ile Gly Ser Asn Val Val
            20                  25                  30

Asn Trp Tyr Gln Gln Phe Pro Gly Lys Pro Pro Lys Val Val Ile Tyr
        35                  40                  45

Tyr Asp Asp Leu Val Ala Ser Gly Val Ser Arg Phe Ser Gly Ser
    50                  55                  60

Arg Ser Gly Thr Ser Ala Ser Leu Ala Ile Ser Gly Leu Gln Ser Glu
65              70                  75                  80

Asp Glu Ala Asp Tyr Tyr Cys Ser Ala Trp Asp Ser Leu Asn Ala
                85                  90                  95

Trp Val Phe Gly Gly Gly Thr Lys Val Thr Val
            100                 105
```

<210> SEQ ID NO 9
<211> LENGTH: 8
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) complementarity
      determining region 1 (CDR1) defined according to
      ImMunoGeneTics database (IMGT)

<400> SEQUENCE: 9

```
Gly Tyr Ser Ile Asn Thr Tyr Tyr
1               5
```

<210> SEQ ID NO 10
<211> LENGTH: 7
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) complementarity
      determining region 2 (CDR2) defined according to
      ImMunoGeneTics database (IMGT)

<400> SEQUENCE: 10

```
Ile Asn Pro Ser Gly Val Thr
1               5
```

<210> SEQ ID NO 11
<211> LENGTH: 13
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) complementarity
      determining region 3 (CDR3) defined according to
      ImMunoGeneTics database (IMGT)

<400> SEQUENCE: 11

```
Ala Arg Trp Ala Leu Trp Gly Asp Phe Gly Met Asp Val
1               5                   10
```

<210> SEQ ID NO 12
<211> LENGTH: 6
<212> TYPE: PRT
<213> ORGANISM: Artificial Sequence
<220> FEATURE:
<223> OTHER INFORMATION: synthetic anti-mesothelin monoclonal antibody
      HN1 variable region kappa light chain (VL)
      complementarity determining region 1 (CDR1)
      defined according to ImMunoGeneTics database (IMGT)

```
<400> SEQUENCE: 12

Glu Gly Ile Tyr His Trp
 1               5

<210> SEQ ID NO 13
<211> LENGTH: 3
<212> TYPE: PRT
<213> ORGANISM: Artificial Sequence
<220> FEATURE:
<223> OTHER INFORMATION: synthetic anti-mesothelin monoclonal antibody
      HN1 variable region kappa light chain (VL)
      complementarity determining region 2 (CDR2)
      defined according to ImMunoGeneTics database (IMGT)

<400> SEQUENCE: 13

Lys Ala Ser
 1

<210> SEQ ID NO 14
<211> LENGTH: 9
<212> TYPE: PRT
<213> ORGANISM: Artificial Sequence
<220> FEATURE:
<223> OTHER INFORMATION: synthetic anti-mesothelin monoclonal antibody
      HN1 variable region kappa light chain (VL)
      complementarity determining region 3 (CDR3)
      defined according to ImMunoGeneTics database (IMGT)

<400> SEQUENCE: 14

Gln Gln Tyr Ser Asn Tyr Pro Leu Thr
 1               5

<210> SEQ ID NO 15
<211> LENGTH: 8
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) complementarity
      determining region 1 (CDR1) defined according to
      ImMunoGeneTics database (IMGT)

<400> SEQUENCE: 15

Gly Phe Thr Phe Ser Ser Tyr Ala
 1               5

<210> SEQ ID NO 16
<211> LENGTH: 8
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) complementarity
      determining region 2 (CDR2) defined according to
      ImMunoGeneTics database (IMGT)

<400> SEQUENCE: 16

Ile Ser Gly Ser Gly Gly Ser Thr
 1               5

<210> SEQ ID NO 17
<211> LENGTH: 10
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) complementarity
      determining region 3 (CDR3) defined according to
      ImMunoGeneTics database (IMGT)
```

-continued

```
<400> SEQUENCE: 17

Val Arg Gly Gly Ala Leu Gly Phe Asp Asn
1               5                   10

<210> SEQ ID NO 18
<211> LENGTH: 9
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL)
      complementarity determining region 1 (CDR1)
      defined according to ImMunoGeneTics database (IMGT)

<400> SEQUENCE: 18

Thr Ser Asn Ile Gly Ser Asn Val Val
1               5

<210> SEQ ID NO 19
<211> LENGTH: 3
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL)
      complementarity determining region 2 (CDR2)
      defined according to ImMunoGeneTics database (IMGT)

<400> SEQUENCE: 19

Tyr Asp Asp
1

<210> SEQ ID NO 20
<211> LENGTH: 11
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL)
      complementarity determining region 3 (CDR3)
      defined according to ImMunoGeneTics database (IMGT)

<400> SEQUENCE: 20

Ser Ala Trp Asp Asp Ser Leu Asn Ala Trp Val
1               5                   10

<210> SEQ ID NO 21
<211> LENGTH: 120
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) homolog AAW67386

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

85                  90                  95

Ala Arg Glu Gly Trp Phe Gly Asp Phe Gly Phe Asp Pro Trp Gly Gln
                100                 105                 110

Gly Thr Leu Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) homolog BAC01455

<400> SEQUENCE: 22

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Gly Tyr Gly Asp Tyr Ala Phe Asp Ile Trp Gly Gln
                100                 105                 110

Gly Thr Met Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) homolog ABM67163

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Lys Gly Tyr Gly Asp Tyr Ile Pro Asp Tyr Trp Gly Gln
                100                 105                 110

Gly Thr Leu Val Thr Val Ser Ser
        115                 120

<210> SEQ ID NO 24

```
<211> LENGTH: 120
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) homolog AAY23310

<400> SEQUENCE: 24

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Val Ala Gly Thr Tyr Leu Ile Asp Tyr Trp Gly Gln
            100                 105                 110

Gly Thr Leu Val Thr Val Ser Ser
        115                 120

<210> SEQ ID NO 25
<211> LENGTH: 122
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) homolog AAK57785

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Val Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Arg Ile Ala Val Ala Gly Thr Asp Ala Phe Asp Ile Trp
            100                 105                 110

Gly Gln Gly Thr Met Val Thr Val Cys Ser
        115                 120

<210> SEQ ID NO 26
<211> LENGTH: 122
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) homolog AAF75632

<400> SEQUENCE: 26

Glu Val Gln Leu Leu Glu Ser Gly Gly Gly Leu Val Gln Pro Gly Gly
```

```
                1               5                  10                 15
Ser Leu Arg Pro Ser Cys Ala Ala Ser Gly Phe Thr Phe Ser Ser Tyr
                20                 25                 30

Ala Met Ser Trp Val Arg Gln Ala Pro Gly Lys Gly Leu Glu Trp Val
            35                 40                 45

Ser Ala Ile Ser Gly Ser Gly Gly Ser Thr Tyr Tyr Ala Asp Ser Val
        50                 55                 60

Lys Gly Arg Phe Thr Ile Ser Arg Asp Asn Ser Lys Asn Thr Leu Tyr
65                  70                 75                  80

Leu Gln Met Asn Ser Leu Arg Ala Glu Asp Thr Ala Val Tyr Tyr Cys
                85                 90                 95

Ala Lys Ala Ser Ser Ser Gly Tyr Tyr Tyr Val His Phe Asp Tyr Trp
            100                105                110

Gly Gln Gly Thr Leu Val Thr Val Ser Ser
            115                120
```

<210> SEQ ID NO 27
<211> LENGTH: 124
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) homolog BAC02290

<400> SEQUENCE: 27

```
Glu Val Gln Leu Val Glu Ser Gly Gly Gly Val Val Gln Pro Gly Gly
1               5                  10                 15

Ser Leu Arg Pro Ser Cys Ala Ala Ser Gly Phe Thr Phe Ser Ser Tyr
                20                 25                 30

Ala Met Ser Trp Val Arg Gln Ala Pro Gly Lys Gly Leu Glu Trp Val
            35                 40                 45

Ser Ala Ile Ser Gly Ser Gly Gly Ser Thr Tyr Tyr Ala Asp Ser Val
        50                 55                 60

Lys Gly Arg Phe Thr Ile Ser Arg Asp Asn Ser Lys Asn Thr Leu Tyr
65                  70                 75                  80

Leu Gln Met Asn Ser Leu Arg Ala Glu Asp Thr Ala Val Tyr Tyr Cys
                85                 90                 95

Ala Arg Gly Ser Asp Tyr Gly Asp Tyr Leu Tyr Tyr Tyr Phe Asp
            100                105                110

Leu Trp Gly Arg Gly Thr Leu Val Thr Val Ser Ser
            115                120
```

<210> SEQ ID NO 28
<211> LENGTH: 116
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) homolog BAA36318

<400> SEQUENCE: 28

```
Glu Val Gln Leu Leu Glu Ser Gly Gly Gly Leu Val Gln Pro Gly Gly
1               5                  10                 15

Ser Leu Lys Leu Ser Cys Ala Ala Ser Gly Phe Thr Phe Ser Ser Tyr
                20                 25                 30

Ala Met Ser Trp Val Arg Gln Ala Pro Gly Lys Gly Leu Glu Trp Val
            35                 40                 45

Ser Ala Ile Ser Gly Ser Gly Gly Ser Thr Tyr Tyr Ala Asp Ser Val
        50                 55                 60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Leu Ala Phe Asp Tyr Trp Gly Gln Gly Thr Leu Val
            100                 105                 110

Thr Val Ser Ser
        115

<210> SEQ ID NO 29
<211> LENGTH: 121
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) homolog BAG62929

<400> SEQUENCE: 29

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Asp Gly Gly Asn Glu Cys Leu Phe Asp Tyr Trp Gly
            100                 105                 110

Gln Gly Thr Leu Val Thr Val Ser Ser
        115                 120

<210> SEQ ID NO 30
<211> LENGTH: 119
<212> TYPE: PRT
<213> ORGANISM: Artificial Sequence
<220> FEATURE:
<223> OTHER INFORMATION: synthetic anti-mesothelin monoclonal antibody
      HN2 variable region heavy chain (VH) homolog AAA52996

<400> SEQUENCE: 30

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Gly Trp Gly Ser Gly Phe Asp Tyr Trp Gly Gln Gly
            100                 105                 110
```

```
Thr Leu Val Thr Val Ser Ser
        115

<210> SEQ ID NO 31
<211> LENGTH: 107
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL) homolog
      BAH04805

<400> SEQUENCE: 31

Val Leu Thr Gln Pro Pro Ser Val Ser Glu Ala Pro Arg Gln Arg Val
1               5                   10                  15

Thr Ile Ser Cys Ser Gly Ser Ser Asn Ile Gly Asn Asn Ala Val
            20                  25                  30

Asn Trp Tyr Gln Gln Leu Pro Gly Lys Ala Pro Lys Leu Leu Ile Tyr
        35                  40                  45

Tyr Asp Asp Leu Leu Pro Ser Gly Val Ser Asp Arg Phe Ser Gly Ser
    50                  55                  60

Lys Ser Gly Thr Ser Ala Ser Leu Ala Ile Ser Gly Leu Gln Ser Glu
65                  70                  75                  80

Asp Glu Ala Asp Tyr Tyr Cys Ala Ala Trp Asp Asp Ser Leu Asn Ala
                85                  90                  95

Val Val Phe Gly Gly Gly Thr Lys Leu Thr Val
                100                 105

<210> SEQ ID NO 32
<211> LENGTH: 107
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL) homolog
      AAQ56716

<400> SEQUENCE: 32

Val Leu Thr Gln Pro Pro Ser Val Ser Glu Ala Pro Arg Gln Arg Val
1               5                   10                  15

Thr Ile Ser Cys Ser Gly Ser Ser Asn Ile Gly Asn Asn Ala Val
            20                  25                  30

Asn Trp Tyr Gln Gln Leu Pro Gly Lys Ala Pro Lys Leu Leu Ile Tyr
        35                  40                  45

Tyr Asp Asp Leu Leu Pro Ser Gly Val Ser Asp Arg Phe Ser Gly Ser
    50                  55                  60

Lys Ser Gly Thr Ser Ala Ser Leu Ala Ile Ser Gly Leu Gln Ser Glu
65                  70                  75                  80

Asp Glu Ala Asp Tyr Tyr Cys Ala Ala Trp Asp Asp Ser Leu Ala Ser
                85                  90                  95

Tyr Val Phe Gly Gly Gly Thr Lys Leu Thr Val
                100                 105

<210> SEQ ID NO 33
<211> LENGTH: 107
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL) homolog
      CAG27374

<400> SEQUENCE: 33
```

Val Leu Thr Gln Pro Pro Ser Val Ser Glu Ala Pro Arg Gln Arg Val
1               5                   10                  15

Thr Ile Ser Cys Ser Gly Ser Ser Asn Ile Gly Asn Asn Ala Val
            20                  25                  30

Asn Trp Tyr Gln Gln Leu Pro Gly Lys Ala Pro Lys Leu Leu Ile Tyr
        35                  40                  45

Tyr Asp Asp Leu Leu Pro Ser Gly Val Ser Asp Arg Phe Ser Gly Ser
    50                  55                  60

Lys Ser Gly Thr Ser Ala Ser Leu Ala Ile Ser Gly Leu Gln Ser Glu
65              70                  75                  80

Asp Glu Ala Asp Tyr Tyr Cys Ala Ala Trp Asp Ser Leu Asn Gly
                85                  90                  95

Tyr Val Phe Gly Thr Gly Thr Lys Val Thr Val
            100                 105

<210> SEQ ID NO 34
<211> LENGTH: 107
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL) homolog
      AAZ13621

<400> SEQUENCE: 34

Val Leu Thr Gln Pro Pro Ser Val Ser Glu Ala Pro Arg Gln Arg Val
1               5                   10                  15

Thr Ile Ser Cys Ser Gly Ser Ser Asn Ile Gly Asn Asn Ala Val
            20                  25                  30

Asn Trp Tyr Gln Gln Leu Pro Gly Lys Ala Pro Lys Leu Leu Ile Tyr
        35                  40                  45

Tyr Asp Asp Leu Leu Pro Ser Gly Val Ser Asp Arg Phe Ser Gly Ser
    50                  55                  60

Lys Ser Gly Thr Ser Ala Ser Leu Ala Ile Ser Gly Leu Gln Ser Glu
65              70                  75                  80

Asp Glu Ala Asp Tyr Tyr Cys Ala Ala Trp Asp Ser Leu Asn Gly
                85                  90                  95

Pro Val Phe Gly Gly Gly Thr Lys Leu Thr Val
            100                 105

<210> SEQ ID NO 35
<211> LENGTH: 107
<212> TYPE: PRT
<213> ORGANISM: Artificial Sequence
<220> FEATURE:
<223> OTHER INFORMATION: synthetic anti-mesothelin monoclonal antibody
      HN2 variable region lambda light chain (VL) homolog
      CAD23536

<400> SEQUENCE: 35

Val Leu Thr Gln Pro Pro Ser Val Ser Glu Ala Pro Arg Gln Arg Val
1               5                   10                  15

Thr Ile Ser Cys Ser Gly Ser Ser Asn Ile Gly Asn Asn Ala Val
            20                  25                  30

Asn Trp Tyr Gln Gln Leu Pro Gly Arg Ala Pro Lys Leu Leu Ile Tyr
        35                  40                  45

Tyr Asp Asp Leu Leu Pro Ser Gly Val Ser Asp Arg Phe Ser Gly Ser
    50                  55                  60

Lys Ser Gly Thr Ser Ala Ser Leu Ala Ile Ser Gly Leu Gln Ser Glu

```
                65                  70                  75                  80
Asp Glu Ala Asp Tyr Tyr Cys Ala Ala Trp Asp Asp Ser Leu Asn Gly
                    85                  90                  95
Val Val Phe Gly Gly Gly Thr Lys Leu Thr Val
            100                 105
```

```
<210> SEQ ID NO 36
<211> LENGTH: 4
<212> TYPE: PRT
<213> ORGANISM: Artificial Sequence
<220> FEATURE:
<223> OTHER INFORMATION: synthetic peptide linker separating VH and VL
      regions

<400> SEQUENCE: 36

Gly Gly Gly Ser
1

<210> SEQ ID NO 37
<211> LENGTH: 4
<212> TYPE: PRT
<213> ORGANISM: Artificial Sequence
<220> FEATURE:
<223> OTHER INFORMATION: synthetic Pseudomonas exotoxin additional
      carboxyl terminus

<400> SEQUENCE: 37

Lys Asp Glu Leu
1

<210> SEQ ID NO 38
<211> LENGTH: 4
<212> TYPE: PRT
<213> ORGANISM: Artificial Sequence
<220> FEATURE:
<223> OTHER INFORMATION: synthetic Pseudomonas exotoxin additional
      carboxyl terminus

<400> SEQUENCE: 38

Arg Glu Asp Leu
1

<210> SEQ ID NO 39
<211> LENGTH: 5
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) complementarity
      determining region 1 (CDR1) defined according to
      Kabat

<400> SEQUENCE: 39

Thr Tyr Tyr Met Gln
1               5

<210> SEQ ID NO 40
<211> LENGTH: 16
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) complementarity
      determining region 2 (CDR2) defined according to
      Kabat

<400> SEQUENCE: 40

Val Ile Asn Pro Ser Gly Val Thr Ser Tyr Ala Gln Lys Phe Gln Gly
```

<210> SEQ ID NO 41
<211> LENGTH: 11
<212> TYPE: PRT
<213> ORGANISM: Artificial Sequence
<220> FEATURE:
<223> OTHER INFORMATION: synthetic anti-mesothelin monoclonal antibody
      HN1 variable region heavy chain (VH) complementarity
      determining region 3 (CDR3) defined according to
      Kabat

<400> SEQUENCE: 41

Trp Ala Leu Trp Gly Asp Phe Gly Met Asp Val
 1               5                  10

<210> SEQ ID NO 42
<211> LENGTH: 11
<212> TYPE: PRT
<213> ORGANISM: Artificial Sequence
<220> FEATURE:
<223> OTHER INFORMATION: synthetic anti-mesothelin monoclonal antibody
      HN1 variable region kappa light chain (VL)
      complementarity determining region 1 (CDR1)
      defined according to Kabat

<400> SEQUENCE: 42

Arg Ala Ser Glu Gly Ile Tyr His Trp Leu Ala
 1               5                  10

<210> SEQ ID NO 43
<211> LENGTH: 6
<212> TYPE: PRT
<213> ORGANISM: Artificial Sequence
<220> FEATURE:
<223> OTHER INFORMATION: synthetic anti-mesothelin monoclonal antibody
      HN1 variable region kappa light chain (VL)
      complementarity determining region 2 (CDR2)
      defined according to Kabat

<400> SEQUENCE: 43

Lys Ala Ser Leu Ala Ser
 1               5

<210> SEQ ID NO 44
<211> LENGTH: 9
<212> TYPE: PRT
<213> ORGANISM: Artificial Sequence
<220> FEATURE:
<223> OTHER INFORMATION: synthetic anti-mesothelin monoclonal antibody
      HN1 variable region kappa light chain (VL)
      complementarity determining region 3 (CDR3)
      defined according to Kabat

<400> SEQUENCE: 44

Gln Gln Tyr Ser Asn Tyr Pro Leu Thr
 1               5

<210> SEQ ID NO 45
<211> LENGTH: 732
<212> TYPE: DNA
<213> ORGANISM: Artificial Sequence
<220> FEATURE:
<223> OTHER INFORMATION: synthetic anti-mesothelin monoclonal antibody
      HN1 single-chain Fv antibody (scFv)

<400> SEQUENCE: 45
atggcccagg tccagctggt gcagtctggg gctgaggtga agaggcctgg ggcctcagtg      60
caggtatcct gcagagcatc tggctatagt atcaatactt actatatgca gtgggtgcgg     120

```
caggccctg gagcaggcct tgagtggatg ggcgttatca accccagtgg tgtcacaagt        180
tacgcacaga agttccaggg cagagtcact ttgaccaacg acacgtccac aaacacagtc        240
tacatgcagt tgaacagtct gacatctgcc gacacggccg tctactactg tgcgagatgg        300
gccttatggg gggacttcgg tatggacgtc tggggcaagg gaaccctggt caccgtctcg        360
agtggtggag gcggttcagg cggaggtggc agcggcggtg gcggatcgga catccagatg        420
acccagtctc cttccaccct gtctgcatct attggagaca gagtcaccat cacctgccgg        480
gccagtgagg gtatttatca ctggttggcc tggtatcagc agaagccagg gaaagcccct        540
aaactcctga tctataaggc ctctagttta gccagtgggg ccccatcaag gttcagcggc        600
agtggatctg ggacagattt cactctcacc atcagcagcc tgcagcctga tgattttgca        660
acttattact gccaacaata tagtaattat ccgctcactt tcggcggagg gaccaagctg        720
gagatcaaac gt                                                           732
```

<210> SEQ ID NO 46
<211> LENGTH: 244
<212> TYPE: PRT
<213> ORGANISM: Artificial Sequence
<220> FEATURE:
<223> OTHER INFORMATION: synthetic anti-mesothelin monoclonal antibody
      HN1 single-chain Fv antibody (scFv)

<400> SEQUENCE: 46

```
Met Ala Gln Val Gln Leu Val Gln Ser Gly Ala Glu Val Lys Arg Pro
 1               5                  10                  15

Gly Ala Ser Val Gln Val Ser Cys Arg Ala Ser Gly Tyr Ser Ile Asn
             20                  25                  30

Thr Tyr Tyr Met Gln Trp Val Arg Gln Ala Pro Gly Ala Gly Leu Glu
         35                  40                  45

Trp Met Gly Val Ile Asn Pro Ser Gly Val Thr Ser Tyr Ala Gln Lys
 50                  55                  60

Phe Gln Gly Arg Val Thr Leu Thr Asn Asp Thr Ser Thr Asn Thr Val
 65                  70                  75                  80

Tyr Met Gln Leu Asn Ser Leu Thr Ser Ala Asp Thr Ala Val Tyr Tyr
                 85                  90                  95

Cys Ala Arg Trp Ala Leu Trp Gly Asp Phe Gly Met Asp Val Trp Gly
            100                 105                 110

Lys Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
        130                 135                 140

Ser Thr Leu Ser Ala Ser Ile Gly Asp Arg Val Thr Ile Thr Cys Arg
145                 150                 155                 160

Ala Ser Glu Gly Ile Tyr His Trp Leu Ala Trp Tyr Gln Gln Lys Pro
                165                 170                 175

Gly Lys Ala Pro Lys Leu Leu Ile Tyr Lys Ala Ser Ser Leu Ala Ser
            180                 185                 190

Gly Ala Pro Ser Arg Phe Ser Gly Ser Gly Ser Gly Thr Asp Phe Thr
        195                 200                 205

Leu Thr Ile Ser Ser Leu Gln Pro Asp Asp Phe Ala Thr Tyr Tyr Cys
        210                 215                 220

Gln Gln Tyr Ser Asn Tyr Pro Leu Thr Phe Gly Gly Gly Thr Lys Leu
225                 230                 235                 240

Glu Ile Lys Arg
```

<210> SEQ ID NO 47
<211> LENGTH: 993
<212> TYPE: DNA
<213> ORGANISM: Artificial Sequence
<220> FEATURE:
<223> OTHER INFORMATION: synthetic heavy chain IgG1 constant region

<400> SEQUENCE: 47

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggg     360
ccgtcagtct tcctcttccc cccaaaaccc aaggacaccc tcatgatctc ccggaccccc     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993
```

<210> SEQ ID NO 48
<211> LENGTH: 329
<212> TYPE: PRT
<213> ORGANISM: Artificial Sequence
<220> FEATURE:
<223> OTHER INFORMATION: synthetic heavy chain IgG1 constant region

<400> SEQUENCE: 48

```
Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                    130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 49
<211> LENGTH: 1515
<212> TYPE: DNA
<213> ORGANISM: Artificial Sequence
<220> FEATURE:
<223> OTHER INFORMATION: synthetic anti-mesothelin monoclonal antibody
      HN1 including IgG1 heavy chain constant region

<400> SEQUENCE: 49

```
atgggcggta ggcgtgtacg gtgggaggtc tatataagca gagctgggta cgtgaaccgt      60
cagatcgcct ggagacgcca tcgaattctg agcacacagg acctcaccat ggactggacc     120
tggaggatcc tcttcttggt ggcagcagcc acaggagctc actcccaggt ccagctggtg     180
cagtctgggg ctgaggtgaa gaggcctggg gcctcagtgc aggtatcctg cagagcatct     240
ggctatagta tcaatactta ctatatgcag tgggtgcggc aggcccctgg agcaggcctt     300
gagtggatgg gcgttatcaa ccccagtggt gtcacaagtt acgcacagaa gttccagggc     360
agagtcactt tgaccaacga cacgtccaca aacacagtct acatgcagtt gaacagtctg     420
acatctgccg acacggccgt ctactactgt gcgagatggg ccttatgggg gacttcggt      480 atggacgtct ggggcaaggg aaccctggtc accgtctcga gtgcctccac caagggccca     540
tcggtcttcc ccctggcacc ctcctccaag agcacctctg ggggcacagc ggccctgggc     600
tgcctggtca aggactactt ccccgaaccg gtgacggtgt cgtggaactc aggcgccctg     660
accagcggcg tgcacacctt cccggctgtc ctacagtcct caggactcta ctccctcagc     720
agcgtggtga ccgtgccctc agcagcttgg gcacccagac ctacatctgc aacgtgaat      780 cacaagccca gcaacaccaa ggtggacaag aaagttgagc ccaaatcttg tgacaaaact     840
cacacatgcc caccgtgccc agcacctgaa ctcctggggg gaccgtcagt cttcctcttc     900
cccccaaaac ccaaggacac cctcatgatc tcccggaccc ctgaggtcac atgcgtggtg     960
```

-continued

```
gtggacgtga gccacgaaga ccctgaggtc aagttcaact ggtacgtgga cggcgtggag    1020
gtgcataatg ccaagacaaa gccgcgggag gagcagtaca acagcacgta ccgtgtggtc    1080
agcgtcctca ccgtcctgca ccaggactgg ctgaatggca aggagtacaa gtgcaaggtc    1140
tccaacaaag ccctcccagc ccccatcgag aaaaccatct ccaaagccaa agggcagccc    1200
cgagaaccac aggtgtacac cctgccccca tcccgggatg agctgaccaa gaaccaggtc    1260
agcctgacct gcctggtcaa aggcttctat cccagcgaca tcgccgtgga gtgggagagc    1320
aatgggcagc cggagaacaa ctacaagacc acgcctcccg tgctggactc cgacggctcc    1380
ttcttcctct acagcaagct caccgtggac aagagcaggt ggcagcaggg gaacgtcttc    1440
tcatgctccg tgatgcatga ggctctgcac aaccactaca cgcagaagag cctctccctg    1500
tctccgggta atga                                                      1515
```

```
<210> SEQ ID NO 50
<211> LENGTH: 504
<212> TYPE: PRT
<213> ORGANISM: Artificial Sequence
<220> FEATURE:
<223> OTHER INFORMATION: synthetic anti-mesothelin monoclonal antibody
      HN1 including IgG1 heavy chain constant region

<400> SEQUENCE: 50

Met Gly Gly Arg Arg Val Arg Trp Glu Val Tyr Ile Ser Arg Ala Gly
 1               5                  10                  15

Tyr Val Asn Arg Gln Ile Ala Trp Arg Arg His Arg Ile Leu Ser Thr
            20                  25                  30

Gln Asp Leu Thr Met Asp Trp Thr Trp Arg Ile Leu Phe Leu Val Ala
        35                  40                  45

Ala Ala Thr Gly Ala His Ser Gln Val Gln Leu Val Gln Ser Gly Ala
    50                  55                  60

Glu Val Lys Arg Pro Gly Ala Ser Val Gln Val Ser Cys Arg Ala Ser
65                  70                  75                  80

Gly Tyr Ser Ile Asn Thr Tyr Tyr Met Gln Trp Val Arg Gln Ala Pro
                85                  90                  95

Gly Ala Gly Leu Glu Trp Met Gly Val Ile Asn Pro Ser Gly Val Thr
            100                 105                 110

Ser Tyr Ala Gln Lys Phe Gln Gly Arg Val Thr Leu Thr Asn Asp Thr
        115                 120                 125

Ser Thr Asn Thr Val Tyr Met Gln Leu Asn Ser Leu Thr Ser Ala Asp
    130                 135                 140

Thr Ala Val Tyr Tyr Cys Ala Arg Trp Ala Leu Trp Gly Asp Phe Gly
145                 150                 155                 160

Met Asp Val Trp Gly Lys Gly Thr Leu Val Thr Val Ser Ser Ala Ser
                165                 170                 175

Thr Lys Gly Pro Ser Val Phe Pro Leu Ala Pro Ser Ser Lys Ser Thr
            180                 185                 190

Ser Gly Gly Thr Ala Ala Leu Gly Cys Leu Val Lys Asp Tyr Phe Pro
        195                 200                 205

Glu Pro Val Thr Val Ser Trp Asn Ser Gly Ala Leu Thr Ser Gly Val
    210                 215                 220

His Thr Phe Pro Ala Val Leu Gln Ser Ser Gly Leu Tyr Ser Leu Ser
225                 230                 235                 240

Ser Val Val Thr Val Pro Ser Ser Ser Leu Gly Thr Gln Thr Tyr Ile
                245                 250                 255
```

-continued

```
Cys Asn Val Asn His Lys Pro Ser Asn Thr Lys Val Asp Lys Lys Val
            260                 265                 270
Glu Pro Lys Ser Cys Asp Lys Thr His Thr Cys Pro Pro Cys Pro Ala
        275                 280                 285
Pro Glu Leu Leu Gly Gly Pro Ser Val Phe Leu Phe Pro Pro Lys Pro
    290                 295                 300
Lys Asp Thr Leu Met Ile Ser Arg Thr Pro Glu Val Thr Cys Val Val
305                 310                 315                 320
Val Asp Val Ser His Glu Asp Pro Glu Val Lys Phe Asn Trp Tyr Val
                325                 330                 335
Asp Gly Val Glu Val His Asn Ala Lys Thr Lys Pro Arg Glu Glu Gln
            340                 345                 350
Tyr Asn Ser Thr Tyr Arg Val Val Ser Val Leu Thr Val Leu His Gln
        355                 360                 365
Asp Trp Leu Asn Gly Lys Glu Tyr Lys Cys Lys Val Ser Asn Lys Ala
    370                 375                 380
Leu Pro Ala Pro Ile Glu Lys Thr Ile Ser Lys Ala Lys Gly Gln Pro
385                 390                 395                 400
Arg Glu Pro Gln Val Tyr Thr Leu Pro Pro Ser Arg Asp Glu Leu Thr
                405                 410                 415
Lys Asn Gln Val Ser Leu Thr Cys Leu Val Lys Gly Phe Tyr Pro Ser
            420                 425                 430
Asp Ile Ala Val Glu Trp Glu Ser Asn Gly Gln Pro Glu Asn Asn Tyr
        435                 440                 445
Lys Thr Thr Pro Pro Val Leu Asp Ser Asp Gly Ser Phe Phe Leu Tyr
    450                 455                 460
Ser Lys Leu Thr Val Asp Lys Ser Arg Trp Gln Gln Gly Asn Val Phe
465                 470                 475                 480
Ser Cys Ser Val Met His Glu Ala Leu His Asn His Tyr Thr Gln Lys
                485                 490                 495
Ser Leu Ser Leu Ser Pro Gly Lys
            500
```

```
<210> SEQ ID NO 51
<211> LENGTH: 321
<212> TYPE: DNA
<213> ORGANISM: Artificial Sequence
<220> FEATURE:
<223> OTHER INFORMATION: synthetic kappa light chain

<400> SEQUENCE: 51
acggtggctg caccatctgt cttcatcttc ccgccatctg atgagcagtt gaaatctgga     60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat cagggcctga gttcgcccgt cacaaagagc    300
ttcaacaggg gagagtgtta a                                              321

<210> SEQ ID NO 52
<211> LENGTH: 106
<212> TYPE: PRT
<213> ORGANISM: Artificial Sequence
<220> FEATURE:
<223> OTHER INFORMATION: synthetic kappa light chain

<400> SEQUENCE: 52
```

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65              70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 53
<211> LENGTH: 813
<212> TYPE: DNA
<213> ORGANISM: Artificial Sequence
<220> FEATURE:
<223> OTHER INFORMATION: synthetic anti-mesothelin monoclonal antibody
      HN1 light chain including kappa chain

<400> SEQUENCE: 53

```
atgggcggta ggcgtgtacg gtgggaggtc tatataagca gagctgggta cgtgaaccgt      60
cagatcgcct ggagacgcca tcgaattctg agcacacagg acctcaccat ggtgttgcag     120
acccaggtct tcataagctt gttgctctgg atctctggtg cctacgggga catccagatg     180
acccagtctc cttccaccct gtctgcatct attggagaca gagtcaccat cacctgccgg     240
gccagtgagg gtatttatca ctggttggcc tggtatcagc agaagccagg aaagcccct      300 aaactcctga tctataaggc ctctagttta gccagtgggg ctccatcaag gttcagcggc     360
agtggatctg ggacagattt cactctcacc atcagcagcc tgcagcctga tgattttgca     420
acttattact gccaacaata tagtaattat ccgctcactt tcggcggagg gaccaagctg     480
gagatcaaac gtacggtggc tgcaccatct gtcttcatct tcccgccatc tgatgagcag     540
ttgaaatctg gaactgcctc tgttgtgtgc ctgctgaata acttctatcc cagagaggcc     600
aaagtacagt ggaaggtgga taacgccctc caatcgggta actcccagga gagtgtcaca     660
gagcaggaca gcaaggacag cacctacagc ctcagcagca ccctgacgct gagcaaagca     720
gactacgaga aacacaaagt ctacgcctgc gaagtcaccc atcagggcct gagttcgccc     780
gtcacaaaga gcttcaacag gggagagtgt taa                                  813
```

<210> SEQ ID NO 54
<211> LENGTH: 270
<212> TYPE: PRT
<213> ORGANISM: Artificial Sequence
<220> FEATURE:
<223> OTHER INFORMATION: synthetic anti-mesothelin monoclonal antibody
      HN1 light chain including kappa chain

<400> SEQUENCE: 54

```
Met Gly Gly Arg Arg Val Arg Trp Glu Val Tyr Ile Ser Arg Ala Gly
 1               5                  10                  15

Tyr Val Asn Arg Gln Ile Ala Trp Arg Arg His Arg Ile Leu Ser Thr
            20                  25                  30

Gln Asp Leu Thr Met Val Leu Gln Thr Gln Val Phe Ile Ser Leu Leu
        35                  40                  45
```

```
Leu Trp Ile Ser Gly Ala Tyr Gly Asp Ile Gln Met Thr Gln Ser Pro
         50                  55                  60

Ser Thr Leu Ser Ala Ser Ile Gly Asp Arg Val Thr Ile Thr Cys Arg
 65                  70                  75                  80

Ala Ser Glu Gly Ile Tyr His Trp Leu Ala Trp Tyr Gln Gln Lys Pro
                     85                  90                  95

Gly Lys Ala Pro Lys Leu Leu Ile Tyr Lys Ala Ser Ser Leu Ala Ser
                100                 105                 110

Gly Ala Pro Ser Arg Phe Ser Gly Ser Gly Ser Gly Thr Asp Phe Thr
                115                 120                 125

Leu Thr Ile Ser Ser Leu Gln Pro Asp Asp Phe Ala Thr Tyr Tyr Cys
        130                 135                 140

Gln Gln Tyr Ser Asn Tyr Pro Leu Thr Phe Gly Gly Gly Thr Lys Leu
145                 150                 155                 160

Glu Ile Lys Arg Thr Val Ala Ala Pro Ser Val Phe Ile Phe Pro Pro
                165                 170                 175

Ser Asp Glu Gln Leu Lys Ser Gly Thr Ala Ser Val Val Cys Leu Leu
                180                 185                 190

Asn Asn Phe Tyr Pro Arg Glu Ala Lys Val Gln Trp Lys Val Asp Asn
                195                 200                 205

Ala Leu Gln Ser Gly Asn Ser Gln Glu Ser Val Thr Glu Gln Asp Ser
210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
                260                 265                 270

<210> SEQ ID NO 55
<211> LENGTH: 5
<212> TYPE: PRT
<213> ORGANISM: Artificial Sequence
<220> FEATURE:
<223> OTHER INFORMATION: synthetic Pseudomonas exotoxin native
      C-terminal end, residues 609-613

<400> SEQUENCE: 55

Arg Glu Asp Leu Lys
 1               5

<210> SEQ ID NO 56
<211> LENGTH: 98
<212> TYPE: PRT
<213> ORGANISM: Homo sapiens
<220> FEATURE:
<223> OTHER INFORMATION: variable heavy chain region IGHV1-46 germline
      sequence

<400> SEQUENCE: 56

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
```

```
                65                  70                  75                  80
Met Gln Leu Ser Ser Leu Arg Ser Glu Asp Thr Ala Val Tyr Tyr Cys
                    85                  90                  95

Ala Arg

<210> SEQ ID NO 57
<211> LENGTH: 95
<212> TYPE: PRT
<213> ORGANISM: Homo sapiens
<220> FEATURE:
<223> OTHER INFORMATION: variable light chain region IGKV1-5*03 germline
      sequence

<400> SEQUENCE: 57

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro
                85                  90                  95

<210> SEQ ID NO 58
<211> LENGTH: 43
<212> TYPE: DNA
<213> ORGANISM: Artificial Sequence
<220> FEATURE:
<223> OTHER INFORMATION: synthetic anti-mesothelin monoclonal antibody
      HN1 scFv VH region PCR amplification forward primer
      VH-HN1-F

<400> SEQUENCE: 58
gaggaggaag agctcactcc caggtccagc tggtgcagtc tgg                        43

<210> SEQ ID NO 59
<211> LENGTH: 49
<212> TYPE: DNA
<213> ORGANISM: Artificial Sequence
<220> FEATURE:
<223> OTHER INFORMATION: synthetic anti-mesothelin monoclonal antibody
      HN1 scFv VH region PCR amplification reverse primer
      VH-HN1-R

<400> SEQUENCE: 59
gaggaggaag ggcccttggt ggaggcactc gagacggtga ccagggttc                  49

<210> SEQ ID NO 60
<211> LENGTH: 66
<212> TYPE: DNA
<213> ORGANISM: Artificial Sequence
<220> FEATURE:
<223> OTHER INFORMATION: synthetic anti-mesothelin monoclonal antibody
      HN1 scFv VL region PCR amplification forward primer
      VL-HN1-F

<400> SEQUENCE: 60
gaggaggaaa agcttgttgc tctggatctc tggtgcctac ggggacatcc agatgaccca      60
gtctcc                                                                 66
```

```
<210> SEQ ID NO 61
<211> LENGTH: 35
<212> TYPE: DNA
<213> ORGANISM: Artificial Sequence
<220> FEATURE:
<223> OTHER INFORMATION: synthetic anti-mesothelin monoclonal antibody
      HN1 scFv VL region PCR amplification reverse primer
      VL-HN1-R

<400> SEQUENCE: 61
gaggaggagc gtacgtttga tctccagctt ggtcc                              35
```